US007226761B2

(12) United States Patent
Miasnikov et al.

(10) Patent No.: US 7,226,761 B2
(45) Date of Patent: Jun. 5, 2007

(54) MANUFACTURE OF FIVE-CARBON SUGARS AND SUGAR ALCOHOLS

(75) Inventors: Andrei Miasnikov, Kantvik (FI); Heikki Ojamo, Kirkkonummi (FI); Mira Povelainen, Espoo (FI); Hakan Gros, Kantvik (FI); Mervi Toivari, Espoo (FI); Peter Richard, Helsinki (FI); Laura Ruohonen, Helsinki (FI); Kari Koivuranta, Helsinki (FI); John Londesborough, Helsinki (FI); Aristos Aristidou, Maple Grove, MN (US); Merja Penttila, Helsinki (FI); Claire Plazanet-Menut, Paris (FR); Josef Deutscher, Fontenay le Fleury (FR)

(73) Assignee: Danisco Sweeteners Oy, Kotka (FI)

( * ) Notice: Subject to any disclaimer, the term of this patent is extended or adjusted under 35 U.S.C. 154(b) by 27 days.

(21) Appl. No.: 09/908,744

(22) Filed: Jul. 20, 2001

(65) Prior Publication Data

US 2003/0068791 A1    Apr. 10, 2003

Related U.S. Application Data

(63) Continuation-in-part of application No. PCT/FI01/00051, filed on Jan. 22, 2001, and a continuation-in-part of application No. 09/488,581, filed on Jan. 21, 2000, now abandoned, which is a continuation-in-part of application No. 08/790,585, filed on Jan. 29, 1997, now Pat. No. 6,723,540, which is a continuation of application No. 08/368,395, filed on Jan. 3, 1995, now Pat. No. 5,631,150, which is a continuation of application No. 08/110,672, filed on Aug. 24, 1993, now abandoned, which is a continuation-in-part of application No. 07/973,325, filed on Nov. 5, 1992, now abandoned.

(51) Int. Cl.
*C12P 19/02* (2006.01)
*C12N 1/19* (2006.01)
*C12N 1/21* (2006.01)
*C12N 1/15* (2006.01)

(52) U.S. Cl. .............. 435/105; 435/254.11; 435/254.2; 435/252.3

(58) Field of Classification Search ................ 435/105, 435/69.1, 254.1, 254.2, 254, 254.23
See application file for complete search history.

(56) References Cited

U.S. PATENT DOCUMENTS

| | | | |
|---|---|---|---|
| 3,586,537 A | 6/1971 | Steiner et al. ............... 127/37 |
| 3,607,648 A | 9/1971 | Kobe et al. .................. 195/28 |
| 3,619,369 A | 11/1971 | Onishi et al. ................ 195/37 |
| 3,784,408 A | 1/1974 | Jaffe et al. .................... 127/37 |
| 3,970,522 A | 7/1976 | Sasajima et al. ............ 195/112 |
| 4,008,285 A | 2/1977 | Melaja et al. ............... 260/635 |
| 4,066,711 A | 1/1978 | Melaja et al. ............... 260/637 |
| 4,075,406 A | 2/1978 | Melaja et al. ................ 536/1 |
| 5,081,026 A | 1/1992 | Heikkilä et al. ............ 435/158 |
| 5,281,531 A | 1/1994 | Miyagawa et al. ..... 435/252.31 |
| 5,631,150 A | 5/1997 | Harkki et al. ............... 435/105 |
| 5,798,237 A | 8/1998 | Picataggio et al. ......... 435/139 |
| 5,866,382 A | 2/1999 | Hallborn et al. |
| 6,723,540 B1 | 4/2004 | Harkki et al. ............... 435/105 |

FOREIGN PATENT DOCUMENTS

| | | |
|---|---|---|
| CA | 840981 | 5/1970 |
| DE | 40 09 676 A1 | 10/1991 |
| EP | 0 450 430 A2 | 10/1991 |
| EP | 0 974 646 | 1/2000 |
| EP | 1 022 341 | 7/2000 |
| EP | 1 029 925 | 8/2000 |
| FR | 2 641 545 | 7/1990 |
| FR | 2 762 011 | 10/1998 |
| FR | 2 772 788 | 6/1999 |
| WO | WO 88/05467 | 7/1988 |
| WO | WO 90/08193 | 7/1990 |
| WO | WO 91/10740 | 7/1991 |
| WO | WO 91/15588 | 10/1991 |
| WO | WO 94/10325 | 5/1994 |
| WO | WO 99/46363 | 9/1999 |

OTHER PUBLICATIONS

Bailey, Science vol. 252, pp. 1668-1675 (1991).*
Parekh et al., Appl. Microbiol. Biotechno., vol. 54, pp. 287-301 (2000).*
Onishi et al. Appl. Microl., vol. 18, No. 6, p. 1031-1035 (1969).*
Halborn et al. (Biotechnology 9: pp. 1090-1095 (1991).*
Hausman, S. Z., and London, J., "Purification and Characterization of Ribitol-5-Phosphate and Xylitol-5-Phosphate Dehydrogenases from Strains of *Lactobacillus casei*," *Journal of Bacteriology*, (169) (4) :1651-1655, American Society for Microbiology (1987).
Cordwell, S.J., "Microbial genomes and 'missing' enzymes: redefining biochemical pathways," *Arch. Microbiol. 172*:269-279, Springer-Verlag (Nov. 1999).
Aho, S., "Structural and functional analysis of *Trichoderma reesei* endoglucanase I expressed in yeast *Saccaromyces* (sic) *cerevisiae*," *FEB Letts. 291*(1):45-49, Elsevier Science Publishers B.V., Amsterdam (Oct. 1991).
Ammerer, G., "Expression of Genes in Yeast Using the *ADCI* Promoter," *Meth. Enzymol. 101*:192-201, Academic Press Inc., New York (1983).

(Continued)

*Primary Examiner*—Nancy Vogel
(74) *Attorney, Agent, or Firm*—Sterne, Kessler, Goldstein & Fox P.L.L.C.

(57) ABSTRACT

The invention relates to the methods of manufacturing five-carbon sugars and sugar alcohols as well as other compounds derived from pentose-phosphate pathway from readily available substrates such a hexoses using metabolically engineered microbial hosts.

8 Claims, 25 Drawing Sheets

OTHER PUBLICATIONS

Bailey, J.E., "Toward a Science of Metabolic Engineering," *Science* 252:1668-1675, Association for the Advancement of Science, Washington D.C. (Jun. 1991).

Barbosa, M.F.S. et al., "Screening of yeasts for production of xylitol from D-xylose and some factors which affect xylitol yield in *Candida guilliermondii*," *J. Ind. Microbiol.* 3:241-251, Elsevier Science Publishers, Amsterdam (1988).

Beggs, J.D., "Transformation of yeast by a replicating hybrid plasmid," *Nature* 275:104-109, Macmillan Publishers Ltd, London (1978).

Boeke, J.D. et al., "A positive selection for mutants lacking orotidine-5'-phosphate decarboxylase activity in yeast: 5-fluoro-orotic acid resistance," *Mol. Gen. Genet.* 197:345-346, Springer-Verlag, New York (1984).

Broach, J.R. et al., "Transformation in Yeast: Development of a Hybrid Cloning Vector and Isolation of the CAN1 Gene," *Gene* 8:121-133, Elsevier/North-Holland, Amsterdam (1979).

Das, S. and Hollenberg, C.P., "A High-Frequency Transformation System for the yeast *Kluyveromyces lactis*," *Curr. Genet.* 6:123-128, Springer-Verlag (1982).

Fletcher, T.S. and Kwee, I.L., *S. cerevisiae* transketolase gene, complete CDS., GenBank Accession No. M63302 (Mar. 1991).

Flores, N. et al., "Pathway Engineering for the Production of Aromatic Compounds in *Escherichia coli*," *Nature Biotechnol.* 14:620-623, Nature Publishing Co., New York (May 1996).

Gatignol, A. et al., "Cloning of *Saccharomyces cerevisiae* promoters using a probe vector based on phleomycin resistance," *Gene* 91:35-41, Elsevier/North-Holland, Amsterdam (1990).

Gong, C.-S. et al., "Conversion of Pentoses by Yeasts," *Biotechnol. Bioengineer.* 25:85-102, Wiley, New York (1983).

Gong, C.-S. et al., "Quantitative Production of Xylitol from D-Xylose by a High-Xylitol Producing Yeast Mutant *Candida tropicalis* HXP2," *Biotechnol. Lett.* 3:125-130, Chapman and Hall (Nov. 1981).

Haahtela, K. et al., "Nitrogenase Activity (Acetylene Reduction) of Root-Associated, Cold-Climate *Azospirillium*, *Enterobacter*, *Klebsiella*, and *Pseudomonas* Species During Growth on Various Carbon Sources and at Various Partial Pressures of Oxygen," *Appl. Environ. Microbiol.* 45(2):563-570, American Society for Microbiology, Washington D.C. (1983).

Haas, L.O.C. et al., "Development of an Integrative DNA Transformation System for the Yeast *Candida tropicalis*," *J. Bacteriol.* 172(8):4571-4577, American Society for Microbiology, Baltimore, MD (1990).

Hagedorn, J. and Ciriacy, M., "Isolation and characterization of *xyl* mutants in a xylose-utilizing yeast, *Pichia stipitis*," *Chem. Abstr.* 111:418, American Chemical Society, Easton, PA, Abstract No. 228807q (1989).

Hagedorn, J. and Ciriacy, M., "Isolation and characerization of *xyl* mutants in a xylose-utilizing yeast, *Pichia stipitis*," *Curr. Genet.* 16:27-33, Springer International, New York (1989).

Hallborn, J. et al., "Xylitol Production by Recombinant *Saccharomyces cerevisiae*," *Bio/Technol.* 9:1090-1095, Nature Publishing Co., New York (Nov. 1991).

Hattori, K. and Suzuki, T., "Microbiol Production of D-Arabitol by *n*-Alkane-grown *Candida tropicalis*," *Agr. Biol. Chem.* 38(10):1875-1881, Agricultural Chemical Society of Japan, Tokyo (1974).

Ho, N.W.Y. and Chang, S.-F., "Cloning of yeast xylulokinase gene by complementation of *E. coli* and yeast mutations," *Enzyme Microb. Technol.* 11:417-421, IPC Science and Technology Press, Guildford, England (1989).

Holligan, P.M. and Jennings, D.H., "Carbohydrate Metabolism in the Fungus *Dendryphiella salina*: I. Changes in the Levels of Soluble Carbohydrates During Growth," *New Phytol.* 71:569-582, Academic Press, New York (1972).

Ingram, J.M. and Wood, W.A., "Enzymatic Basis for D-Arabitol Production by *Saccharomyces rouxii*," *J. Bacteriol* 89(5):1186-1194, American Society for Microbiology, Baltimore, MD (1965).

Ito, H. et al., "Transformation of Intact Yeast Cells Treated with Alkali Cations," *J. Bacteriol.* 153(1):163-168, American Society for Microbiology, Baltimore, MD (1983).

James, A.P. et al., "Genetic and Biochemical Characterization of Mutations Affecting the Ability of the Yeast *Pachysolen tannophilus* To Metabolize D-Xylose," *Appl. Environ. Microbiol.* 55(11):2871-2876, American Society for Microbiology, Washington D.C. (1989).

Jearnpipatkul, A. et al., "Factors encoded by and affecting the holding stability of yeast plasmid pSR1," *Mol. Gen. Genet.* 206:88-94, Springer-Verlag, New York (1987).

Jeffries, T.W., et al., "Genetic Engineering of Xylose Fermentation in Yeast," http://calvin.biotech.wisc.edu/jeffries/bioprocessing/xoferm/xoferm.html, pp. 1-10 (printed Nov. 9, 2000).

Kötter, P. et al., "Isolation and characterization of the *Pichia stipitis* xylitol dehydrogenase gene, *XYL2*, and construction of a xylose-utilizing *Saccharomyces cerevisiae* transformant," *Curr. Genet.* 18:493-500, Springer International, New York (1990).

Lee, H. et al., "Effect of biotin limitation on the conversion of xylose to ethanol and xylitol by *Pachysolen tannophilus* and *Candida guilliermondii*," *Enzyme Mircob. Technol.* 10:81-84, IPC Science and Technology Press, Guildford, England (1988).

Lewis, D.H. and Smith, D.C., "Sugar Alcohols (Polyols) in Fungi and Green Plants: I. Distribution, Physiology and Metabolism," *New Phytol.* 66:143-184, Academic Press, New York (1967).

Loftus, T.M., et al., "Isolation, Characterization, and Disruption of the Yeast Gene Encoding Cytosolic NADP-specific Isocitrate Dehydrogenase," *Biocehmistry* 33:9661-9667, American Chemical Society, Washington D.C. (Aug. 1994).

Lopes, T.S. et al., "High-copy-number integration into the ribosomal DNA of *Saccharomyces cerevisiae*: a new vector for high-level expression," *Gene* 79:199-206, Elsevier/North-Holland, Amsterdam (1989).

Loviny, T. et al., "Ribitol dehydrogenase of *Klebsiella aerogenes*," *Biochem. J.* 230:579-585, London Portland Press On Behalf Of The Biochemical Society, London (1985).

Mahler, H.R. and Cordes, E. H., "Biological Chemistry," Harper & Row, Inc., New York, NY, pp. 448-454 (1966).

Maniatis, T. et al., "Construction of Genomic Libraries," in: *Molecular Cloning: A Laboratory Manual*, Cold Spring Harbor Laboratory Press, Cold Spring Harbor, NY, pp. 269-294 (1982).

Nasoff, M.S. et al., "DNA sequence of the *Escherichia coli* gene, *gnd*, for 6-phosphogluconate dehydrogenases," *Gene* 27:253-264, Elsevier/North-Holland, Amsterdam (1984).

Nogae, I. and Johnston, M., "Isolation and characterization of the *ZWF1* gene of *Saccharomyces cerevisiae*, encoding glucose-6-phosphate dehydrogenase," *Gene* 96:161-169, Elsevier/North-Holland, Amsterdam (1990).

Onishi, H. and Suzuki, T., "Microbial Production of Xylitol from Glucose," *Appl. Microbiol.* 18(6):1031-1035, American Society for Microbiology, Washington D.C. (1969).

Ørskov, I., Genus V. *Klebsiella* Trevisan 1885, 105[AL], Entry from *Bergey's Manual of Systematic Bacteriology*, vol. 1, Kreig, N.R. et al., eds., Williams & Wilkins, Baltimore, pp. 461-465 (1984).

Ostanin, K., et al., "Cloning and Characterization of a *Saccharomyces cerevisiae* Gene Encoding the Low Molecular Weight Protein-tyrosine Phosphatase," *J. Biol. Chem.* 270:18491-18499, American Society for Biochemistry and Molecular Biology, Inc., Baltimore, MD (Aug. 1995).

Penttila, M. and Enari, T-M, "Genetic Engineering of Industrial Yeasts," In: *Biotechnology—Current Progress*, Eds P.N. Cheremisinoff & L.M. Ferrante, vol. 1, Technomic Publishing Co., Inc., Lancaster, pp. 173-202 (May 1991).

Rothstein, R.J., "One-Step Gene Disruption in Yeast," *Meth. Enzymol.* 101:202-211, Academic Press Inc., New York (1983).

Sanz, P., et al., "Molecular Characterization of a Gene That Confers 2-Deoxyglucose Resistance in Yeast," *Yeast* 10:1195-1202, John Wiley, Chichester NY (Sep. 1994).

Sarthy, A.V. et al., "Expression of the *Escherichia coli* Xylose Isomerase Gene in *Saccharomyces cerevisiae*," *Appl. Environ. Microbiol.* 53(9):1996-2000, American Society for Microbiology, Washington D.C. (1987).

Sonenshein, L., et al., eds., in *Bacillus subtilis and other Gram-Positive Bacteria*, American Society for Microbiology, p. 173, (Apr. 1993).

Speth, J.L. and Niederpruem, D.J., "Enzyme Activities Associated with Arabitol and Mannitol Biosynthesis and Catabolism in *Schizophyllum commune*," *Arch Microbiol.* 107:81-86, Springer-Verlag, Berlin, Germany (1976).

Stevis, P.E. et al., "Cloning of the *Pachysolen tannophilus* Xylulokinase Gene by Complementation in *Escherichia coli*," *Appl. Enviorn. Microbiol* 53(12):2975-2977, American Society for Microbiology, Washington D.C. (1987).

Stevis, P.E. and Ho, N.W.Y., "Construction of Yeast Xylulokinase Mutant by Recombinant DNA Techniques," *Appl. Biochem. Biotechnol.* 20/21:327-334, Humana Press, Clifton NJ (1989).

Sugihara, K. et al., "Ribosomal DNA Plasmid Isolated from *Zygosaccharomyces bailii* and Its Use for Constructing Yeast Vectors Effective for Intergeneric Gene Transfer," *Agric. Biol. Chem.* 50(6):1503-1512, Agricultural Chemical Society of Japan, Tokyo Japan (1986).

Takuma, S. et al., "Isolation of Xylose Reductase Gene of *Pichia stipitis* and Its Expression in *Saccharomyces cerevisiae*," *Appl. Biochem. Biotechnol.* 28/29:327-340, Humana Press, Clifton NJ (May 1991).

Thomas, D. et al., "Identification of the structural gene for glucose-6-phosphate dehydrogenase in yeast. Inactivation leads to a nutritional requirement for organic sulfur," *EMBO J.* 10(3):547-553, IRL Press Limited, Oxford, England (Mar. 1991).

Toh-E, A. et al., "2-μm DNA-Like Plasmids in the Osmophilic Haploid Yeast *Saccharomyces rouxii*," *J. Bacteriol.* 151(3):1380-1390, American Society for Microbiology, Baltimore MD (1982).

Toh-E, A. et al., "Plasmids Resembling 2-μm DNA in the Osmotolerant Yeasts *Saccharomyces bailii* and *Saccharomyces bisporus*," *J. Gen. Microbiol.* 130:2527-2534, Reading Society For General Microbiology, Reading UK (1984).

Ushio, K. et al., "Construction of a Host-Vector System in the Osmophilic Haploid Yeast *Zygosaccharomyces rouxii*," *J. Ferment. Technol.* 66(5):481-488, Society of Fermentation Technology, Osaka, Japan (1988).

Watson, J.D., "The Genetic Code," in: *Molecular Biology of the Gene, 3rd Edition*, W.A. Benjamin, Inc., Menlo Park, CA, pp. 347-377 (1976).

Williamson, W.T. and Wood, W.A., "D-Ribulose 5-Phosphate 3-Epimerase," *Meth. Enzymol.* 9:605-608, Academic Press Inc., New York (1966).

Wood, W.A. et al., "Ribitol and D-Arabitol Utilization by *Aerobacter aerogenes*," *J. Biol. Chem.* 236(8):2190-2195, American Society of Biological Chemists, Inc., Baltimore MD (1961).

*Zygosaccharomyces rouxii* (Boutroux) Yarrow, Entry from "The Yeasts, A Taxonomic Study," van Rij, K., ed., Elsevier Science, Amsterdam, pp. 462-465 (1984).

Derwent English language abstract for Document No. AN1, FR 2 641 545, Derwent World Patents Index Accession No. 1990-262986/199035.

Derwent English language abstract for Document No. AL2, DE 40 09 676, Derwent World Patents Index Accession No. 1991-296506/199141.

Co-Pending U.S. Appl. No. 08/790,585, Harkki et al., filed Jan. 29, 1997.

Derwent English language abstract for Document No. AP2, FR 2 762 011, Derwent World Patents Index Accession No. 1999-012121.

Derwent English language abstract for Document No. AL3, FR 2 772 788, Derwent World Patents Index Accession No. 1999-421845.

* cited by examiner

Fig. 10

MANUFACTURE OF FIVE-CARBON SUGARS AND SUGAR ALCOHOLS

This applications is a continuation-in-part of international application number PCT/FI01/00051, filed Jan. 22, 2001 pending, and a continuation-in-part of U.S. application Ser. No. 09/488,581, filed Jan. 21. 2000, now abandoned, which is a continuation-in-part of U.S. application Ser. No. 08/790, 585, filed Jan. 29, 1997, now U.S. Pat. No. 6,723,540, which is a continuation of U.S. application Ser. No. 08/368,395, filed Jan. 3, 1995, issued as (U.S. Pat. No. 5,631,150), which is a continuation of U.S. application Ser. No. 08/110,672, filed Aug. 24, 1993, abandoned, which is a continuation-in-part of U.S. application Ser. No. 07/973,325, abandoned, the contents of each of which are fully incorporated herein by reference.

BACKGROUND OF THE INVENTION

1. Field of the Invention

The present invention relates to the methods of manufacturing five-carbon aldo- and keto-sugars and sugar alcohols by fermentation in recombinant hosts. Especially, the invention is directed to recombinant hosts that have been engineered to enhance the production of the pentose phosphate pathway intermediates, or the production of one or more of xylitol, D-arabitol, D-arabinose, D-lyxose, ribitol, D-ribose, D-ribulose, D-xylose, and/or D-xylulose, and to methods of manufacturing the same using such hosts.

2. Background of the Invention

Five-carbon sugars and five-carbon sugar alcohols have numerous uses as sweeteners. For example, xylitol is widely used as a non-cariogenic alternative sweetener. D-ribulose and D-xylulose, as well as sugar alcohols other than xylitol, also have potential as sweeteners in the form of free monosaccharides or as components of oligosaccharides. In that regard, glucosyl-xylulose, a close structural analog of sucrose, can be easily synthesized from sucrose and D-xylulose (Kitaoka, K., et al., *Oyo Toshitsu Kagaku* 41(2): 165–72 (1994)).

Five-carbon sugars and five-carbon sugar alcohols are also useful for the organic and enzymatic synthesis of pharmaceuticals, functional food ingredients, etc. D-arabinose and D-lyxose are both structurally very close to D-ribose (the natural sugar constituent of nucleosides/nucleotides) and are components of many drugs and drug formulations.

Five carbon sugars and sugar alcohols are useful as carbon sources for the growth of microorganisms such as bacteria and fungi. Additionally, they are useful as biochemical reagents in laboratory assays of the enzymes that use such five carbon sugars and sugar alcohols as substrates, and as standards in the chromatographic analysis of sugars and sugar alcohols.

A sugar is said to be "naturally produced" if it is capable of being enzymatically synthesized by a non-recombinant microbial or animal host. The precursors of naturally produced five-carbon sugars and their corresponding alcohols are often the pentose phosphate pathway (PPP) sugar intermediates. These intermediates, in their 5-phosphorylated or unphosphorylated form, are valuable in and of themselves as chemical precursors of other various useful compounds. These include, for example, nucleotides and riboflavin (derived from the PPP metabolite D-ribose 5-phosphate), and folate, ubiquinone as well as various aromatic amino acids (derived from the PPP metabolite D-erythrose 4-phosphate). These amino acids are in turn precursors for flavonoids and alkaloids. Consequently, methods and hosts that increase the conversion of a raw material such as a hexose sugar into a desired PPP sugar intermediate such as ribose-5-P, ribulose-5-P or xylulose-5-P, and thus also enhance production of a desired downstream metabolite, would be of significant economical value. These compounds can be extracted or isolated or used in vivo or in vitro as is or as precursors in further metabolic/or chemical reactions to manufacture useful products.

U.S. Pat. No. 5,798,237 (Picataggio, S. K. et al.) reports a recombinant *Lactobacillus* that has been genetically engineered with xylose isomerase and xylulokinase genes to impart the ability to ferment lignocellulosic biomass that contains xylose to lactic acid.

Jeffries et al. have reported the genetic engineering of xylose fermentation in yeast in order to provide for the efficient production of ethanol from xylose. Jeffries, T. W. et al., "*Genetic Engineering of Xylose Fermentation in Yeasts,*" See: calvin.biotech.wisc.edu/jeffries/bioprocessing/xoferm/xoferm.html. Such yeast were identified by their ability to direct carbon flow from the five carbon sugar xylose into the two carbon endproducts alcohol, ethanol, most likely via a pathway that involved the PPP transketolase enzyme acting in a direction that promoted carbon flux away from PPP intermediate accumulation.

Aristidou, A. et al., WO 99/46363 reported that yeast in which the coupling of pyridine nucleotide-linked dehydrogenase reactions had been improved by overexpression of NAD glutamate dehydrogenase or malic enzyme not only exhibited a more efficient production of ethanol from xylose but also had an enhanced production of xylitol from xylose.

However, little has been done with regard to modifying microorganisms in the opposite direction, to redirect carbon flow away from glycolysis or away from ethanol production and into the PPP, with accumulation of PPP intermediates and sugars or sugar alcohols derived therefrom. For example, U.S. Pat. No. 5,281,531 (Miyagawa, K. et al.) reports a method of producing D-ribose in a *Bacillus* host in which the gluconate operon (which encodes the proteins involved in gluconate uptake and metabolism) is partly or wholly modified so as to highly express the gluconate operon. Especially, the gntR gene is deleted or inactivated and the promoter is replaced with another.

D-ribose has been produced from glucose by fermentation with *Bacillus subtilis* (U.S. Pat. No. 3,607,648). Methods for the production of D-xylulose and D-ribulose by fermentation of glucose with some bacteria isolated from nature have also been described (Canadian patent 840981).

U.S. Pat. No. 3,970,522 (Sasajima, K.-I. et al.) report the production of D-ribose in a strain of *Bacillus* that has high 2-deoxyglucose oxidizing activity. In one strain, the *Bacillus* also lacks at least one of transketolase and D-ribulose phosphate 3-epimerase.

Onishi et al. have developed a multi-stage process for the production of xylitol wherein glucose is first fermented with an osmophilic yeast into D-arabitol. Using a different strain D-arabitol is then converted in a second fermentation into D-xylulose. Lastly, using a third strain and in a third fermentation, D-xylulose is reduced to xylitol by fermentation (Onishi, H. and Suzuki, T., *Appl. Microbiol.* 18:1031–1035 (1969)).

Harkki et al. have developed a one-stage fermentation process to convert glucose into xylitol and were the first to suggest directly modifying the PPP for the production of xylitol from glucose in a single host (U.S. Pat. No. 5,631, 150).

Many of the above microbiological methods use strains of bacteria isolated from nature. Most teach no methods of further improving the native abilities the of microorganisms for the production of such sugars or sugar alcohols, or for broadening the spectrum of useful products produced by the fermentation. While the work of Harkki et al. (U.S. Pat. No. 5,631,150) describes some methods of metabolically engineering hosts and methods for the production of xylitol in such hosts, especially by over-expression of the genes of the oxidative branch of PPP, nevertheless, clearly, additional methods for enhancing the metabolic flux through the PPP would be beneficial for production of five carbon sugars as well as any PPP-derived product or product precursor.

SUMMARY OF THE INVENTION

While studying the bioconversion of glucose into xylitol, the inventors have discovered two new pathways for the production of the same. The inventors have also unexpectedly discovered that production of a wide range of five-carbon sugars (both aldoses and ketoses) and sugar alcohols, including xylitol, can be enhanced by using a six carbon sugar such as glucose as a carbon source and microbial hosts in which one or more enzymatic steps of the PPP or other desired enzymatic step, has been genetically eliminated, added, enhanced or otherwise modified by methods of metabolic engineering. Particularly, the invention provides hosts in which there is an increased flux of hexose sugar carbon into the PPP, and an array of methods for the use of the same for the production of a desired sugar or sugar alcohol, in particular xylitol.

In a further embodiment, the invention is directed to a new route for xylitol production in genetically modified hosts by sequentially converting xylulose-5-phosphate to xylitol-1-phosphate (for example, with xylitol 1-phosphate dehydrogenase). Xylitol-1-phosphate is converted to xylitol for example by suitable phosphatase.

In a further embodiment, the invention is directed to the production of arabinitol in genetically modified hosts, such arabinitol being produced from ribulose-5-phosphate using such arabitol-5-phosphate dehydrogenase. The invention is also directed to a new glucose uptake mechanism, which results in the enhancement of flow of glucose and intermediates derived from glucose into the pentose phosphate, by over expression of the *B. subtilis* glcUgdh operon. The invention is directed also to a host, which has been genetically modified to enhance the expression of the glcUgdh operon.

In addition to the genetic modifications, the inventors have discovered fermentation conditions that may be used to further enhance and adjust the spectrum of the five-carbon carbohydrates produced by specific hosts according to the methods of the present invention.

The invention is thus directed to a method of producing five-carbon sugars and sugar alcohols, especially xylitol, as well as other PPP intermediates or products derived from the same, by fermentation of six-carbon sugars (preferably glucose), in a genetically modified and engineered pathway in a single microbial host.

In a further embodiment, the invention is directed to purified and/or isolated polynucleotides encoding a xylitol-phosphate dehydrogenase (XPDH), or arabitol phosphate dehydrogenase (APDH), recombinant vectors and hosts for the expression and maintenance of the same, and to the use of such constructs for xylitol and/or arabitol production in recombinant microbial hosts.

In a further embodiment, the invention is directed to the purified and/or isolated XPDH or APDH protein encoded by such polynucleotides, or preparations containing the same produced by such hosts, and the use of such XPDH or APDH especially for the production of xylitol and/or arabitol.

In a further embodiment, the invention is directed to methods of producing XPDH or APDH using such polynucleotides and the recombinant vectors and hosts of the invention to express the same, especially use in genetically modified hosts for the production of pentose phosphate intermediates, and products derived from the same, such as xylitol or arabitol, respectively.

BRIEF DESCRIPTION OF THE DRAWINGS

FIG. 10. Construction and structure of plasmid pTKT:E1. Oligonucleotides oBS-TKT5 and oBS-TKT3 are SEQ ID Nos. 18 and 19, respectively.

FIG. 24(A and B).

FIG. 25(A and B).

FIG. 27(A and B).

DETAILED DESCRIPTION OF THE PREFERRED EMBODIMENTS

Figure 1:
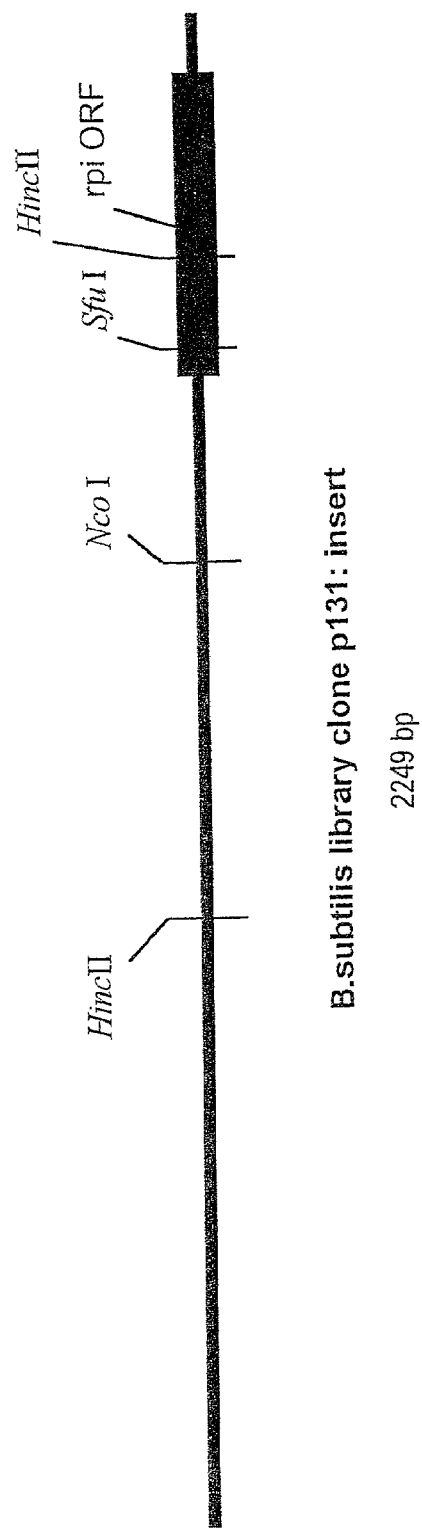
FIG. 1. Restriction map of the *B. subtilis* rpi gene region in the plasmid p131.

Many sugars can exist in both the D-configuration and in the L-configuration. If not expressed stated, and if a listed sugar or sugar alcohol can exist in a D- and an L-configuration, the D-configuration of the listed sugar or sugar alcohol is intended.

The current invention provides methods for producing sugars with a D-configuration, as well as corresponding sugar alcohols, especially 5-carbon sugars and sugar alcohols, and most especially xylitol, by metabolic utilization of glucose or other suitable carbon source(s), and especially by fermentaion of the same. The invention provides methods to improve the flux of carbon sources such as glucose into the pentose phosphate pathway intermediates ribulose-5-P, xylulose-5-P and ribose-5-P and thus to products derived therefrom. The current invention also provides genetically modified hosts for use in such methods, and methods for making such hosts.

According to the invention, the production of a desired sugar or sugar alcohol is achieved by metabolically producing the sugar or sugar alcohol from a precursor in a microbial host that has been genetically modified in a manner that results in an enhanced production of the desired sugar or sugar alcohol when compared to the production of that sugar or sugar alcohol under the same conditions and for the same length of time in the host prior to being genetically modified. The enhanced production may reflect an increased amount or rate of production or increased specific productivity. Such genetic modification can be achieved, for example, by inactivation (random mutagenesis or gene disruption) of one or more genes that encode enzymes that degrade or utilize the desired product, or that otherwise depress or repress the production of the desired product in the host. Such inactivation generally results in the host becoming deficient in the expression product of the targeted gene, or in the expression product of a gene the expression of which is operably linked to the functioning of the inactivated gene. By being "deficient" in a substance such as a protein or enzyme is meant that the host contains reduced levels of that protein or enzyme when compared to the levels the host expressed prior to the inactivation, and includes hosts that completely lack such protein or enzyme as a result of the gene inactivation.

Such genetic modification can also be achieved, for example, by over-expression of one or more other genes that encode proteins and especially enzymes that enhance the amount of the desired product that is made, especially during the cultivation of the genetically modified host. A host can also be genetically modified to contain a combination of modifications that both enhance production and decrease degradation of the desired sugar or sugar alcohol. Additionally, cultivating the genetically modified microbial host under appropriate conditions can be used to further enhance production of the desired sugar or sugar alcohol in a host of the invention.

Examples of sugars (carbohydrates), the synthesis of which can be enhanced according to the methods of the invention, include, in particular, naturally produced sugars that have the D-configuration, especially five carbon aldoses that have the D-configuration. The methods of the invention do not include certain methods for the production of D-ribose (U.S. Pat. Nos. 3,607,648, 3,970,522).

By a "metabolic pathway" is meant a series of two or more enzymatic reactions that take place inside a host cell and in which the product of one enzymatic reaction becomes the substrate for the next chemical reaction. At each step of a metabolic pathway, intermediate compounds are formed and utilized as substrates for a subsequent step. These compounds are called "metabolic intermediates." The products of each step are also called "metabolites." Intermediates in specific pathway can be referred to by the name of the pathway. For example intermediates in the pentose phosphate pathway (PPP) can be called "PPP intermediates."

In its simplest embodiment, the invention is directed to a host that has been genetically modified to be capable of producing enhanced (increased) amounts of one or more specific PPP sugar intermediates for a given period of time as compared to the amount of that sugar intermediate that would have been produced under the same culture conditions prior to such engineering. By a PPP sugar intermediate is intended a sugar that is an intermediate in the PPP and in particular, D-ribose-5-phosphate (D-ribose-5-P), ribulose-5-phosphate (ribulose-5-P), D-xylulose-5-phosphate (D-xylulose-5-P), D-sedoheptulose-7-phosphate (D-sedoheptulose-7-P), D-glyceraldehyde-3-phosphate (D-glyceraldehyde-3-P) and D-erythrose-4-phosphate (D-erythrose-4-P). The invention is also directed to methods of making such hosts, and methods of using such hosts for the production, extraction and purification of one or more of the listed sugars, so as to provide such sugar in a crude cell extract, partially purified (preferably cell free), or isolated form.

In a further embodiment, the invention is directed to a host that has been genetically modified to be capable of producing enhanced amounts of one or more specific sugars or sugar alcohols, especially a five-carbon sugar or sugar alcohol, for which one or more of the PPP sugar intermediates listed above is a metabolic precursor in the recombinant host of the invention, such enhanced amounts being for a given period of time as compared to the amount of that sugar intermediate that would have been produced under the same culture conditions prior to such engineering. Especially, the hosts have been engineered to be capable of producing enhanced amounts of one or more of D-arabitol (also known as D-arabinitol), D-arabinose, D-lyxose, ribitol, D-ribose, D-ribulose, xylitol, D-xylose, and D-xylulose. The invention is also directed to methods of making such hosts, and methods of using such hosts for the production, extraction and purification of one or more of the listed sugars or sugar alcohols, so as to provide such sugar or sugar alcohol in a crude cell extract, partially purified (preferably cell free), or isolated form.

Intermediates of the PPP can be metabolic precursors of other sugars. For example, many microorganisms (bacteria and fungi, including yeast) utilize ribulose-5-P as a precursor for ribulose. A microorganism that possesses or has been engineered to possess the ribulose reductase (NADPH) form of arabitol dehydrogenase can produce D-arabitol from ribulose. Ribulose can also serve as a precursor for D-arabinose (by a pathway that utilizes L-fucose isomerase) and ribitol (via ribitol dehydrogenase). Accordingly, the term "ribulose-5-P derived product" as used herein includes ribulose, ribitol, D-arabitol and D-arabinose and ribitol, and mixtures of the same, but is not restricted to these examples.

Xylulose-5-P can also be a precursor of several important products including xylulose, which in turn is a precursor for D-lyxose (via mannose-isomerase) and D-xylose (via xylose isomerase). Accordingly, the term "xylulose-5-P derived product" as used herein includes xylulose, D-lyxose and D-xylose, and mixtures of the same, but is not restricted to these examples. For example, a strain in which the genetic modifications results in increased relative amounts of xylulose-5-P can be further genetically modified to result in a strain with improved yields of xylulose-5-P derived products such as xylitol. Similarly, a strain that has been modified to have increased amounts of ribose-5-P or an increased flux of carbon to ribose-5-P can be further modified to increase the production of ribose-5-P derived products, and especially the production of nucleotides and riboflavin, or D-erythrose 4-P and products thereof, such as folate, ubiquinone and various aromatic amino acids. Similarly, as described herein for products such as sugar alcohols, production of ribose-5-P derived products in a strain accumulating ribose-5-P or having improved flux of carbon to ribose-5-P can be further improved by genetic modification of the subsequence/downstream metabolic reactions leading to such products.

In a preferred embodiment, new methods for manufacturing D-arabinose, D-lyxose and D-xylose are provided. In an additional preferred embodiment, new methods for production of both of the five-carbon D-ketoses—D-ribulose and D-xylulose as well as all of the five-carbon pentitols that can be derived from D-pentoses, namely, xylitol, D-arabitol and ribitol are provided. Methods for the production of xylitol are an especially preferred embodiment.

The invention also provides methods for changing the spectrum (the relative amount when compared to each other), of the five-carbon carbohydrate products that result from the fermentation of glucose and other carbon sources, especially carbon sources that are metabolically converted into a six carbon sugar intermediate in the glycolytic pathway, and especially in the hosts of the invention, by adjusting the fermentation conditions. Using the methods of the present invention one can obtain, through fermentation of glucose and other six-carbon sugars, enhanced levels of any naturally produced five-carbon sugar or sugar alcohol having the D-configuration or that is derived from sugars or sugar alcohols having such configuration and from an intermediate in the PPP. Especially, D-ribulose, D-ribose, D-xylulose, D-arabinose, D-lyxose, D-xylose, D-arabitol, ribitol and xylitol can be produced, but also other products derived from PPP intermediates can be produced.

The hosts and methods of the present invention may be achieved by combining within a microbial host, a single genetic combination or a combination of several different genetic modifications designed to achieve:
 a) disruption or a decrease of activity of one or more enzymatic or substrate transport steps, especially sugar transport steps;
 b) introduction of one or more new, desired enzymatic or sugar transport activities;
 c) over-expression of one or more desired enzymatic or sugar transport activities that are already present in the host; or
 d) a combination of any of (a) and (b) and (c).

In a preferred embodiment, the host of the invention has been genetically modified to contain a disruption of one or more enzymatic steps in the non-oxidative part of the PPP and/or in one or more enzymatic steps for reactions that indirectly affect carbon flux through the PPP.

The genetic modifications of the current invention focus on genes coding for proteins that affect sugar metabolism, and especially enzymes, involved in several key areas of carbohydrate metabolism. The areas most important in this respect are: the non-oxidative branch of the pentose-phosphate pathway (PPP); the oxidative branch of the PPP; the upper part of the glycolytic (Embden-Meyerhof) pathway (i.e., prior to aldolase), and the prokaryotic sugar uptake system (PTS system). Additionally, various individual metabolic reactions catalyzed by polyol dehydrogenases, aldose isomerases and ketose epimerases and sugar dephosphorylating enzymes can be targeted.

The reactions of the PPP are divided into an oxidative branch, followed by a series of reactions that constitute the non-oxidative branch. The reactions catalyzed by oxidoreductases such as glucose-6-phosphate dehydrogenase and 6-phosphogluconate dehydrogenase make up the oxidative branch. Glucose-6-phosphate dehydrogenase catalyzes the conversion of glucose-6-phosphate to 6-glucono-lactone-6-phosphate, which is chemically (and enzymatically in some hosts) rapidly converted to 6-phosphogluconate. 6-Phosphogluconate dehydrogenase then catalyzes the conversion of 6-phosphogluconate to ribulose-5-P.

The nonoxidative branch of the PPP is characterized by the catalytic activity of (1) ribose-5-P isomerase (also known as ribulose-5-P isomerase), (2) ribulose-5-P 3-epimerase, (3) transketolase and (4) transaldolase. In the nonoxidative branch of the PPP, ribulose-5-P is isomerized to ribose-5-P by ribose-5-P isomerase. Ribulose-5-P is also epimerized to xylulose-5-P by the action of ribulose-5-P 3-epimerase. Transketolase converts ribose-5-P and xylulose-5-P into glyceraldehyde-3-P and sedoheptulose-7-P. Transaldolase takes glyceraldehyde-3-P and sedoheptulose-7-P and converts them to fructose-6-phosphate and erythrose-4-P. Transketolase then utilizes erythrose-4-P and xylulose-5-P as substrates and converts them into glyceraldehyde-3-P and fructose-6-P.

A host that has been modified to have one or more genetic modifications in the non-oxidative branch of the pentose-phosphate pathway is an especially preferred host of the present invention. Preferably, one or more of the enzymes of the non-oxidative branch of the PPP are inactivated so that carbon flow through the non-oxidative branch of the PPP is disrupted at a site that it is desired to block in order that the carbon flow can be redirected into the production of a desired compound. Thus the native carbon flow through the non-oxidative branch of the PPP is lessened or completely stopped in such hosts. This is preferably achieved by disruption of one of more of the genes encoding ribulose-5-P isomerase, ribulose-5-P 3-epimerase, transketolase, and transaldolase. As discussed in detail below, such disruption can be achieved either by random chemical mutagenesis and selection, or by targeted mutagenesis techniques such as gene disruption.

For the enhanced production of ribulose-5-P, and ribulose-5-P-derived products, the disruption or inactivation of the ribose-5-P isomerase gene is especially preferred. Alternatively, or, in addition, the disruption or inactivation of the ribulose-5-P 3-epimerase gene is highly desirable. When such a host is cultivated on a six carbon sugar such as glucose, or a sugar that is converted into glucose or a six carbon sugar metabolite thereof such as glucose-6-P, carbon flow into the PPP is trapped or bottlenecked at the ribulose-5-P step, thus resulting in the accumulation of that intermediate, and in an increased carbon flow from ribulose-5-P into ribulose-5-P-derived products in those hosts that are capable of producing the same. By a production that is "trapped" or "bottlenecked" at a specific step, is meant that the rate of utilization or degradation of the compound at that step by the host is less than the rate of synthesis of that compound, so that the amount of the compound is increased relative to hosts that do not contain this modification, when grown under the same conditions.

For the enhanced production of xylulose-5-P and xylulose-5-P-derived products, the disruption or inactivation of the gene encoding ribose-5-P isomerase is highly preferred. The gene encoding ribulose-5-P 3-epimerase is preferably either left intact or else additional copies (either homologous or heterologous but preferably homologous copies from the same species) of that gene are introduced, so as to enhance carbon flow into xylulose-5-P. Inactivation of the transketolase gene in addition is especially preferred when constructing a host for the enhanced capacity to produce xylulose-5-P. When such a host is cultivated on a six carbon sugar such as glucose, or a six carbon sugar metabolite thereof such as glucose-6-P, carbon flow into the PPP is trapped or bottlenecked at the xylulose-5-P step, thus resulting in the accumulation of that intermediate, and in an increased carbon flow from xylulose-5-P into xylulose-5-P-derived products in those hosts that are capable of producing the same.

Inactivation of the genes encoding ribose-5-P isomerase and transketolase and/or transaldolase block or otherwise significantly lessen PPP carbon flow out of the PPP in the direction of the glycolytic pathway intermediates. Alternatively, inactivation of the transketolase gene, or in addition, inactivation of the transaldolase gene, even without inactivation of the ribose-5-phosphate isomerase gene can be used to block carbon loss out of the PPP and into the glycolytic pathway at those enzymatic steps, but yet allow for production of ribose-5-P and products derived therefrom.

The result of the gene inactivations discussed above in which ribose-5-P isomerase is inactivated will result in an accumulation of one or both of ribulose-5-P and xylulose-5-P, as compared to the unmodified host, or in an accumulation of one or more metabolic products for which ribulose-5-P or xylulose-5-P are metabolic precursors in their synthesis pathways.

When multiple genes coding for several isoenzymes of transketolase or D-ribose 5-phosphate isomerase are present in the host, as is the case with the transketolase genes of *S. cerevisiae* or the D-ribose 5-phosphate isomerase genes in *E. coli*, then all of the genes encoding those enzymes are preferably inactivated. The gene(s) coding for D-ribose 5-phosphate epimerase may be inactivated or over-expressed depending on the implementation (i.e., whether or not carbon flow into xylulose-5-P is needed). The most highly preferred mode of implementing the current invention is to inactivate all of the D-ribose 5-phosphate isomerase and transketolase genes present in the selected host.

The hosts of the invention can also be designed to over-express one or more desired genes that encode proteins that were already present in the host and that catalyze the inter-conversion of specific five-carbon sugars and sugar alcohols. Alternatively, the hosts of the invention can be designed to express a desired enzymatic activity that the host had previously lacked. Examples of such genes that are targets for introduction and/or over-expression in the hosts and methods of the invention include the genes coding for polyol dehydrogenases such as xylitol dehydrogenase, arabitol dehydrogenase or ribitol dehydrogenase. Similarly, the genes coding for various isomerases and epimerases and that act on neutral sugars are considered to belong to this group. Examples of such isomerases and epimerases are: L-fucose isomerase (Garcia-Junceda E., et al., *Bioorg. Med. Chem.* 3:1349–1355 (1995)), D-mannose isomerase (Allenza, P., et al., *Appl. Biochem. Biotechnol.* 24–25:171–182 (1990)), D-xylose isomerase (e.g., reviewed in Bhosale, S. H., et al, *Microbiol Rev.* 60:280–300 (1996)), ketose 3-epimerase (Ishida, Y., et al., *J. of Fermentation and Bioengineering* 83:529–534 (1997)).

The specific choice of the gene to introduce de novo or to over-express will depend on the particular implementation of the present invention. For example, if xylitol is the target product, and the host produces xylulose, then the xylitol dehydrogenase gene needs to be expressed in the host cells during fermentation or at least during the production cycle (if separate from the fermentation step). If D-xylose is the target product, and the host produces xylitol, then one of the many known D-xylose isomerase genes has to be expressed during fermentation or during the production cycle.

Thus, in one embodiment, a host of the invention is used for the production of xylitol by a method comprising
  (A) growing a recombinant host on a carbon source other than D-xylose, D-xylulose, mixtures of D-xylose and D-xylulose, and polymers and oligomers containing D-xylose or D-xylulose as major components;
  (B) producing xylitol in said host by conversion of one or more pentose phosphate pathway intermediates into said xylitol by a metabolic pathway in which arabitol is not an intermediate; and
  (C) recovering said xylitol that is produced in part (B).

In a preferred embodiment, such pathway utilizes ribulose-5-phosphate as an intermediate metabolite in the production of the xylitol. In an especially preferred embodiment, such pathway utilizes ribulose-5-phosphate, xylulose-5-P and xylitol-1-P as intermediate metabolites in the production of the xylitol. Xylitol-1-P is also known as xylitol-5-P.

Alternatively, in another especially preferred embodiment, such pathway utilizes (1) ribulose-5-P, (2) ribulose, and (3) at least one of xylulose and xylose as intermediate metabolites in the production of the xylitol.

Thus, in a preferred embodiment, xylitol is produced in a host of the invention by a pathway such as that exemplified in Example 24 in which:
  a) ribulose-5-P is epimerized to xylulose-5-P by an enzyme such as ribulose-5-P 3-epimerase;
  b) xylulose-5-P is reduced to D-xylitol-5-phosphate D-xylitol-1-phosphate) by an enzyme such as xylitol-5- phosphate dehydrogenase (also known as xylitol-1-phosphate dehydrogenase or simply XPDH) or ribitol-phosphate dehydrogenase; and c) D-xylitol-5-phosphate D-xylitol-1-phosphate) is dephosphorylated into xylitol by a sugar phosphatase.

Hosts that accumulate xylulose-5-P and into which a gene that expresses an enzyme capable of reducing xylulose-5-P to xylitol-5-P such as xylitol-5-phosphate dehydrogenase are especially preferred.

Reference to D-xylitol-5-phosphate-is understood in the art to be the same compound as L-xylitol-1-phosphate, and vice versa, and accordingly, as used herein they are interchangeable. Additionally, it is understood in the art that reference to enzymes, such as xylitol-5-phosphate dehydrogenase, that make or utilize xylitol-5-P, is understood to also refer to and to be the same as an enzyme named xylitol-1-phosphate dehydogenase or simply XPDH, and that such names are interchangeable.

Alternatively, and in another preferred embodiment, xylitol is produced in a host by a route exemplified in Example 9 in which ribulose-5-phosphate is dephosphorylated to ribulose (for example with ribulose-5-P phosphatase); ribulose is epimerized to xylulose (for example with tagatose epimerase); and xylulose is either reduced to xylitol (for example with xylitol dehydrogenase) or, alternatively, xylulose is first partly isomerized to xylose and then xylulose and xylose are reduced to xylitol.

Thus, the pathways and enzymatic reactions that are involved in the conversion of glucose to xylitol include a xylitol-phosphate pathway, a xylitol-dehydrogenase pathway, a tagatose epimerase pathway and an arabitol pathway.

In the xylitol-phosphate pathway, ribulose-5-P is converted into xylulose-5-P. Xylulose-5-P is then converted into xylitol-5-P, which is converted into xylitol.

In the xylitol-dehydrogenase pathway, ribulose-5-P is converted into xylulose-5-P. Xylulose-5-P is converted into xylulose, which is converted into xylitol.

In the tagatose epimerase pathway ribulose-5-P is converted into ribulose. Ribulose is converted into xylulose, which is then converted into xylitol.

In the arabitol pathway, arabitol is converted into xylulose, which is converted into xylitol.

D-mannose isomerase is known to catalyze the interconversion of D-xylulose and D-lyxose (Stevens, F. J., et al., *J. Gen. Microbiol.* 124:219–23 1981)). Thus, by expressing a gene for mannose isomerase in a D-xylulose producing host one would be able to obtain D-lyxose as a product of glucose fermentation.

L-fucose isomerase is known also to convert D-ribulose into D-arabinose (Bartkus, J. M., et al., *J. Bacteriol.* 165:704–709 (1986)). Expression of a suitable gene (e.g., the *E. coli* fucI, GenBank accession number U2958 1) in a D-ribulose-producing host of the invention (e.g., *B. subtilis* GX2) would result in a host that could convert D-glucose into D-arabinose via D-ribulose.

In designing the hosts of the invention, it is of importance to also keep in mind the early steps of hexose metabolism, including the sugar uptake systems, the upper part of the glycolytic pathway (that is, at some point between hexokinase/glucokinase and aldolase action) and the oxidative branch of the PPP. Genetic modifications in those areas are not required for the implementation of this invention. However, the hosts of the invention can be genetically modified to contain one or more modifications in such areas so as to maximizing the carbon flow into the oxidative branch of the PPP and thus into the non-oxidative branch of the PPP, thus resulting in a further improvement in the yields of the desired fermentation products.

More specifically, a disruption in the gene that encodes an enzyme that regulates the distribution of carbon flow between the glycolytic pathway and the PPP is highly desirable in the hosts of the invention. Such a gene can encode an enzymatic activity present in the upper part of the glycolytic pathway (that is, prior to the triose phosphate isomerase step). Disruption of such a gene and lack of the enzyme encoded thereby prevents carbon flow out of the hexose-phosphate pool through the glycolytic pathway, which leads to accumulation of the six carbon glycolytic metabolites and especially, of glucose 6-phosphate (glucose-6-P), which can be directed to the oxidative branch of the PPP.

Glycolytic enzymes that are targets for disruption or reduction in activity prior to the triose phosphate isomerase step are those subsequent to the synthesis of glucose-6-phosphate, and in particular, glucose 6-phosphate isomerase (also known as phosphoglucoisomerase), phosphofructokinase and aldolase. The preferred target of such modification is the glucose 6-phosphate isomerase gene and/or phosphofructokinase gene. Since microbial strains containing reduced or lacking activity of glucose-6-phosphate isomerase gene tend to grow poorly on glucose, fructose may be used as a co-substrate during fermentation. Alternatively the fermentation may be done in two phases wherein growth of the production strain is achieved on fructose-enriched medium and glucose is fed only during the production phase in which the desired PPP sugar or product derived therefrom is accumulated. Reduced activity of the glucokinase or hexokinase genes are not desired when it is desired to enhance flux into the oxidative branch of the PPP as these enzymes produce glucose-6-P, the substrate for glucose-6-P dehydrogenase, the first enzyme in the oxidative branch of the PPP. Alternatively, the intracellular activity of the glycolytic enzymes may be reduced by mutation, by changing the promoter and/or by the use of chemical inhibitors, and the desired mutant selected based upon enzyme assay or substrate growth screening assays. In vitro enzymatic assays for characterizing the presence or absence of each of the glycolytic enzymes are well known in the art.

An alternative/complementary way of achieving increased carbon flow into the PPP is the over-expression of a gene coding the first enzyme of the oxidative branch of PPP: glucose 6-phosphate dehydrogenase. Particularly, such genes from heterofermentative lactic acid bacteria (e.g., *Leuconostoc mesenteroides*) or *Zymomonas mobilis* (GenBank accession number M60615) would be suitable because of their reduced sensitivity towards allosteric inhibition typical of many glucose 6-phosphate dehydrogenases (Sugimoto S. & Shio, I., *Agric. Biol. Chem.* 51:101–108 (1987)). Over-expression of a gene coding for the second enzyme of the oxidative branch of PPP, 6-phosphogluconate, is also considered to be within the scope of current invention. High activity of this enzyme can prevent the cells from accumulating 6-phosphogluconate and excreting gluconic acid into the culture medium.

Another group of genes that may advantageously be inactivated in order to practice the present invention are those that encode enzymes or proteins that control sugar uptake by the host cells. In bacterial hosts, inactivation of the wild-type sugar-uptake system (known as PTS system) by mutation coupled with the introduction of an alternative (kinase-based) sugar uptake system may be used for improving the overall metabolic and energetic balance of the cells. In hosts prone to the phenomenon called "cofactor imbalance" inactivation of enzymes competing for cofactors (typically, NADP$^+$) with the enzymes of the oxidative branch of PPP is also considered within the scope of this invention. Cofactor imbalance is discussed further below.

The set of genes that it is advantageous to express or to over-express within the microbial host of the invention will thus depend on the specific implementation of the present invention. Over-expression of the genes of the oxidative branch of the PPP, and especially glucose 6-phosphate dehydrogenase and 6-phosphogluconate dehydrogenase, is useful although not absolutely necessary in most implementations. In certain hosts (e.g., many yeasts) in which the cofactor imbalance phenomenon may occur, expression of heterologous or homologous transhydrogenases may be advantageous. Alternatively, the effect of the transhydrogenases can also be achieved by providing the host with genes encoding a pair of dehydrogenases that use different cofactors (one NADPH and the other NAD) and that catalyze otherwise identical reactions, preferably in the cytosol.

Over-expression of the glucokinase or hexokinase enzymes is particularly useful when this invention is implemented in bacterial hosts and their native PTS-based sugar uptake system is inactivated. In some hosts (over-) expression of homologous or heterologous sugar-phosphate phosphatase may be needed or otherwise desired to achieve significant conversion of five carbon sugar phosphates into corresponding neutral (i.e., dephosphorylated) sugars. A number of other genes, including the genes coding for xylitol dehydrogenase, D-arabitol dehydrogenase, ribitol dehydrogenase, L-fucose isomerase, D-mannose isomerase, D-xylose isomerase, ketose 3-epimerase etc. may be used in specific implementations of the present invention.

In addition to the specific genetic modifications aiming at reducing or enhancing the activity of particular known enzymes within the microbial host such as the modifications described above, mutations acting via unknown enzymes/mechanisms may be used for implementing this invention. For, example, the spectrum of the fermentation products of a pentose/pentulose-producing recombinant host may be changed very strongly and specifically by applying certain mutant selection/screening protocols as revealed by the present invention.

A modification of the glucose uptake system is advantageous when this invention is implemented in a bacterial host that takes up and phosphorylates glucose via the PTS system. The functioning of the PTS system requires a continuous supply of phosphoenolpyruvate—a product of the glycolytic pathway. If the PTS system is replaced with a glucokinase- or hexokinase-based glucose uptake and phosphorylation system, then ATP rather than phosphoenolpyruvate would supply the energy for glucose uptake and phosphorylation. Unlike phosphoenolpyruvate, ATP can be replenished via the respiratory chain, utilizing NADPH generated by the oxidative branch of PPP. Thus, such a system would provide a much better energy balance for those microbial host cells of the invention that convert hexose-phosphates into pentose phosphates via the PPP and consequently higher yields of the desired five-carbon sugars would result. The technology for replacement of a PTS-based glucose uptake and phosphorylation system with a kinase-based system is known in the art (Flores, N., et al., *Nature Biotechnology* 14:620–623 (1996)). The invention is also directed to a modified glucose uptake mechanism, which results in the enhanced flow of glucose and intermediates derived from glucose into the pentose phosphate, by over expression of the *B. subtilis* glcUgdh operon. Such hosts are especially useful when it is desired to utilize a host that produces an enhanced level of one or more pentose phophate shunt intermediates, for example, in the methods of making xylitol as described herein. The invention is also directed to a host, which has been genetically modified to enhance the expression of the glcUgdh operon.

In hosts that have a very low or no transhydrogenase activity and that lack the machinery for re-oxidation of NADPH via the respiratory chain, the activity of the PPP may create a phenomenon sometimes referred to as "cofactor imbalance." Cofactor imbalance causes a decrease of the carbon flow though the oxidative branch of the PPP because the supply of intracellular NADP$^+$ for glucose 6-phosphate dehydrogenase and 6-phosphogluconate dehydrogenase becomes limiting. In this case, additional genetic modifications that decrease the demand for NADP$^+$ in other parts of cellular metabolism or that allow the cell to re-oxidize NADPH, for instance, by NAD$^+$ (NADH is re-oxidized through the respiratory chain much more efficiently than NADPH) can be engineered into the hosts for the practice of the methods of this invention.

Thus, expression of a transhydrogenase gene is useful for increasing the performance of certain hosts of invention as above. Alternatively, a pair of dehydrogenases acting on the same substrates but using two different cofactors (NADH and NADPH) may be expressed within the host cells. Such a pair effectively acts as a "quasi-transhydrogenase" equilibrating the redox state of both NADH-NAD$^+$ and NADPH-NADP$^+$ pools (Aristidou et al., WO 99/46363). A particularly suitable pair of dehydrogenases is NADH- and NADPH-dependent glutamate dehydrogenases. For example, in yeast NADPH-dependent glutamate dehydrogenase (encoded by the GDH1 gene) is expressed at sufficiently high level from the wild type chromosomal gene. Therefore, over-expression of only one gene—a NADH-dependent glutamate dehydrogenase gene (e.g., yeast GDH2 gene (Miller, S. M., et al., *Mol. Cell Biol.* 11:6229–47 (1991); Boles, E., et al, *Eur. J. Biochem.* 217(1):469–77) (1993) is sufficient to alleviate the cofactor imbalance within the host cell (Aristidou et al., WO 99/46363).

The flux through PPP can also be increased by inactivation of cellular enzymes that compete for NADP$^+$ with the enzymes of oxidative branch of PPP. For example, inactivation NADP-dependent citrate dehydrogenase gene IDP2 (Loftus, T. M., et al., *Biochemistry* 33:9661–9667 (1994)) can have a stimulating effect on the metabolic flux through PPP.

Re-oxidation of NADPH can also be accomplished by providing the host cell with a suitable co-substrate and an enzyme capable of reducing this co-substrate using NADPH. A typical example of such co-substrate is xylose, that may be reduced to xylitol by a NAD(P)H-dependent xylose reductase. Genes encoding suitable xylose reductases have been cloned from a number of microorganisms (Amore, R., et al., *Gene* 109(1):89–97 (1991); Billard, P., et al. *Gene* 162(1):93–97 (1995)).

One more solution to the problem of decreased flux through the oxidative branch of the PPP under conditions of cofactor imbalance is to express within a host of invention a heterologous gene coding for glucose 6-phosphate dehydrogenase and/or 6-phosphogluconate dehydrogenase that is capable of using NAD$^+$ as the cofactor. Suitable examples of genes coding for glucose 6-phosphate dehydrogenases with such properties are zwf genes from *Pseudomonas aeruginosa* and *Leuconostoc mesenteroides* (Ma, J. F., et al., *J. Bacteriol.* 180 (7):1741–1749; Lee, W. T., et al., *J. Biol Chem.* 266:13028–13034(1991)). Also, NAD$^+$-specific 6-phosphogluconate dehydrogenases that would be useful for practicing this invention are known (Ohara, H., et al., *Bioschi. Biotech. Biochein.* 60(4):692–693 (1996)).

A "reverse" type of cofactor imbalance may occur in microbial cells when reduced rather than oxidized form of cofactor (NADH) becomes limiting. Within the scope of this invention, this problem typically occurs when a 5-carbon sugar alcohol is the target product that is formed by enzymatic reduction of the corresponding 5-carbon keto-sugar. In this case, inactivation of the wild type genes coding for enzymes that compete for NADH is useful. A particularly suitable example in yeast is the pair of NADH-dependent dehydrogenases GPD1 and GPD2 involved in glycerol production (Ansell R., et al., *EMBO J.* 16:2179–2187 (1997)). In *B. subtilis*, inactivation of the acetoin reductase gene would be the preferred genetic modification improving NADH supply for sugar alcohol production.

Another genetic modification which is advantageous for the implementation of the current invention in some hosts (for example, yeast) is (over-) expression of a sugar-phosphate phosphatase gene such as DOG1 gene of yeast *Saccharomyces cerevisiae* (Sanz, P., et al., *Yeast* 10:1195–202 (1994)). This gene is known to encode for a phosphatase active also on 5-carbon sugar phosphates such as ribose 5-phosphate and ribulose 5-phosphate. The inventors have shown that the enzyme is also active towards xylulose 5-phosphate and disclose here that over-expression of DOG1 results in increased accumulation of 5-carbon sugars and corresponding polyols, in particular, ribitol. Another type of phosphatase useful for practicing this invention have been known under the name of "low molecular weight protein-tyrosine phosphatases" (Chernoff, J. and Li, H. C., *Arch. Biochem. Biophys.* 240:135–145 (1985)). The present inventors have unexpectedly discovered that these enzymes are also active on 5-carbon sugar phosphates. Over-expression of the LPT1 gene of *S. cerevisiae* (Ostanin K., et al., *J. Biol. Chem.* 270:18491–18499 (1995)) was found to improve the production of five carbon sugars and sugar alcohols. Other genes of this class suitable for practicing the present invention were isolated from yeast *Zygosaccharomyces rouxii* and are disclosed here. In certain hosts, such as *B. subtilis*, expression of a phosphatase may not be necessary, since, as was discovered by the present inventors, the cells of such hosts readily dephosphorylate a number of five-carbon sugar phosphates including D-ribose 5-phosphate, D-ribulose 5-phosphate and D-xylulose 5-phosphate.

One more type of genetic modification which is useful in practicing this invention is inactivation or reduction of the activity of a gene coding for a kinase which converts the five-carbon sugars into the corresponding sugar phosphates. An example of such a useful genetic modification is the inactivation of the gene encoding xylulokinase. We disclose here that the inactivation of this gene increases the yield of xylulose and the corresponding polyol, xylitol. Analogously, inactivation of the ribulokinase would be useful if ribulose or ribitol are the target products. Also, the genetically modified host can be deficient in pentose sugar kinase, pentulose sugar kinase, or deficient in both.

The spectrum of products, such as five-carbon sugars produced by the recombinant strains of the present invention in many cases may be controlled or further modified by the fermentation conditions. Most importantly, the concentration of dissolved oxygen in the culture medium affects the balance between the ketoses and corresponding sugar alcohols. For example, when certain *B. subtilis* strains of this invention are cultivated under highly aerated conditions they produce pentuloses as the predominant five-carbon sugar products of fermentation. Polyols are the predominant fermentation products under microaerobic conditions.

Besides the genetic methods for the construction of the new recombinant microbial hosts, the current invention provides methods for controlling the product spectrum by adjusting the fermentation conditions of said hosts. For example, according to the invention, the ratio of sugars to the corresponding sugar alcohols that are produced by the host of the invention can be varied in a very wide range by adjusting the aeration of the microbial cultures.

Whether or not the fermentation is optimized for the production of a desired product or selection of products, the carbon source for the fermentation of the hosts in the methods of the invention can be glucose or another six-carbon sugar that is capable of being metabolized by a pathway that has at least some steps in common, that is, overlaps, the glycolytic or PPP pathway for metabolism of glucose. Examples of such other sugars include fructose, and mannose. Also considered to be useful carbon sources within the scope of current invention are oligosaccharides and polysaccharides that comprise such six-carbon sugars, for example sucrose, lactose, maltose, raffinose, inulin, starch, etc. These carbon sources may be used individually or in the form of mixtures, such as, for example, inverted sugar or high-fructose syrup. Pentoses may also be used as a part of the substrate sugar mixture. Within the framework of this invention the role of pentoses is limited to the pentose being used as co-substrates rather than main substrates (e.g., serving as an "electron sink" for the regeneration of $NADP^+$).

In a further embodiment, a host is constructed that expresses or over-expresses XPDH gene, using recombinant XPDH gene sequences. Such sequences have been identified by the inventors in *L. rhamnosus* and *R. halodurans*. Similar sequences from *C. difficile* (SEQ ID NO:51, 52 and 53) would also be useful in this regard. Such hosts are especially useful for the production of xylitol in a pathway in which xylulose-5-P is converted to xylitol-1-P by XPDH, and then the xylitol-1-P is converted to xylitol with a phosphatase. As shown in the examples (Example 28), the culture broth of such strains contained xylitol while xylitol could not be detected in the culture media of control strains.

In another embodiment, arabitol-phosphate dehydrogenase gene has been cloned for the first time, and hosts for the expression of the same have been constructed. The sequence from *E. avium* contains an open reading frame of 352 codons preceded by a typical ribosome binding site (SEQ ID NO:68). The deduced amino acid sequence is presented at SEQ ID NO:69. This enzyme is reversible and converts D-arabitol -5-phosphate to D-xylulose-5-phposphate, and vice versa. Accordingly, the arabitol-phosphate dehydrogenases of the invention can be used in a method of making D-arabitol (CAS No. 488-82-4)(also known as D-arabinitol) by conversion of D-xylulose-5-phposphate into D-arabitol 5-phosphate. This sequence can be used to identify other sequences that can be used, such as SEQ ID NO:70, a sequence originally reported to be a sorbitol dehydrogenase but which is discovered by the present inventors to be an arabitol-phosphate dehydrogenase from *B. halodurans*.

The range of hosts wherein current invention can be implemented covers bacteria and fungi. The fungi is preferably yeast. Particularly, microbial species with a GRAS status such as yeast *Saccharomyces cerevisiae* or Gram-positive bacterium *Bacillus subtilis* are suitable as the hosts of the current invention. Other suitable hosts are: many species of yeast, e.g., those belonging to genera *Saccharomyces, Zygosaccharomycesi, Candida* or *Kluyveromyces*

(e.g. *Zygosaccharomyces rouxii, Candida utilis* or *Kluyveromyces marxianus*), filamentous fungi such as those from genera *Aspergillus, Penicillium* or *Trichoderma* etc. (e.g. *Aspergillus niger, Penicillium roqueforti, Trichoderma reesei*) or bacteria such as various species of *Escherichia, Corynebacterium, Bacillus,* lactic acid bacteria etc. (e.g. *Escherichia coli, Corynebacterium glutamicum, Bacillus amyloliquefaciens, Lactobacillus lactis, Pichia stipitis* and *Neurospora, Mucor* and *Fisarium* species).

The preferred genetic modification technique for implementing current invention is recombinant DNA technology (genetic engineering). This technology is used primarily for two types of tasks. The first type of task is the inactivation of the functional wild type-genes in the selected host. Another, opposite task is to introduce and express heterologous genes coding for enzymes lacking or expressed at an insufficient level in the host of the invention. A variation of this latter task is to over-express homologous genes of the host which are expressed in wild type strains at suboptimal levels.

Targeted inactivation of the wild type genes of the hosts of the invention may be achieved by any method known in the art. For example, anti-sense RNA specific towards the target gene may be produced within the host cells. Mutations in "auxiliary" genes needed for the expression of the target gene, such as transcriptional activators or anti-terminators, etc., may be obtained. A gene inactivation technique based on homologous recombination between a chromosomal wild-type copy of the gene and an in-vitro constructed inactivated copy of the same gene, known as "gene disruption" is the preferred method for the implementation of the "gene inactivation tasks" of the current invention. This technique is well known to those skilled in the art. The preferred way of in-vitro inactivation of the target gene is constructing a plasmid containing a cloned copy of this gene. The coding sequence is subsequently interrupted or part of the coding sequence is substituted with DNA coding for a selectable genetic marker, such as antibiotic resistance gene or a gene complementing an auxotrophic mutation of the host. The plasmid construction or a part thereof is subsequently used to transform the selected host to antibiotic resistance or prototrophy. In addition to the recombinant DNA methods, traditional genetic techniques based on random chemical, radiation-induced or spontaneous mutagenesis followed by selection of the target mutants can also be used.

Expression of heterologous genes or over-expression of homologous genes for the purposes of the present invention may be achieved by a number of methods. The preferred method is to construct in-vitro a so-called "expression cassette" comprising a promoter functional in the selected host followed by the coding area of the gene to be (over-) expressed and a transcription termination signal. Of course, if the native promoter of the gene to be expressed is active in the selected host, the unmodified gene comprising both the coding sequence and the flanking 5' and 3'-areas may without any modifications represent such a "cassette." The expression cassette may then be introduced into the host of the invention as a part of a multi-copy plasmid that is stably maintained by the host or integrated into the chromosome.

Many different promoters may be useful in such expression cassettes. Preferably, such promoters should be strong to medium strength in the host in which they are used. Promoters may be regulated or constitutive. Preferably, promoters that are not glucose repressed, or repressed only mildly by the presence of glucose in the culture medium, should be used. To name only a few out of many suitable promoters one can mention, for example, promoters of glycolytic genes such as the promoter of *B. subtilis* tsr gene (encoding fructose biphosphate aldolase) or GAPDH promoter from yeast *Saccharomyces cerevisiae* (coding for glyceraldehyde-phosphate dehydrogenase) (Bitter G. A., *Meth. Enzymol.* 152:673–684 (1987)). Other strong promoters such as, for example, the ADHI promoter of baker's yeast (Ruohonen L., et al., *J. Biotechnol.* 39:193–203 (1995)), the phosphate-starvation induced promoters such as the PHO5 promoter of yeast (Hinnen, A., et al., in Yeast Genetic Engineering, Barr, P. J., et al. eds, *Butterworths* (1989), or the alkaline phosphatase promoter from *Bacillus licheniformis* (Lee. J. W. K., et al., *J. Gen. Microbiol.* 137:1127–1133 (1991)). Phage and expression libraries of genomic DNA can be constructed from which any desired sugar metabolism gene that has similarity to corresponding genes from, for example, *S. cerevisiae* can be retrieved.

The useful features of the microbial strains of the present invention are not limited to being achieved by inactivating or over-expressing genes with known function. Certain features of these strains are preferably achieved by random chemically induced or spontaneous mutagenesis followed by selection of strains with improved properties. One particularly efficient selection method, unexpectedly discovered by the present inventors, is based on obtaining mutants of the strains bearing mutations in the transketolase gene which show improved growth properties. It was found that a significant proportion of such mutants transform glucose into a different spectrum of five-carbon sugars than the parent strains do. Particularly, a very significant increase in D-xylulose yield may be achieved through this approach. The mutants can be characterized by assay of the various sugar and PPP intermediates and also assay of the activity of the PPP enzymes. The activity of the PPP enzymes can be assayed using methods known in the art, for example, as described in Alexander, M. A. et al., Appl. Microbiol. Biotechnol. 29: 282–288 (1988).

The fermentation products produced in the hosts and methods of the invention may be obtained individually (in isolated form) or as a mixture with other fermentation products, or other sugars or sugar alcohols (i.e., as an extract or partially purified form). Methods for the purification of five-carbon sugars and their sugar alcohols are known. For example, D-xylose may be isolated from the side streams of cellulose processing and hydrogenated to produce xylitol. The methods for purification of these compounds (including D-ribose-5-phosphate, ribulose-5-phosphate, D-xylulose-5-phosphate, D-ribulose, D-xylulose, D-arabinose, D-lyxose, D-xylose, D-arabitol, ribitol and xylitol from culture medium are well known in the art and include various forms of column cromatography (e.g. ion exchange, adsorption, reverse phase etc.) and crystallization. Precipitation of poorly soluble barium or calcium salts may be used for purification of five-carbon sugar phosphates.

The Cloned XPDH Gene and Protein

A *Lactobacillus rhamnosus* gene encoding xylitol-phosphate dehydrogenase (XPDH) was cloned and decoded. The nucleotide sequence as provided on plasmid pBK(LRX-PDH) is shown in SEQ ID NO:48. The sequence contains an open reading frame of 349 amino acids (SEQ ID NO:49), and begins with the less usual start codon TTG.

The deduced amino acid sequence of the *L. rhamnosus* XPDH sequence is homologous to the sequences of several other medium-chain dehydrogenases, especially, for example, those of *B. halodurans* and *C. difficule*—but for which the substrates were either unknown or erroneously assigned. For example, while SEQ ID NO:50 is the amino acid sequence of XPDH from *B. halodurans* (GenBank PID:g1072799), it was listed there as being a sorbitol dehydrogenase. SEQ ID NO:51–53 had not been annotated: SEQ ID NO:51 is a sequence from *C. difficile* that shows some homology to the *L. rhamnosus* XPDH. SEQ ID NO:52 is a similar sequence from *C. difficile*. SEQ ID NO:53 is a further similar sequence from *C. difficile*. *C. difficile* enzymes have the following homology with *L. rhamnosus* XPDH, SEQ ID NO 51: 52% identical residues, E-value (as calculated by the BLAST algorithm provided by NCBI WWW Internet site) $e^{-109}$. SEQ ID NO 52: 37% identical residues, E-value (as calculated by the BLAST algorithm provided by NCBI WWW Internet site) $e^{-68}$. SEQ ID NO 53: 37% identical residues, E-value (as calculated by the BLAST algorithm provided by NCBI WWW Internet site) $e^{-65}$.

The homology of the *B. halodurans* enzyme that has been experimentally demonstrated to function as XPDH has lower homology values:

SEQ ID NO 50: 36% identical residues, E-value (as calculated by the BLAST algorithm provided by NCBI WWW Internet site) $e^{-63}$.

The Cloned APDH Gene and Protein

An *E. avium* gene encoding arabitol phosphate dehydrogenase (APDH) was cloned and decoded. The nucleotide sequence encoding the gene is shown in SEQ ID NO:68. The sequence contains an open reading frame of 349 amino acids (SEQ ID NO:69)

The deduced amino acid sequence of the *E. avium* APDH sequence is homologous to the sequences of several other medium-chain dehydrogenases, especially, for example, that of a sequence reported to be a sorbitol dehydrogenase in *B. halodurans* (SEQ ID NO:70).

Polynucleotides

Unless otherwise indicated, all nucleotide sequences determined by sequencing a DNA molecule herein were determined as described in the examples, and all amino acid sequences of polypeptides encoded by DNA molecules determined herein were predicted by translation of a DNA sequence determined as above. Therefore, as is known in the art for any DNA sequence determined by this approach, any nucleotide sequence determined herein may contain some errors. Nucleotide sequences determined by automation are typically at least about 35%, for example at least 55%, 65%, 75%, 85% or at least 95% identical. More typically they are about 80% or 90% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

By "functionality" is meant that the nucleotide sequence performs a function that is equal to that of another homolog nucleotide sequence, such as encodes an enzyme having the same activity, e.g. drives the same reaction, as a described enzyme.

Using the information provided herein, such as the nucleotide sequence set out in Figures and sequence listing, a nucleic acid molecule of the present invention encoding a XPDH or APDH polypeptide, or a chimeric construct of a fusion protein of the same, may be obtained using standard cloning and screening procedures, such as those for cloning chromosomal DNA, or cDNAs using mRNA as starting material. Illustrative of the invention, the XPDH or APDH nucleic acid molecule described in the examples was discovered in a chromosomal DNA library derived from *L. rhamnosus*.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA, or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) that encodes a XPDH or APDH protein of the invention, or fusion protein containing the same. Such fusion proteins may be engineered, for example, to provide an additional activity or function to the XPDH or APDH polypeptide or its transcript, or to provide a function that will assist in the purification of the XPDH or APDH protein after host production. Thus, for instance, the polypeptide may be fused to a marker sequence, such as a peptide, which facilitates purification of the fused (marker containing) polypeptide. In certain embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86: 821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767 –778(1984). In one embodiment, the XPDH or APDH coding sequences are operably linked to sequences encoding a signal sequence, such that when translated, the signal sequence directs the produced XPDH or APDH to a desired location in or out of the cell. Such signal sequence may be bacterial or eukaryotic, depending upon whether the XPDH or APDH is produced in a bacterial or eukaryotic host cell.

DNA molecules comprising the coding sequence for the XPDH or APDH protein as shown in SEQ ID NO: 48 or SEQ ID NO:68, or desired fragment thereof, and DNA molecules which comprise a sequence substantially different from those described above, but which, due to the degeneracy of the genetic code, still encode the XPDH or APDH protein amino acid sequence as shown in SEQ ID NO:49 or SEQ ID NO:69. Of course, the genetic code is well known in the art. Thus, it would be routine for one skilled in the art to generate such degenerate variants.

The invention further provides not only the nucleic acid molecules described above but also nucleic acid molecules having sequences complementary to the above sequences. Such isolated molecules, particularly DNA molecules, are useful as probes for gene mapping, by in situ hybridization with chromosomes, and for detecting expression of the XPDH or APDH gene in various species, for example, by Northern blot analysis.

The invention further provides polynucleotides having various residues deleted from the 5' and 3' end of the complete polynucleotide sequence but that retain the reading frame and still encode an XPDH or APDH that has XPDH or APDH catalytic activity. Such polynucleotides thus encode the polypeptides of the invention in embodiments having various residues deleted from the N-terminus or the C-terminus of the complete polypeptide, but that retain the catalytic activity of the XPDH or APDH.

The present invention thus provides isolated nucleic acid molecules, including:

(1) a polynucleotide encoding the *L. rhamnosus* XPDH polypeptide having the amino acid sequence shown in SEQ ID NO:49, especially, the polynucleotide sequence shown in SEQ ID NO:48; or the *E. avium* APDH polypeptide having the amino acid sequence shown in SEQ ID NO:69 especially the polynucleotide sequence shown in SEQ ID NO:68,;

(2) a polynucleotide encoding useful peptide fragments of the XPDH or APDH sequence, such useful fragments including but not limited to fragments that provide the enzymatic, that is catalytically active XPDH or the APDH protein; and (3) a polynucleotide that encode the XPDH or APDH polypeptide as above, but lacking the N-terminal methionine.

The fragments of the isolated nucleic acid molecules described herein retain a desired property or encode a polypeptide that retains a desired property or activity. By a fragment of an isolated nucleic acid molecule as described above is intended fragments at least about 15 nucleotides (nt), and more preferably at least about 20 nt, still more preferably at least about 30 nt, and even more preferably, at least about 40 nt in length which are useful as probes and primers as discussed herein, or to provide a desired motif or domains to a fusion protein construct. Of course, larger fragments 50–300 nt, or even 600 nt in length are also useful according to the present invention as are fragments corresponding to most, if not all, of the nucleotide sequence of the DNA shown in SEA ID NO:48 or 68 or encoding the amino acid sequence SEQ ID NO:49 or 69. By a fragment at least 20 nt in length when compared to that of SEQ ID NO:48 or 68, for example, is intended fragments which include 20 or more contiguous bases from the nucleotide sequence of the nucleotide sequence as shown in SEQ ID NO:48 or 68.

In particular, the invention provides polynucleotides having a nucleotide sequence representing the portion of that shown in SEQ ID NO:48 or 68 or encoding the amino acid sequence shown in SEQ ID NO:49 or 69. Also contemplated are polynucleotides encoding XPDH polypeptides which lack an amino terminal methionine. Polypeptides encoded by such polynucleotides are also provided, such polypeptides comprising an amino acid sequence starting at position 2 of the amino acid sequence shown in SEQ ID NO:49 or 69 but lacking an amino terminal methionine.

In another aspect, the invention provides an isolated nucleic acid molecule comprising a polynucleotide which hybridizes under stringent hybridization conditions to a portion or preferably all of the polynucleotide in a nucleic acid molecule of the invention described above, and especially to SEQ ID NO:48 or 68 or its complement. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 g/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as probes and primers as discussed above and in more detail below.

By a portion of a polynucleotide of "at least 20 nt in length," for example, is intended 20 or more contiguous nucleotides from the nucleotide sequence of the reference polynucleotide (e.g., the nucleotide sequence as shown in SEQ ID NO:48 or 68). Of course, a polynucleotide which hybridizes only to a poly A sequence, or to a complementary stretch of T (or U) residues, would not be included in a polynucleotide of the invention used to hybridize to a portion of a nucleic acid of the invention, since such a polynucleotide would lack specificity and hybridize to any nucleic acid molecule containing a poly (A) stretch or the complement thereof (e.g., practically any double-stranded cDNA clone).

As indicated, nucleic acid molecules of the present invention which encode a XPDH polypeptide may include, but are not limited to the coding sequence for the polypeptide, by itself; the coding sequence for the polypeptide and additional sequences, such as those encoding a leader or secretary sequence, such as a pre-, or pro- or prepro-protein sequence; the coding sequence of the polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities.

Variant and Mutant Polynucleotides

The present invention further relates to variants of the nucleic acid molecules of the present invention, which encode portions, analogs, or derivatives of the XPDH. Variants may occur naturally, such as a natural allelic variant. By an "allelic variant" is intended one of several alternate forms of a gene occupying a given locus on a chromosome of an organism. *Genes II,* Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the XPDH polypeptide or portions thereof. Also especially preferred in this regard are conservative substitutions.

Further embodiments of the invention include an isolated nucleic acid molecule comprising a polynucleotide having a nucleotide sequence encoding a polypeptide, the amino acid sequence of which is at least 35% identical to, and more preferably at least 55%, 65%, 75%, 85% and 95% identical to the entire amino acid sequence shown in SEQ ID NO:49 or 69, especially those that hybridize under stringent hybridization conditions to the same. Such a polynucleotide which hybridizes as above does not hybridize under stringent hybridization conditions to a polynucleotide having a nucleotide sequence consisting of only A residues or of only T residues.

As a practical matter, whether any particular nucleic acid molecule is by way of example at least 35%, 55%, 75%, 85% or 95% identical to, for instance, the nucleotide sequence shown in SEQ ID NO:48, can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In another embodiment, the variant polynucleotides of the invention include nucleic acid molecules that have at least 35%, 55%, 65%, 75%, 85%, 95% or 99% identical to the nucleic acid sequence shown in SEQ ID NO:48 or 68, irrespective of whether they encode a polypeptide having XPDH or APDH activity. This is because even where a particular nucleic acid molecule does not encode a polypeptide having XPDH or APDH activity, one of skill in the art would still know how to use the nucleic acid molecule, for instance, as a hybridization probe or a polymerase chain reaction (PCR) primer. Uses of the nucleic acid molecules of the present invention that do not encode a polypeptide having XPDH activity include, inter alia: (1) isolating a XPDH or APDH gene or allelic variants thereof in a cDNA library; (2) in situ hybridization to metaphase chromosomal spreads to provide precise chromosomal location of the XPDH or APDH gene; and Northern Blot analysis for detecting mRNA expression in specific tissues.

Of course, due to the degeneracy of the genetic code, one of ordinary skill in the art will immediately recognize that a large number of the nucleic acid molecules having a homolog sequence identical to the nucleic acid sequence shown in SEQ ID NO:48 or 68 will encode a polypeptide having XPDH or APDH enzymatic (that is, catalytic) activity, respectively. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having XPDH or APDH enzymatic activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the nucleic acid molecules of the present invention, host cells that are genetically engineered with the recombinant vectors of the invention, the production of XPDH or APDH polypeptides or fragments thereof by recombinant techniques, and the uses of the same.

The polynucleotides of the invention may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

For expression of the encoded protein, a DNA insert encoding such protein should be operatively linked to an appropriate promoter capable of directing transcription in the desired host. Examples of useful prokaryotic promoters include: the B. subtilis degQ promoter, and especially the degQ36 mutation of the same, the phage lambda PL promoter, the E. coli lac, trp and tac promoters, the SV40 early and late promoters and promoters of retroviral LTRs, to name a few. The native promoter can also be used. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in B. subtilis, E. coli and other bacteria. Representative examples of appropriate hosts include, but are not limited to, bacterial cells, such as B. subtilis, E. coli, Streptomyces and Salmonella typhimurium cells; fungal cells, such as yeast cells; insect cells such as Drosophila S2 and Spodoptera Sf9 cells. Preferred hosts include are microbial cells, especially bacterial and yeast cells. If desired, mammalian cells can be used as a host for the cloned gene. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

Polypeptides and Fragments

The invention further provides an isolated or purified XPDH polypeptide having the amino acid sequences encoded by the amino acid sequence in SEQ ID NO:49, or a peptide or polypeptide comprising a portion of the above polypeptide, especially as described above and encoded by a nucleic acid molecule described above.

The invention further provides fusion proteins of the XPDH protein, especially as encoded by the polynucleotides described above, for example, wherein the XPDH amino acid sequences are fused to a signal sequence or to the a polypeptide to improve stability and persistence in the host cell, during purification or during subsequent handling and storage. Also, peptide moieties may be added to the polypeptide to facilitate purification, for example, as described above. Such regions may be removed prior to final preparation of the polypeptide. The addition of peptide moieties to polypeptides to engender secretion or excretion, to improve stability and to facilitate purification, among others, are familiar and routine techniques in the art.

The XPDH protein as described above can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

The XPDH or APDH polypeptides of the present invention include naturally purified products, products of chemical synthetic procedures, and products produced by recombinant techniques from a prokaryotic or eukaryotic host, including, for example, microbial cells such as bacterial and yeast, and especially *B. subtilis* and *Saccharyomyces.* and also higher plant, insect and mammalian cells, In addition, polypeptides of the invention may also include an initial modified methionine residue, in some cases as a result of host-mediated processes.

XPDH or APDH polynucleotides and polypeptides may be used in accordance with the present invention for a variety of applications, particularly those that make use of the chemical and biological properties of XPDH or APDH.

Variant and Mutant Polypeptides

To improve or alter the characteristics of a XPDH or APDH polypeptide, protein engineering may be employed. Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function.

However, even if deletion of one or more amino acids from the N-terminus of a protein results in modification or loss of one or more biological functions of the protein, other biological activities may still be retained. Thus, the ability of the shortened protein to induce and/or bind to antibodies which recognize the complete or portion of the XPDH or APDH protein generally will be retained when less than the majority of the residues of the complete protein or extracellular domain are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence shown in SEQ ID NO:49 or 69.

However, even if deletion of one or more amino acids from the C-terminus of a protein results in modification or loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature form protein are removed from the C-terminus. Whether a particular polypeptide lacking C-terminal residues of a complete protein retains such immunologic activities can readily be determined by routine methods described herein and otherwise known in the art. The invention also provides polypeptides having one or more amino acids deleted from both the amino and the carboxyl termini.

Other Mutants

In addition to terminal deletion forms of the protein discussed above, it will also be recognized by one of ordinary skill in the art that some amino acid sequences of the XPDH or APDH polypeptide can be varied without significant effect on the structure or function of the proteins. The artisan will recognize that there will be critical areas on the protein which determine activity. Thus, the invention further includes variations of the XPDH or APDH polypeptide, which show substantial XPDH or APDH polypeptide activity or which include regions of XPDH or APDH protein such as those that retain the XPDH or APDH enzymatic activity. Such mutants include deletions, insertions, inversions, repeats, and type substitutions Guidance concerning which amino acid changes are likely to be phenotypically silent can be found in Bowie, J. U. et al., "Deciphering the Message in Protein Sequences: Tolerance to Amino Acid Substitutions," *Science* 247:1306–1310 (1990).

Thus, the fragment, derivative, or analog of the polypeptide of SEQ ID NO:49 or 69 may be: (i) one in which one or more of the amino acid residues are substituted with a conserved or non-conserved amino acid residue (preferably a conserved amino acid residue(s), and more preferably at least one but less than ten conserved amino acid residue(s)), and such substituted amino acid residue(s) may or may not be one encoded by the genetic code; or (ii) one in which one or more of the amino acid residues includes a substituent group; or (iii) one in which the mature or soluble extracellular polypeptide is fused with another compound, such as a compound to increase the half-life of the polypeptide (for example, polyethylene glycol).; or (iv) one in which the additional amino acids are fused to a leader or secretory sequence or a sequence which is employed for purification of the mature polypeptide or a proprotein sequence. Such fragments, derivatives and analogs are deemed to be within the scope of those skilled in the art from the teachings herein.

Thus, the XPDH or APDH of the present invention may include one or more amino acid substitutions, deletions or additions, either from natural mutations or human manipulation. As indicated, changes are preferably of a minor nature, such as conservative amino acid substitutions that do not significantly affect the folding or activity of the protein as shown below.

| | |
|---|---|
| Aromatic | Phenylalanine |
| | Tryptophan |
| | Tyrosine |
| Hydrophobic | Leucine |
| | Isoleucine |
| | Methionine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Glycine |

Amino acids in the XPDH or APDH protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro proliferative activity.

The polypeptides of the present invention are preferably provided in an isolated form. By "isolated polypeptide" is intended a polypeptide removed from its native environment. A polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the XPDH polypeptide can be substantially purified by the method used to purify the *L. rhamnosus* native XPDH protein, as described by Hausman and London, *J. Bacteriol* 169(4):1651–1655 (1987)). Preferably, the polypeptide of the invention is purified to a degree sufficient for sequence analysis, or such that it represents 99% of the proteinaceous material in the preparation.

The present inventors have discovered the XPDH gene, and the APDH gene, and the recombinant use of the same for the production of xylitol and/or arabitol in microbial hosts. Especially, the XPDH enzyme is useful in a pathway in which xylulose-5-P is converted to xylitol-1-P by XPDH, and then the xylitol-1-P is converted to xylitol, for example, with phosphatase. Such xylitol is preferably excreted from the cell and recovered in purified and isolated form. In other embodiments, XPDH analogs, such as SEQ ID NOs:50, 51, 52 and 53 are also useful in the methods of the invention as a substitute for XPDH, especially for the recombinant production of xylitol. Also, especially the APDH activity is useful in a method for the production of arabitol, and APDH analogs, such as SEQ ID NO:70 may be used therein in its place.

The invention includes polypeptides are at least 35% identical, more preferably at least 55% or 75% identical, still more preferably at least 85%, 95%, or 99% identical to the polypeptide having the sequence shown in SEQ ID NO:49 or 69, and also include portions of such polypeptides with at least 30 amino acids and more preferably at least 50 amino acids.

As a practical matter, whether any particular polypeptide is by way of example at least 35%, 55%, 65%, 75%, 85%, 95% or 99% identical to, for instance, the amino acid sequence shown in SEQ ID NO: 49 or 69 can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptides of the present invention that possess XPDH or APDH activity can be used to provide such activity in vivo or in vitro, for example, in assays for the same or in assays for metabolites such as the enzyme's substrate or product, or coupled for use with more multienzyme systems.

The invention is thus described in more detail in the following examples. The examples below are for illustrative purposes only and are not deemed to limit the scope of the invention.

EXAMPLES

The discussion above is complemented by the examples provided herein, in part summarized below:

Examples 1, 2 and 3 exemplify bacterial hosts in which ribose-5-P isomerase activity is reduced or eliminated.

Examples 2 and 3 exemplify bacterial hosts in which transketolase activity is reduced or eliminated.

Example 5 exemplifies bacterial hosts in which ribulose-5-P 3-epimerase activity is enhanced or modified.

Example 6 exemplifies bacterial hosts in which the conversion of xylulose-5-P to xylulose is enhanced or modified.

Example 7 exemplifies bacterial hosts in which xylitol dehydrogenase activity is enhanced or modified.

Example 9 exemplifies bacterial hosts in which tagatose epimerase activity is enhanced or modified for the conversion of ribulose to xylulose.

Example 10 exemplifies bacterial hosts in which the glucose PTS (PEP-dependent transport) system activity is modified, replaced or supplemented with an ATP-dependent kinase based hexose uptake and phosphorylation system.

Example 11 exemplifies bacterial hosts in which glucose-6-phosphate dehydrogenase and/or 6-phosphogluconate dehydrogenase activity is enhanced or modified.

Example 12 exemplifies yeast hosts in which transketolase and xylulokinose activities are eliminated, and in which xylitol dehydrogenase activity is introduced.

Example 13 exemplified a yeast host in which the accumulation of 5-carbon sugar phosphates is enhanced.

Examples 14, 15, 17, 20 and 22 exemplify yeast hosts in which the accumulation of polyols and/or pentoses is enhanced.

Example 15 exemplifies yeast hosts in which the ratios of xylitol and ribitol produced were altered by xylitol dehydrogenase with different substrate specifities.

Examples 16 and 17 exemplifies yeast hosts in which dephosphorylating enzymes, active on 5-carbon sugar phosphates, are introduced, and in which the accumulation of polyols and pentoses is enhanced, and in which the ratio of polyols and pentoses is altered, and in which the flux of glucose into PPP is enhanced.

Example 18 exemplifies yeast hosts in which glucose-phosphate isomerase activity is reduced or eliminated.

Example 19 exemplifies yeast hosts in which transketolase and glucose-phosphate isomerase activities are eliminated.

Example 20 exemplifies yeast hosts in which 6-phosphofructo-2-kinase activity is eliminated.

Example 21 exemplifies yeast hosts in which an electron sink has been enhanced or modified for the regeneration of $NADP^+$.

Example 21 and 22 exemplify yeast hosts in which the cellular cofactor balance has been modified for the regeneration-of $NADPH^+$.

Example 23 exemplified yeast hosts with enhanced polyol and pentose production obtained by classical mutagenesis.

Example 25 describes the cloning of xylitol-phosphate dehydrogenase (XPDH) from *Lactobacillus rhamnosus*.

Example 26 describes the construction of expression vectors pGTK74(LRXPDH) and pGTK74(BHDH)

Example 27 describes the expression of xyitol-phosphate dehydrogenase genes (XPDH) from *L. rhamnosus* and from *R. halodurans*

Example 28 exemplifies a method for the production of xylitol by recombinant *B. subtilis* strains that express XPDH.

Example 29 exemplifies the over-expression of the *B. subtilis* glcUgdh operon.

Example 30 describes that purification and partial sequencing of arabitol-phosphate dehydrogenase from *Enterococcus avium*.

Example 31 describes the expression of the arabitol-phosphate dehydrogenases from *E. avium* and *B. halodurans* in *B. subtilis*.

Example 32 describes the production of arabitol by the recombinant strains of *B. subtilis*.

Example 1

Cloning of the *B. subtilis* rpi Gene Coding for D-Ribose-Phosphate Isomerase

At the time when the work was initiated, the complete genomic sequence of *B. subtilis* was not yet available. Also, it was not known whether *B. subtilis* contained one or more D-ribose-phosphate isomerase genes (*E. coli* was known to contain two). Therefore, the strategy for cloning the rpi gene(s) was based on functional complementation of D-ribose-auxotrophic mutation in *E. coli* rather than on PCR. Presently, the preferred mode for cloning the rpi gene(s) would be to use PCR based techniques rather than the method as exemplified below. However, the method described in this example is fully adequate for practicing the present invention.

A gene library was constructed from the DNA of *B. subtilis* (ATCC 6051). The DNA of this strain was partially cut with the restriction endonuclease Sau3A and fragments exceeding 3 kb in size were isolated by preparative agarose gel electrophoresis. Unless indicated otherwise, standard genetic engineering methods well known in the art were used throughout the studies supporting this invention (Maniatis, T., et al., (1982, Molecular cloning, Cold Spring Harbor Laboratory). This fraction was then used to construct a *B. subtilis* gene library using λ ZAP Express Predigested Vector/Gigapack Cloning Kit (Stratagene, USA). The library was converted to the plasmid form according to the instructions of the manufacturer except that *Escherichia coli* AS11 strain (rpiA$^-$, a D-ribose auxotroph obtained from Genetic Stock Center, 830 Kline Biology Tower, MCD Biology Department , 266 Whitney Ave., PO Box 208103, Yale University, New Haven, Conn. 06520-8193: See: cgsc-.biology.yale.edu was used instead of the strain suggested by the manufacturer. An aliquot of the plasmid-form library in the AS11 strain was transferred to the plates containing the standard *E. coli* mineral medium (M9). Plasmids were isolated from the colonies growing on this medium and analyzed by restriction analysis. A large majority of them appeared overlapping by restriction analysis. More extensive restriction analysis of one of the clones belonging to the most abundant group (coded p131, FIG. 1) indicated that it is derived from the sequenced part of the *B. subtilis* chromosome. This area contained an open reading frame with strong homology to the rpiB coding region of *E. coli*.

Example 2

Construction of *B. subtilis* Strains Containing rpi$^-$ and tkt$^-$ Mutation

Figure 2:
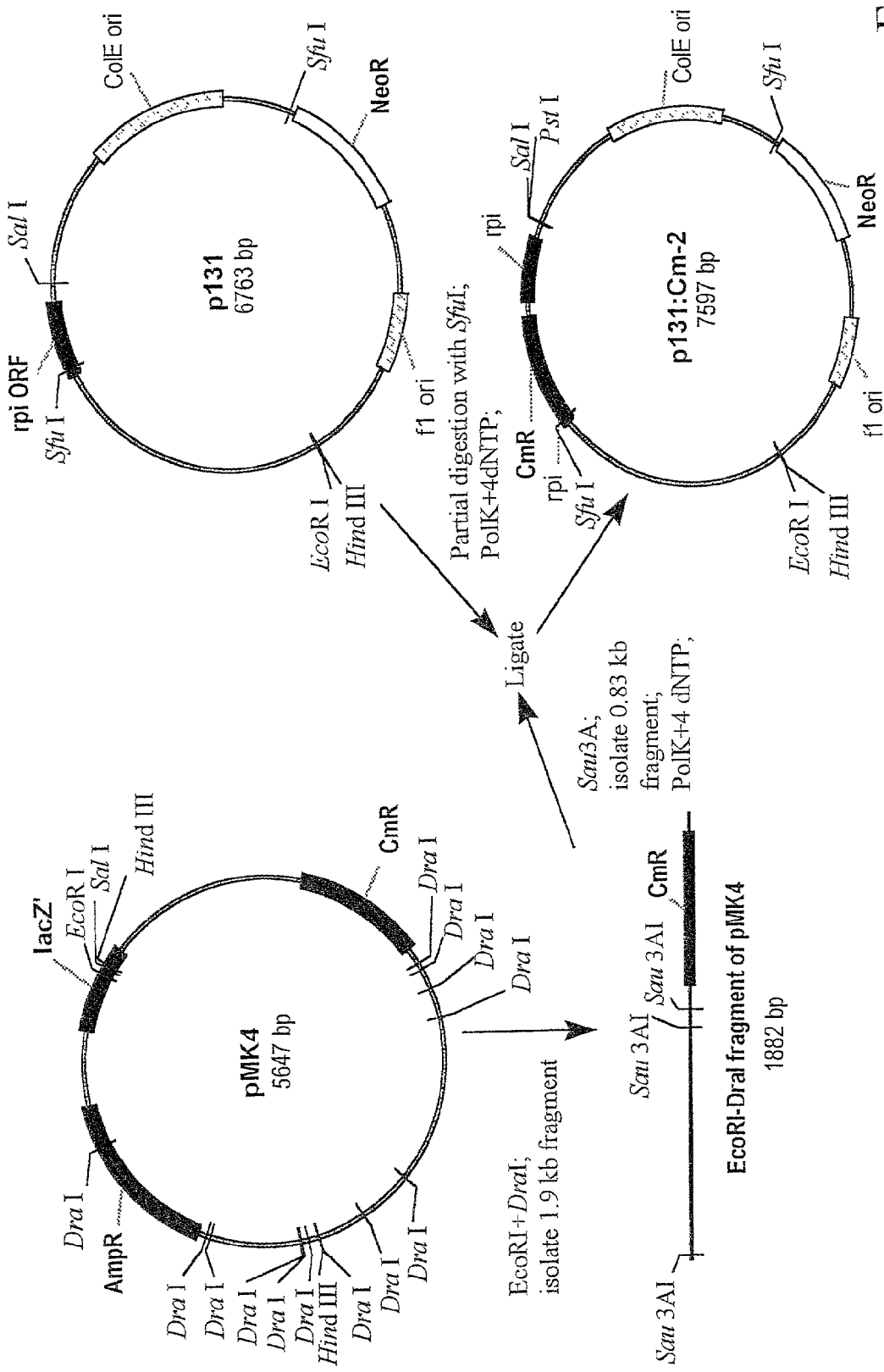
FIG. 2. Construction and structure of plasmid p=131:Cm-2.

The chloramphenicol resistance gene was isolated from the plasmid pMK4 (obtained from the *Bacillus* Genetic Stock Center (BGSC, Ohio, USA). pMK4 was digested with DraI and EcoRI, a 1.9 kb fragment was isolated from the digest by preparative agarose gel electrophoresis and further digested with Sau3A. A purified 0.83 kb fragment from this digest was purified and treated with Klenow fragment of the DNA-polymerase I in the presence of all four deoxynucleotide triphosphates. This fragment was than ligated with the plasmid p131 (Example 1) digested with SfuI and similarly treated with the Klenow fragment. Plasmid p131-Cm2 containing the *B. subtilis* rpi gene disrupted by the chloramphenicol resistance gene was isolated after transformation of *E. coli* with this ligation mixture (FIG. 2).

p131-Cm2 was digested with EcoRI and PstI and the digest was used to transform the *B. subtilis* strain BD170 (trpC2, thr$^-$5, obtained from BGSC) to chloramphenicol resistance using the natural competence of *B. subtilis*. The transformation protocol followed the so-called "Paris method" (Molecular Biological Methods for *Bacillus*, Harwood and Cutting, eds., John Wiley and sons, Chichester, N.Y. (1990), pp. 148–149). The transformants were screened by running PCR reactions using the chromosomal DNA preparations (Molecular Biological Methods for *Bacillus*, Harwood and Cutting, eds., John Wiley and sons, Chichester, N.Y. (1990), p. 65) from individual clones as templates and a pair of oligonucleotides oCA5 (SEQ ID NO: 1) and oBS-RP13 (SEQ ID NO: 2) as primers. Standard PCR conditions used here and in subsequent examples (unless specified otherwise) were: 3 min at 93° C. followed by 25 cycles of 45 sec at 60° C., 3 min at 72° C. and 30 sec at 93° C. The transformants positive by this assay (generating an approximately 1.35 kb PCR product) were further cloned and the chromosomal DNA of the resulting sub-clones assayed by PCR using a different pair of oligonucleotide primers (oBS-RPI5 (SEQ ID NO: 3) and oBS-RPI3 (SEQ ID NO: 2). One clone generating a DNA fragment of the expected size (about 2.1 kb as opposed to 1.25 kb in wild-type B. subtilis) was selected and tested for D-ribose auxotrophy. Indeed, this clone was found to be auxotrophic for D-ribose strongly suggesting that only one D-ribose-phosphate isomerase gene is present in B. subtilis. This clone was named GX1.

Figure 10:
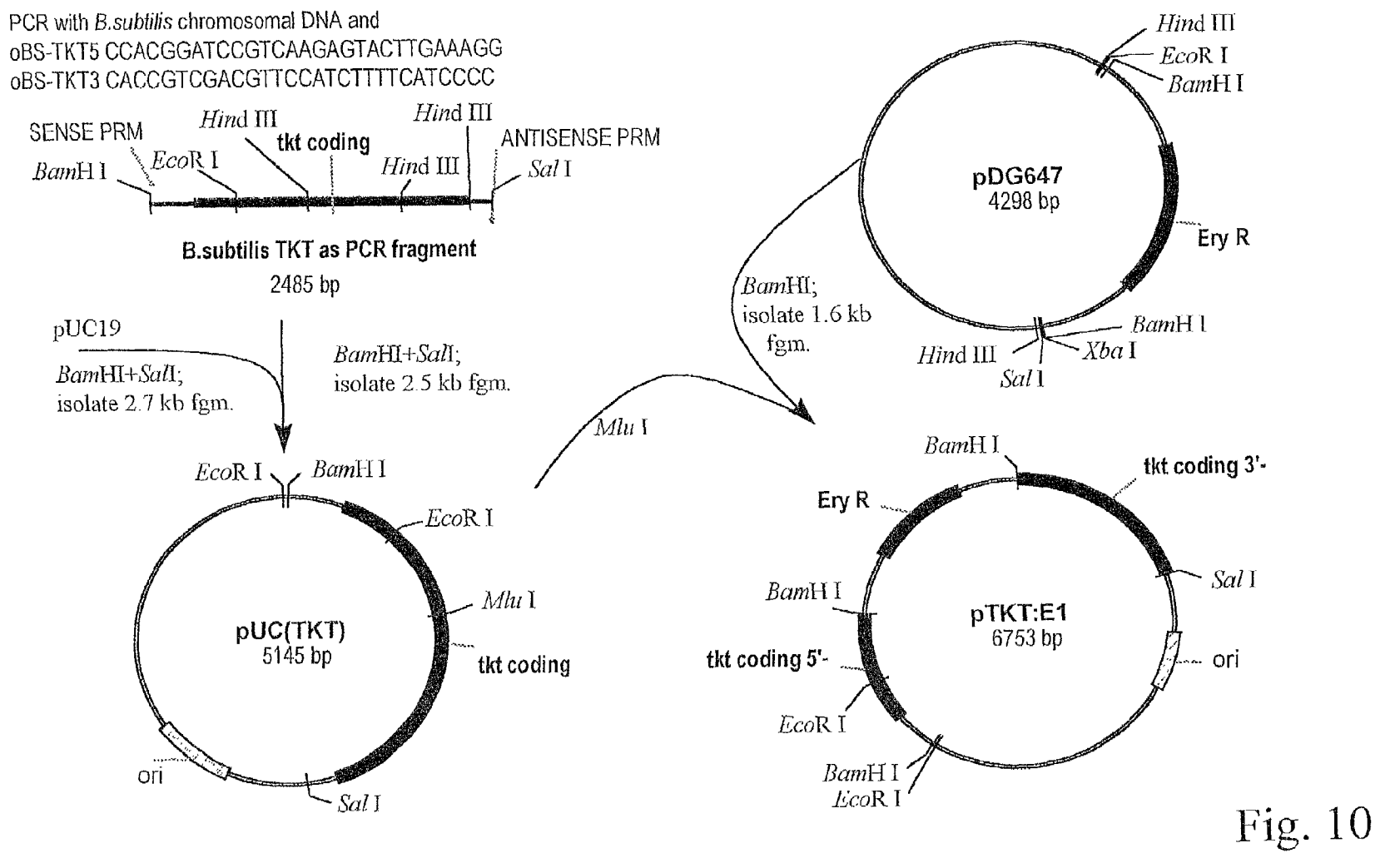

The tkt gene of B. subtilis encoding transketolase was cloned by PCR based on the known sequence of the B. subtilis chromosomal DNA. Oligonucleotide oBS-TKT5 (SEQ ID NO: 18) was used as the sense primer and oBS-TKT3 (SEQ ID NO: 19) as the anti-sense primer. The PCR fragment was cloned into the standard laboratory vector pUC 19 resulting in plasmid pUC(TKT). The erythromycin resistance gene was subsequently inserted into the MluI site of pUC(TKT) in the form of a 1.6 kb BamHI fragment of plasmid pDG647 (obtained from BGSC). Construction of plasmids pUC(TKT) and pTKT:E1 is illustrated in FIG. 10.

Plasmid pTKT:E1 was digested with SalI and SmaI and the resulting digest was used to transform the B. subtilis strains BD170 and GX1 to erythromycin resistance. A random set of the transformant clones was analyzed by PCR using oBS-TKT5 and oBS-TKT3 as primers and the clones generating an approximately 4 kb DNA fragment were selected. The B. subtilis strain derived by this procedure from BD170 was named GX4 and a similar derivative of GX1 was named GX5.

Example 3

Construction of D-ribulose-producing B. subtilis Strains

Chromosomal DNA was isolated from the strain GX1 by the method referred to in Example 2 (except that Na-sarcosyl used in the original protocol was replaced with Na-dodecylsulfate). This DNA was used to transform the D-ribose-producing B. subtilis strain 31094 (U.S. Pat. No. 3,970,522) using the natural competence based method (Example 2). The transformants were screened by the PCR methods described in the Example 2 and also by studying the products of the glucose fermentation by these strains. One clone generating the fragment of the expected size in PCR with the oligonucleotide pair oBS-RPI5 and oBS-RPI3 and retaining the ability of the parent strains to convert glucose into five-carbon sugars was selected. The rpi-disrupted derivative of strain ATCC 31094 was named GX2.

Example 4

Ribulose Production with Recombinant Strains of B. subtilis

B. subtilis strains ATCC 31094, GX2, GX4 and GX5 were pre-cultured overnight in LB medium (Bacto-Tryptone (Difco) 1%, Yeast extract (Difco)—0.5%, NaCl 1%) and inoculated into the same medium additionally containing 10% glucose to an initial $OD_{600}$ of 1. Cultures of about 10 ml, in 20 ml test tubes, were placed at an angle of about 30° to horizontal in a rotary shaker and cultivated at 37° C. and 200 rpm for 3 days. The carbohydrates in the fermentation broth were analyzed by HPLC. HPLC analyses were done on a Hitachi 665A-12 liquid chromatograph equipped with refractive index detector. A Bio-Rad HPX87P 7.8×200 mm column was used. The column was equilibrated with water at 70° C. and eluted with water at 0.9 ml/min. The standard solutions for the HPLC were prepared from reagents obtained from Sigma Chemical Company. These solutions were made either directly from dry crystalline sugars or from syrups dried in vacuum over NaOH pellets until constant weight (xylulose and D-ribulose).

As can be seen from the data presented in Table 1, the rpi-mutation dramatically changes the spectrum of five-carbon sugars produced by the B. subtilis strains. D-ribose is no longer produced and D-ribulose becomes the dominant fermentation product. D-xylulose production which is difficult to detect in the parent strains becomes apparent although D-xylulose yields are much lower than those of D-ribulose. The Δtkt mutants GX4 and GX5 obtained by gene disruption produced qualitatively similar spectra of five-carbon sugars as the strains ATCC 31094 and GX2 bearing the chemically-induced tkt mutation. However, GX4 and GX5 grew somewhat slower than ATCC 31094 and its derivatives. Most probably, this is explained by the accumulation of "compensatory" mutations in the strain ATCC 31094. Therefore, subjecting these strains to several cycles of cultivation in glucose-rich medium, sub-cloning (on the same medium) and selection for the larger, faster-growing clones can improve fermentation characteristics of GX4 and GX5.

TABLE 1

Production of five-carbon sugars from glucose by B. subtilis strains having mutations in the tkt and rpi genes (mg/ml).

| Strain Name | Relevant Genotype | Xylulose | Ribulose | Ribose |
|---|---|---|---|---|
| ATCC 31094 | tkt- | n.d.(*) | 2.31 | 1.23 |
| GX2 | tkt-, Δrpi | 0.44 | 4.54 | 0.00 |
| GX4(**) | Δtkt | n.d. | 1.4 | 1.2 |
| GX5(**) | Δtkt, Δrpi | n.d. | 0.8 | n.d. |

(*)n.d. - below reliable detection limit (this limit is approx. 0.15–0.25 mg/ml for B. subtilis fermentation media)
(**)Fermentation time - 5 days Example 5

Construction of B. subtilis Strains Over-expressing D-ribulose 5-phosphate Epimerase The vector for over-expression of the D-ribulose-5-phosphate epimerase in B. subtilis-pBS(AR2T) was constructed from the following elements:

Gram-positive replicon and chloramphenicol resistance marker from the plasmid pGDV1 (Molecular Biological Methods for Bacillus, Harwood and Cutting, eds., John Wiley and Sons, Chichester, N.Y., pp. 82–83) (obtained from BGSC);

E. coli replicon and ampicillin resistance marker from the plasmid pMOB (Strathmann, M., et al., Proc. Natl. Acad. Sci. USA 88:1247–1250 (1991));

Kanamycin resistance gene from plasmid pDG783 (Guérot-Fleury et al., Gene 167:335–336 (1995));

Promoter of the B. subtilis aldolase gene (tsr, also known fba), cloned by PCR using oligonucleotides oALDOP5 (SEQ ID NO: 4) and oALDOP3 (SEQ ID NO: 5);

Coding sequence of the D-ribulose 5-phosphate epimerase gene from *E. coli,* cloned by PCR using oligonucleotides oRPE5 (SEQ ID NO: 6) and oRPE32 (SEQ ID NO: 7);

Transcriptional terminator of the glycolytic operon of *B. subtilis,* also cloned by PCR using oligonucleotides oENOT5 (SEQ ID NO: 8) and oENOT3 (SEQ ID NO: 9).

Figure 3:
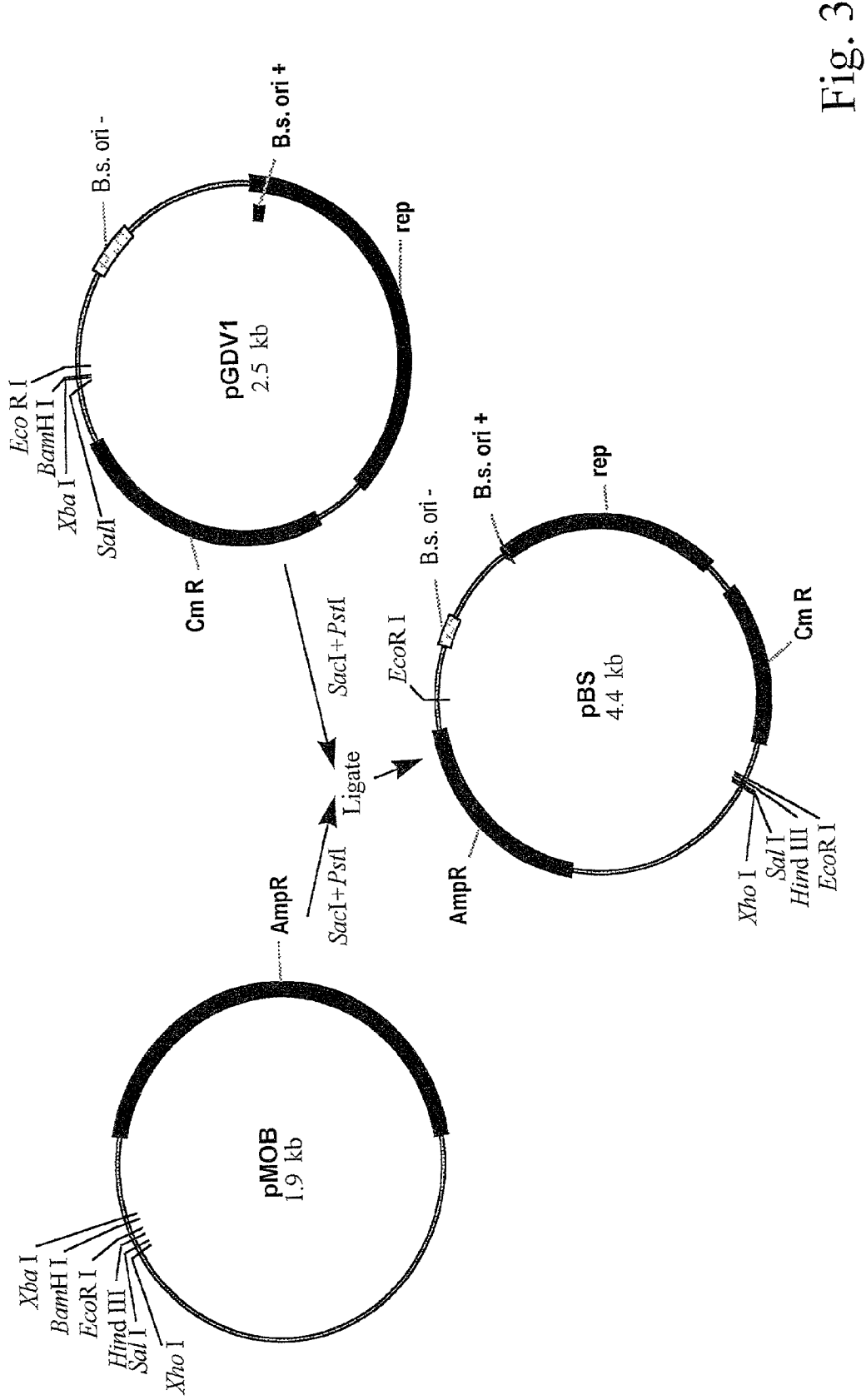
FIG. 3. Construction and structure of plasmid pBS.
Figure 4:
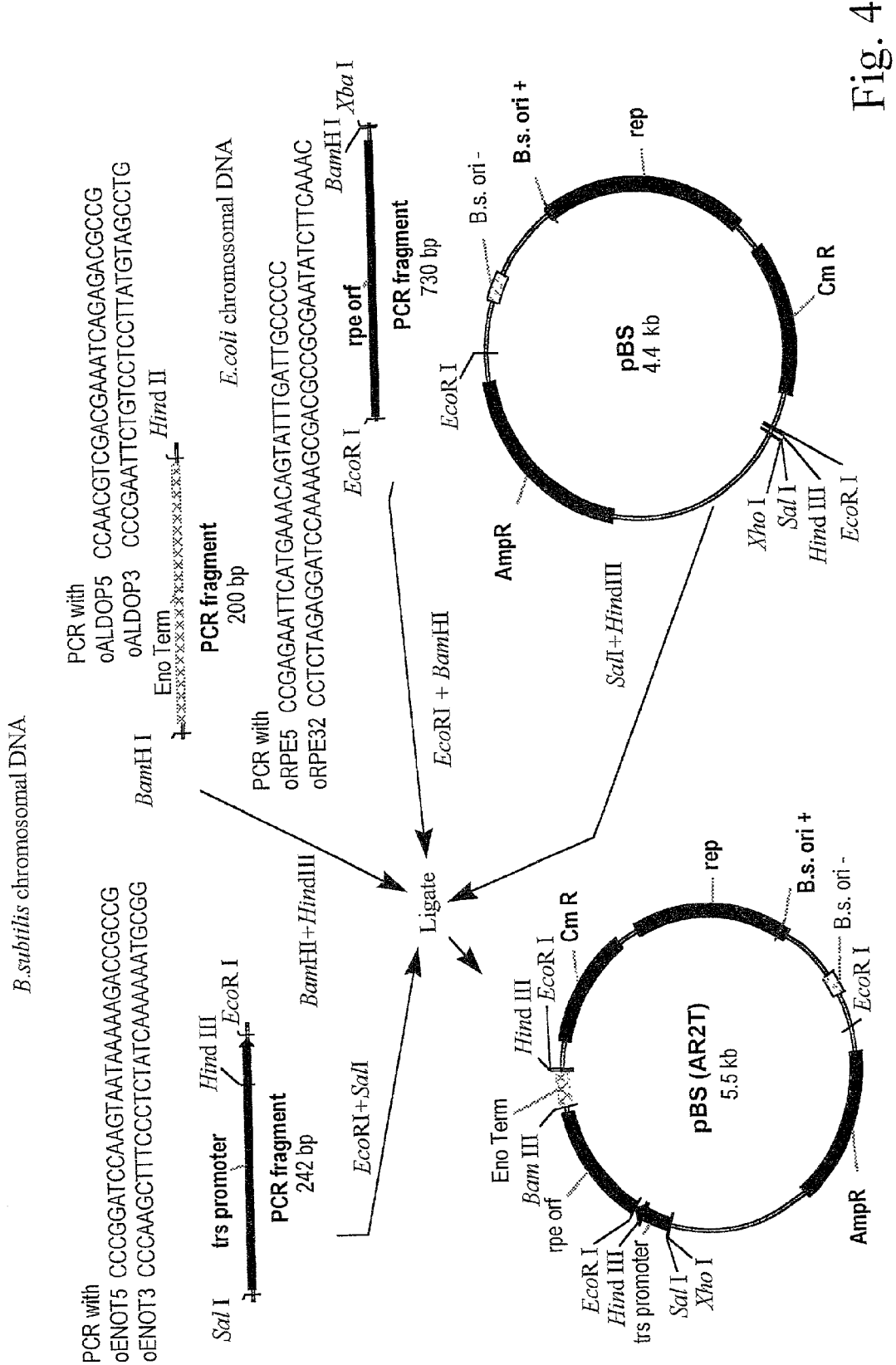
FIG. 4. Construction and structure of plasmid pBS (AR2T). Oligonucleotides oENOT5 and oENOT3 are SEQ ID Nos. 8 and 9, respectively. Oligonucleotides oALDOP5 and oALDOP3 are SEQ ID Nos. 4 and 5, respectively. Oligonucleotides oRPE5 and oPRE32 are SEQ ID Nos. 6 and 7, respectively.
Figure 5:
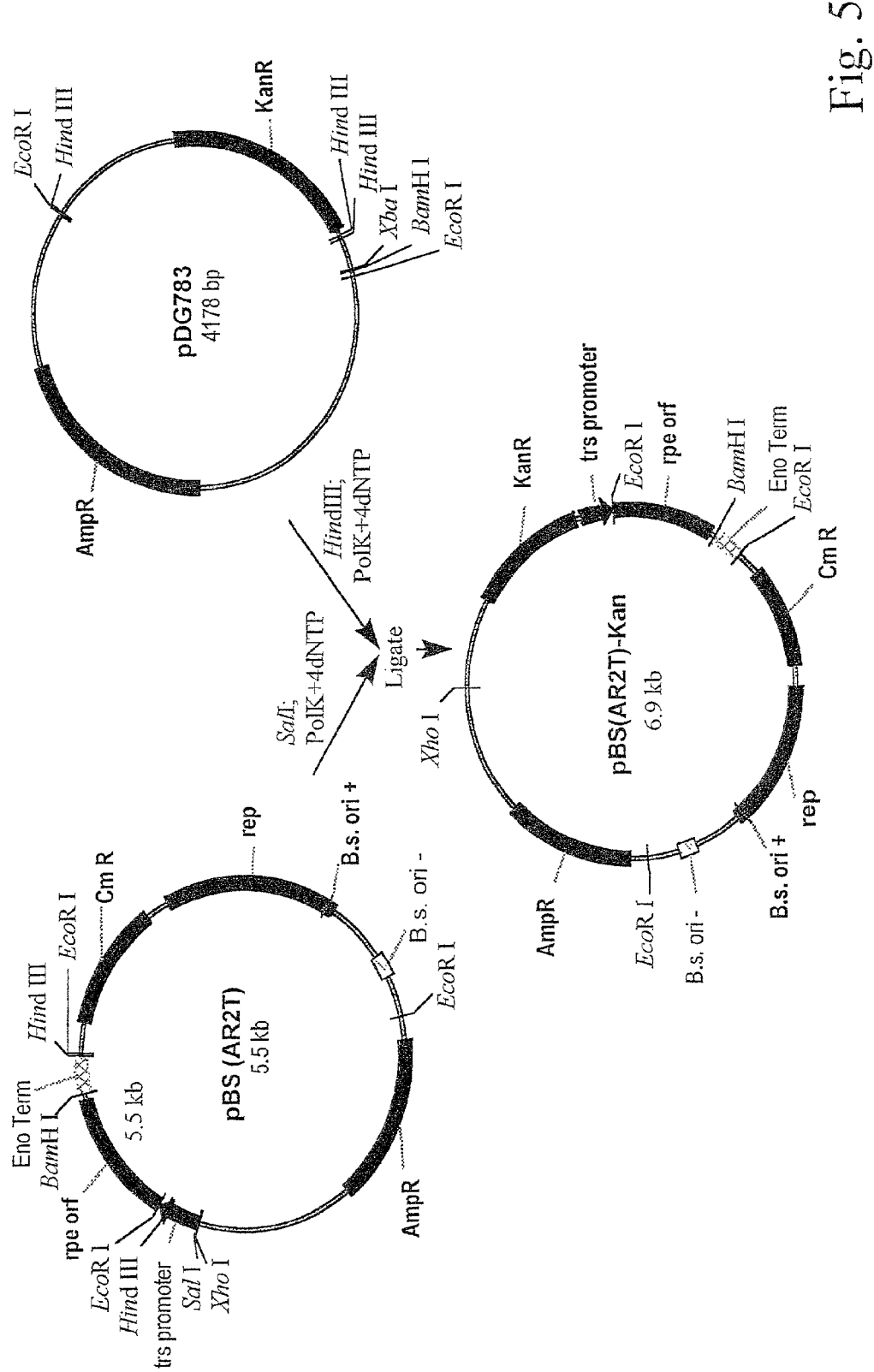
FIG. 5. Construction and structure of plasmid pBS (AR2T)-Kan.

The construction of the plasmid pBS(AR2T)-Kan is illustrated by FIGS. 3, 4 and 5.

*B. subtilis* strain GX2 was transformed with pBS(AR2T)-Kan using the procedures described in the Examples 2 and 3. About 50 ml cultures of two randomly chosen transformants were grown overnight in 250 ml Erylenmeyer flasks (rotary shaker, 37° C., 200 rpm. LB medium, containing 25 mg/l kanamycin). *B. subtilis* strain GX2 used as a control. It was grown under identical conditions except that kanamycin was omitted. The cell extracts were prepared and the activity of the D-ribulose 5-phosphate epimerase was measured using a known method (Sasajima, K. and Yoneda, M., *Agr. Biol. Chem.* 38:1297–1303 (1974)). The transformants were found to express D-ribulose 5-phosphate epimerase at about 30–50 times (10–20 U/mg$_{protein}$) higher level than the wild type control (0.3–0.4 U/mg$_{protein}$). The effect of glucose on the activity of aldolase promoter was studied later in a separate experiment (Example 8). It was found that this promoter (controlling the expression of xylitol-dehydrogenase gene on a multi-copy plasmid pGT24(MXD2)) is moderately repressed by the presence of glucose in the culture medium (about 3–10-fold).

Production of Five-carbon Sugars by *B. subtilis* Strains Over-expressing D-ribulose 5-phosphate Epimerase GX2 transformed with pBS(AR2T)-Kan was cultivated under conditions described in the Example 4. The parent strain GX2 was used as a control. The effect of D-ribulose-5-phosphate epimerase expression was followed by calculating the ratio of D-xylulose and D-ribulose in the culture broth after 3–7 days of cultivation. Indeed, this ratio was increased, although only moderately (typically about two-fold, from about 5–7% to 10–12%, Table 2).

Example 6

Selecting *B. subtilis* Mutants Producing Increased Amounts of D-xylulose 0.1–1 ml (per 90 mm Petri plate) of overnight culture of GX2 transformed with pBS(AR2T)-Kan (grown in LB containing 25 mg/l kanamycin) was placed on a selective plate (LB with addition of D-xylose—10% and kanamycin—25 mg/l). The plates were incubated at 37° C. for about one day. The separate colonies (typically—tens to hundreds) appearing on the plate were purified by sub-cloning, cultivated on LB-glucose medium and the spectrum of five-carbon sugars produced was analyzed by HPLC. It was found that some of the mutants selected by the above procedure produce dramatically higher levels of D-xylulose than the parent strain. Very similar results were also obtained with GX2 strain subjected to the same selection/screening procedure except that antibiotic was omitted from the xylose-containing selective medium. The results of these experiments are summarized in Table 2. One D-xylulose-overproducing mutant of the strain GX2 was named *B. subtilis* GX7 and used in the subsequent work.

TABLE 2

Production of D-ribulose and D-xylulose from glucose by the strains of D-xylose-resistant mutant of *B. subtilis* strains GX2 and GX2 transformed with pBS(AR2T)-Kan

| *B. subtilis* strain | Xylulose, g/l | Ribulose, g/l | Xylulose: ribulose ratio, % |
|---|---|---|---|
| Experiment 1 | | | |
| GX2 | 0.9 | 14.2 | 7 |
| GX2[pBS(AR2T)-Kan] | 0.8 | 6.9 | 12 |
| GX2[pBS(AR2T)-Kan]-mutant clone X2 | 4.3 | 8.1 | 53 |
| GX2[pBS(AR2T)-Kan]-mutant clone X3 | 4.3 | 8.0 | 54 |
| GX2[pBS(AR2T)-Kan]-mutant clone X4 | 5.1 | 9.4 | 54 |
| Experiment 2 | | | |
| GX2 | 0.3(*) | 10.7 | 2.4(*) |
| GX2-mutant clone 27 (strain GX7) | 6.8 | 21.6 | 31 |

(*)Approximate values. Measurement of D-xylulose concentration in this low range is only semi-quantitative.

Example 7

Construction of *B. subtilis* Strains Over-expressing Xylitol Dehydrogenase

Plasmid pGTK24(MXD2) was constructed in two steps. First, a general purpose *E. coli-B. subtilis* expression vector pGTK24 containing the promoter of the *B. subtilis* aldolase gene and the transcription terminator of enolase gene was constructed. Construction of the plasmid pGTK24 involved the following genetic engineering operations:

The *E. coli* origin of replication was amplified by PCR using pUC19 as a template and the two oligonucleotides: oOR15 (SEQ ID NO: 10) and oORI32 (SEQ ID NO: 11) as primers; the PCR fragment was digested with EcoRI and BclI and ligated with pGDV1 digested with the same enzymes. The resulting plasmid was named pGT21.

pGT21 was digested with SalI and EcoRI and ligated with a pair of synthetic oligonucleotides oPLI5 (SEQ ID NO: 12) and oPLI3(SEQ ID NO: 13), resulting in plasmid pGT22.

The transcription terminator of the *B. subtilis* glycolytic operon (enolase gene) was isolated by PCR using chromosomal DNA of *B. subtilis* as template and the two oligonucleotides oENOT5 (SEQ ID NO: 8) and oENOT3 (SEQ ID NO: 9). The PCR product was digested with BamHI and HindIII and cloned into the polylinker area of pGT22 digested with the same restriction endonucleases. The resulting plasmid was named pGT23.

Plasmid pGT23 was digested with a mixture of SalI and EcoRI and ligated with a PCR fragment containing the aldolase promoter and digested with the same enzymes (PCR template: *B. subtilis* chromosomal DNA, PCR primers: oALDOP5 (SEQ ID NO: 4) and oALDOP3 (SEQ ID NO: 5)). The resulting construction (plasmid pGT24) is a convenient small size shuttle (*E. coli-B. subtilis*) vector providing transcription initiation and termination signals and a ribosome-binding site immediately preceding a unique EcoRI site followed by several other unique restriction sites (XbaI, AhoI, BamHI). The aldolase promoter of pGT24 can easily be exchanged with any other promoter using the SalI and EcoRI restriction sites. The chloramphenicol resistance marker is selectable in both E. coli and B. subtilis.

Plasmid pGTK24 is a derivative of pGT24 in which the chloramphenicol resistance gene is replaced with a kanamycin resistance gene. This was achieved by amplifying the kanamycin resistance gene of the plasmid pDG783 by PCR using two oligonucleotide primers: oKAN5 (SEQ ID NO: 14) and oKAN3 (SEQ ID NO: 15), digesting the PCR product with ScaI and BamHI and ligating with pGT24 digested with BclI and SnaBI.

Figure 6:
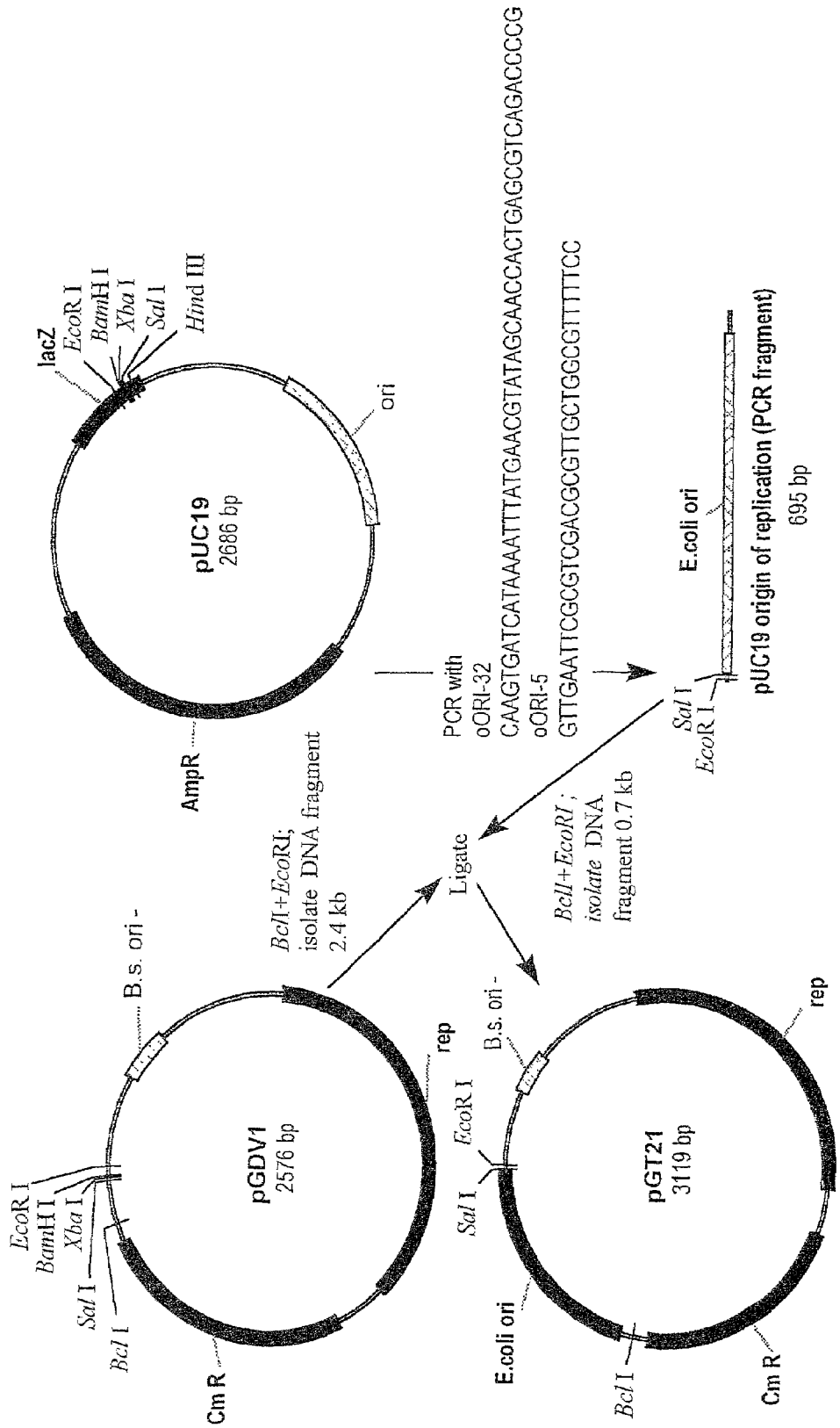
FIG. 6. Construction and structure of plasmid pGT21. Oligonucleotides oORI-32 and oORI-5 are SEQ ID Nos. 11 and 10, respectively.
Figure 7:
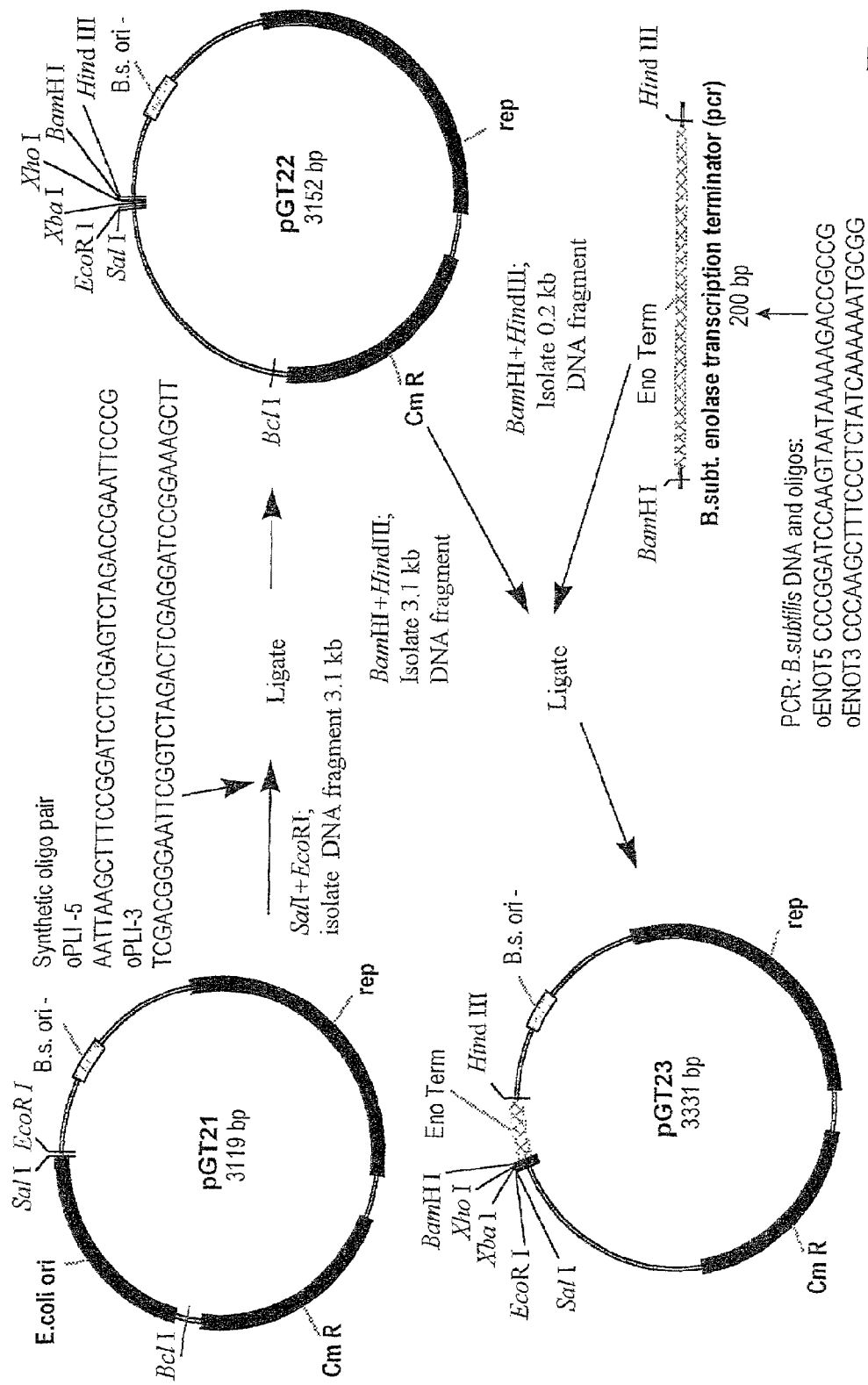
FIG. 7. Construction and structure of plasmid pGT23. Oligonucleotides oPLI-5 and oPLI-3 are SEQ ID Nos. 12 and 13, respectively. Oligonucleotides oENOT5 and oENOT3 are SEQ ID Nos. 8 and 9, respectively.
Figure 8:
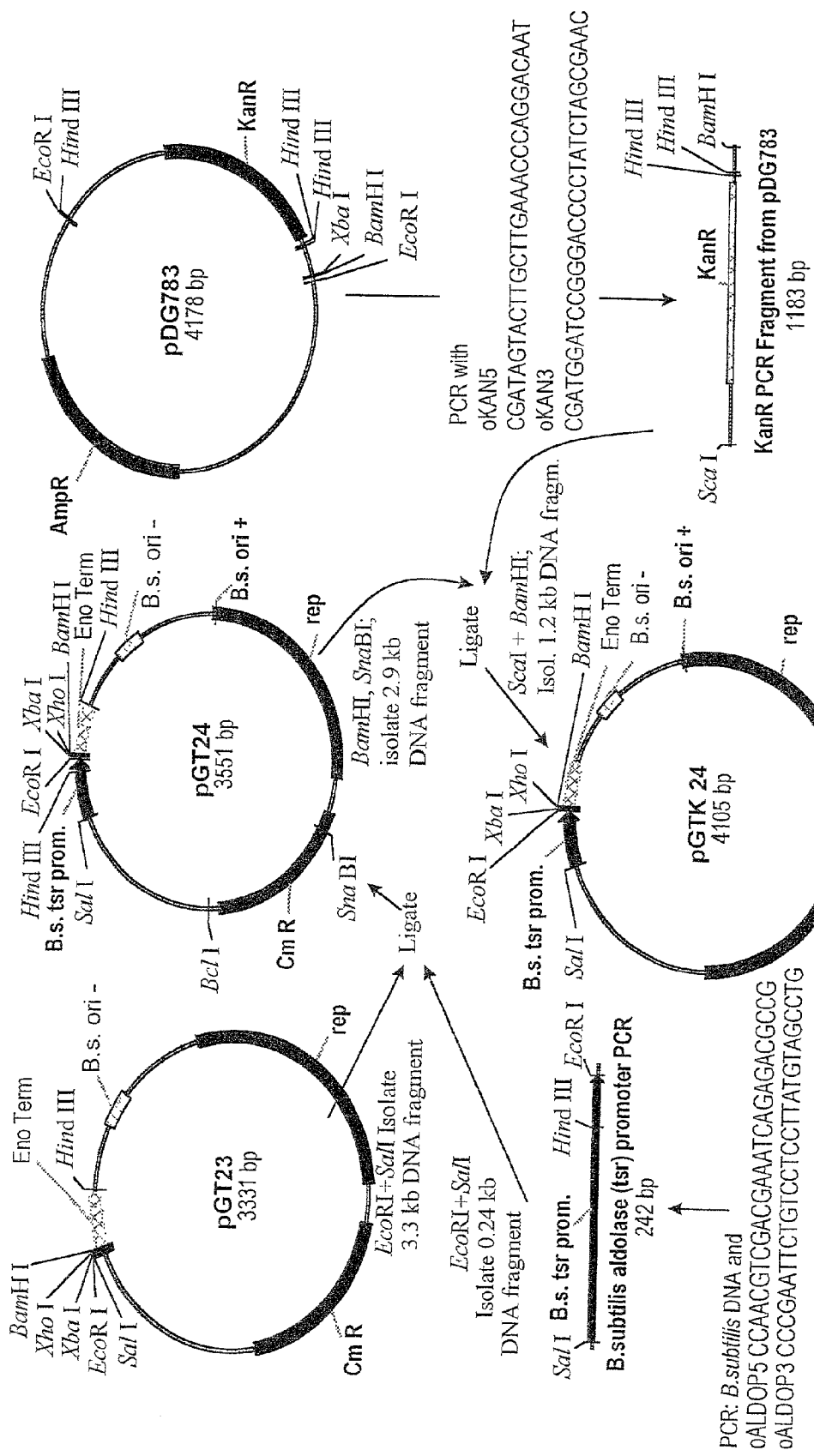
FIG. 8. Construction and structure of plasmids pGT24 and pGTK24. Oligonucleotides oKAN5 and oKAN3 are SEQ ID Nos. 14 and 15, respectively. Oligonucleotides oALDOP5 and oALDOP3 are SEQ ID Nos. 4 and 5, respectively.
Figure 9:
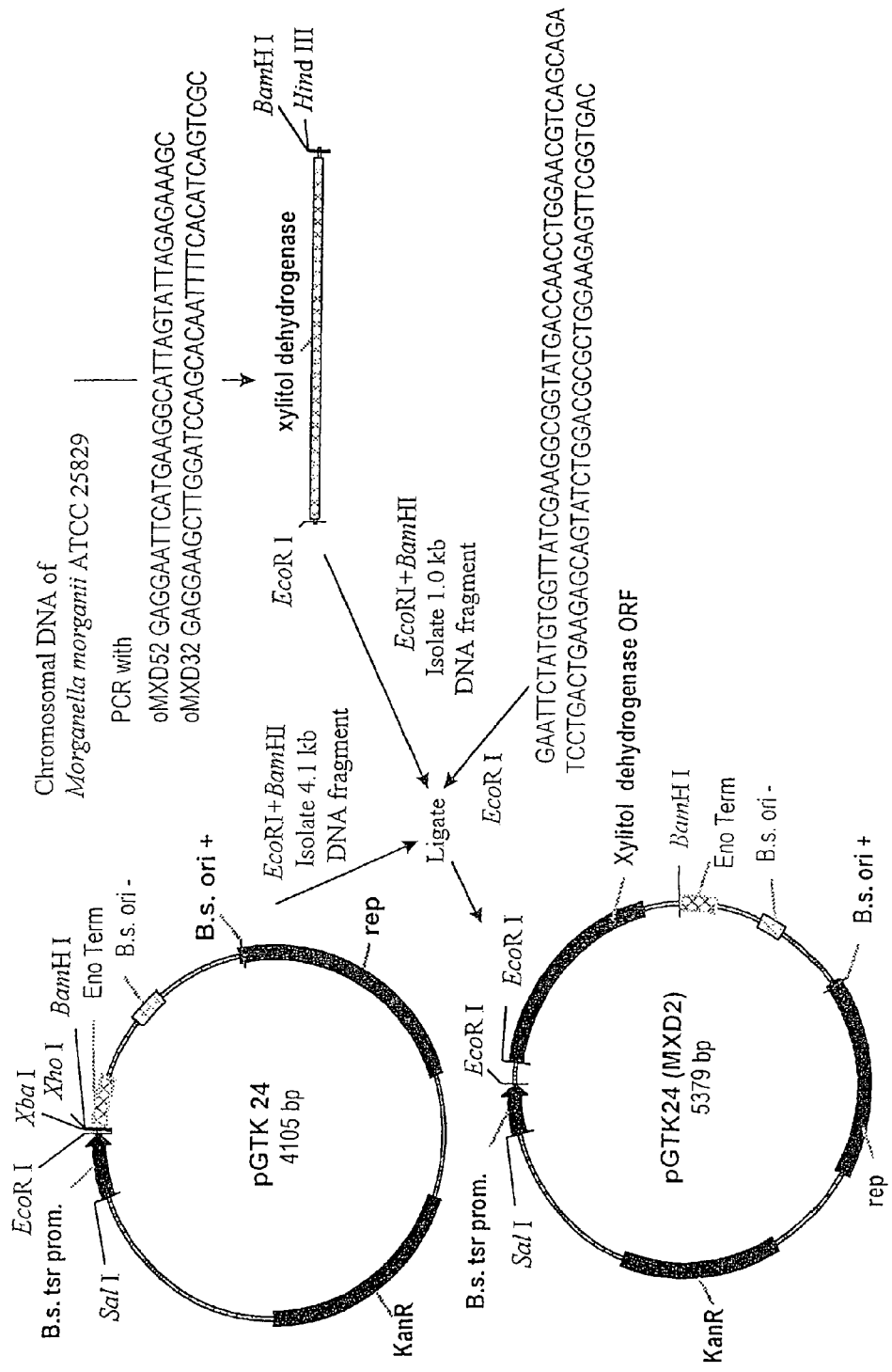
FIG. 9. Construction and structure of plasmid pGTK24 (MXD2). Oligonucleotides oMXD52 and oMXD32 are SEQ ID Nos. 16 and 17, respectively. The sequence GAATTC-TATGTGGTTATCGAAGGCGGTATGAC-CAACCTGGAACGTCAGCAGATC CTGACTGAAGAG-CAGTATCTGGACGCGCTGGAAGAGTTCGGTGAC is SEQ ID No. 75.

Construction of plasmids pGT24 and pGTK24 is illustrated by FIGS. 6, 7 and 8. in the second part of the synthesis, a coding sequence of the xylitol dehydrogenase (XDH) gene from gram-negative bacterium Morganella morganii ATCC 25829 was cloned by PCR using the known sequence of this gene (GenBank accession number L34345). The sense and anti-sense oligonucleotides used in this PCR were oMXD52 (SEQ ID NO: 16) and oMXD32 (SEQ ID NO: 17). The PCR amplified coding sequence of the XDH gene was inserted between the promoter and transcription terminator of the expression vector pGTK24 (details shown by the FIG. 9). The resulting plasmid pGTK24(MXD2) was found to contain an additional 99 bp DNA fragment inserted into the EcoRI site. This DNA fragment (having the sequence: GAATTCTATGTGGTTATCGAAGGCGG-TATGACCAACCTGGAACGTCAGCAGATC-CTGACTGAAGAGCAGTATCTG-GACGCGCTGGAAGAGTTCGGTGAC (SEQ ID NO. 75)) is apparently derived from the rpoBC region of the E. coli chromosome. To the best of our knowledge, this fragment has no functional role in pGTK24(MXD2) being just a cloning artifact. It does not seem to have a strong influence on the expression of the xylitol dehydrogenase gene in either E. coli or B. subtilis. pGTK24(MXD2) was introduced into the B. subtilis strain BD170 and GX7 (Example 6) by the procedures described above (B. subtilis strain BD170 serving as an intermediate host for transformation of GX7).

The strain BD 170 [pGTK24(MXD2)] as well as untransformed strain BD 170 was grown overnight on either LB or LB, containing 10% glucose, cell extracts were prepared and the XDH activity measured. The assay conditions for measuring XDH activity were: 30° C., 50 mM Tris-HCI, pH 7.0, 0.2 mM NADH and 10 mM D-xylulose. Changes of absorption at 340 nm were recorded; one unit of activity was defined as the amount of enzyme that catalyzed the reduction of one mole of substrate per minute under the conditions of assay (assuming the differential absorption coefficient NADH/NAD$^+$ to be equal to $6.25 \times 10^4$ M$^{-1}$cm$^{-1}$). The following levels of XDH activity were measured in the strain BD170 [pGTK24(MXD2)] grown on the two media: LB—0.5 U/mg$_{proteins}$, LB-glucose 0.05–0.15 U/mg$_{protein}$. Thus, glucose appeared to repress the activity of the aldolase promoter 3–10 fold. No XDH activity could be detected in the strain BD170 grown on either of the two media.

Example 8

Production of Five-carbon Sugars and Sugar Alcohols by a Strain of B. subtilis Expressing Xylitol Dehydrogenase A plasmid containing B. subtilis strain GX7 [pGTK24 (MXD2)] was cultivated in LB medium containing 10% glucose essentially as described in Example 3 except that aeration conditions were varied in different fermentations and longer cultivation times were used. The variations in the aeration levels were qualitative and achieved by varying culture volume and shaking conditions. "High" aeration was achieved by shaking (at 200 rpm) a 3 ml culture in a 20 ml test tube fixed at a 30° angle to the platform of the shaker; "medium" aeration was achieved by cultivating a 10 ml culture under the same conditions; "low" aeration conditions were the same as "medium" except that the test tubes were fixed in vertical position. The results of these experiments are summarized in the Table 3.

The data presented in the Table 3 show clearly that by adjusting fermentation conditions and by expressing a suitable polyol dehydrogenase within the bacterial cells one can achieve wide-ranging control over the nature of five-carbon sugars/sugar alcohols produced by the recombinant B. subtilis. Taking the results of the Table 3 as an example, one can see that the conversion yield of a ketosugar to a sugar alcohol in the fermentation product mixture may be varied from essentially zero to about 80%.

TABLE 3

Influence of the expression of XDH and aeration conditions on accumulation of D-xylulose and xylitol in the culture medium of B. subtilis strain GX7

| Strain | Aeration level | Fermentation time (days) | Xylulose, g/l | Xylitol, g/l | Xylitol/Xylulose ratio |
|---|---|---|---|---|---|
| GX7 | High | 10 | 6.6 | <0.1 | — |
|  | Medium | 10 | 11.1 | 0.15 | 0.01 |
|  | Low | 10 | 1.6 | <0.1 | — |
|  | High- > Low | 3 + 7(*) | 2.9 | 0.46 | 0.16 |
|  | Low | 23 | 8.6 | 0.7 | 0.08 |
| GX7 [pGTK24(MXD2)] clone 1 | High | 10 | 3.4 | 0.1 | 0.03 |
|  | Medium | 10 | 4.5 | 0.54 | 0.12 |
|  | Low | 10 | 0.21 | 0.34 | 1.62 |
|  | High to Low | 3 + 7(*) | 2.5 | 2.2 | 0.88 |
|  | Low | 23 | 1.4 | 3.7 | 2.64 |
| GX7 [pGTK24(MXD2)] clone | High | 10 | 6.3 | 0.16 | 0.03 |
|  | Medium | 10 | 7.5 | 1.4 | 0.19 |
|  | Low | 10 | 0.38 | 0.55 | 1.45 |
|  | High to Low | 3 + 7(*) | 2.6 | 2.1 | 0.81 |
|  | Low | 23 | 1.4 | 5.2 | 3.71 |

(*)3 days of fermentation under highly aerated conditions followed by 7 days under low aeration conditions It should be noted that the expression vector pGTK24 (MXD2) provides for only moderate levels of XDH in the recombinant *B subtilis* cells. The use of promoters stronger than the aldolase promoter will increase the XDH expression level and the efficiency of D-xylulose-xylitol bioconversion. Further improvement of this system can be achieved by a more accurate control of the fermentation conditions (particularly, the dissolved oxygen concentration, glucose concentration and feed rate in a fed-batch fermentation etc.). The slow rate of conversion of glucose into xylitol in the experiments described in this example is explained by the use of simple, batch-wise fermentations. This rate may be improved by using fed-batch fermentations wherein higher density cultures of *B. subtilis* (for example, cell densities about or over 100 g cell dry weight per liter may be obtained for *Bacillus*) or by immobilizing the cells at high density on a solid phase carrier.

Example 9

The Production of Other Five-carbon Sugars and Sugar Alcohols by Fermentation of Glucose with *B. subtilis*

The general efficiency and flexibility of the bioconversion of glucose into five-carbon sugars has been established by the present invention and illustrated by the Examples 1–8. The same concept may be extended further to produce and obtain five-carbon sugars other than D-ribulose, D-xylulose and xylitol, which were used as the models in these studies.

One such extension is to substitute the ribitol dehydrogenase gene in place of the xylitol dehydrogenase gene used in our experiments. For example, the ribitol dehydrogenase gene of *Klebsiella aerogenes* (Loviny, T., et al. Biochem. J. 230:579–585 (1985)) is expressed in the strain GX2 and the ribitol that is produced is collected and, if desired, isolated. Ribitol production is maximized by controlling or adjusting the aeration conditions during fermentation, as shown above. In this example, the strains that are transformed with the gene for ribitol dehydrogenase are used to direct carbon flow from glucose into either D-ribulose or ribitol. The ribitol that is produced is isolated using known procedures.

Arabitol may be produced from glucose by fermentation with the recombinant *B. subtilis* strains transformed with genes coding for either of the two enzymes: D-xylulose-forming arabitol dehydrogenase gene e.g. from *Klebsiella terrigena* [U.S. Pat. No. 5,631,150] or a D-ribulose-forming arabitol dehydrogenase gene e.g. from *Pichia stipitis* [(Hallborn, J., et al.,Yeast 11:839–847 (1995), Genbank sequence accession no. Z46866]. In the former case, the preferred host for transformation is a D-xylulose-producing strain such as GX7, in the latter case it is a D-ribulose-producing strain such as GX2. The arabitol that is produced is isolated using known procedures.

The hosts that produce ribulose, for example, *Bacillus subtilis* ATCC 31094, GX2 or GX7, can be further modified by (over-)expressing, within the host, a gene encoding ketose 3-epimerase (this enzyme is also known as tagatose epimerase). As the result of such modification, xylulose production in these hosts is increased. The nucleotide sequence of a suitable ketose 3-epimerase gene from *Pseudomonas cichorii* is available from GenBank under accession number AB000361.

Similarly, the hosts that produce ribulose, for example, *Bacillus subtilis* ATCC 31094, GX2 or GX7, may be further modified for efficient xylitol production. In this case, both a gene encoding a xylitol dehydrogenase (for example, xylitol dehydrogenase from *Morganella morganii*, GenBank accession number L34345) and a gene encoding a ketose 3-epimerase (such as the gene described in the preceding paragraph) should be co-expressed in such host.

Another embodiment of this invention is to express one of the many known aldose-isomerase genes in the ketopentose-producing *B. subtilis* strains and thus direct the fermentation towards, for example, D-xylose (expressing any of the very large number of known D-xylose-isomerases in the D-xylulose-producing strain GX7).

Similarly, D-lyxose is produced, by expressing in a D-xylulose-producing *Bacillus* host a D-mannose isomerase gene (Stevens, F. J., et al., J. Gen. Microbiol. 124:219–23 (1981); Allenza, P., et al., Appl. Biochem. Biotechnol. 24–25:171–182 (1990)). The D-lyxose is isolated using known procedures.

A gene coding for L-fucose isomerase e.g. the *E. coli* gene fucI (its sequence is found in GenBank under accession number U29581) and is expressed in the D-ribulose-producing strain GX2. This results in production of D-arabinose—an unusual stereoisomer of the more common L-arabinose (Garcia-Junceda, E., et al., Bioorg. Med. Chem. 3:1349–1355 (1995)).

Example 10

Enhancement of Glucose Carbon Flow into the Pentose-phosphate Pathway and Modification of Glucose Uptake System in *Bacillus subtilis*

Numerous mutations disrupting the upper part of the glycolytic pathway in *B. subtilis* are known (Sonenshein, L., et al., eds., *Bacillus subtilis* and other Grain-Positive Bacteria, American Society for Microbiology, 1993, p. 173), including, for example, mutations in phosphoglucoisomerase, phosphofructokinase and fructose biphosphate aldolase genes. Such mutations can relatively easily be constructed in any *Bacillus subtilis* strain using known sequences of the corresponding genes (pgi, fruB, fbaA (tsr), iolJ) and gene disruption techniques.

Inactivation of the glucose-specific PTS system in *B. subtilis* can preferably be achieved by mutating the ptsG gene either via random mutagenesis or, preferably, by recombinant DNA-based techniques (gene disruption). The use of the latter technique is simplified by the availability of the DNA sequence of the ptsG gene (e.g. at the World Wide Web site (See: genomeweb.pasteur.fr/GenoList/SubtiList/).

Many glucokinase and hexokinase genes are known and can be used for the purposes of the present invention. For example, the homologous glucokinase of *B. subtilis* (encoded by glcK gene) can be over-expressed using techniques already described in this specification. Hexokinases have an advantage of accepting both glucose and fructose as substrates. For example, well known yeast HXK1 or HXK2 genes encoding hexokinases I and II can be used and expressed in PTS-deficient hosts.

Additional glucose transport capacity in the bacterial strains with the modified glucose uptake system can be achieved in two ways. Firstly, selection of fast-growing clones on glucose-based media provides a very powerful screening method that in combination with a suitable mutagenesis technique (such as chemical or UV-induced mutagenesis) would easily provide mutants with the desired property. Alternatively, homologous (e.g. that encoded by the glcT1 gene) or heterologous glucose transporters/facilitators from other organisms (preferably, prokaryotic, such as the glf gene of *Zymomonas mobilis*, Weisser, P., et al., *J. Bacteriol.* 177(11):3351–3354 (1995)) can be expressed in the *Bacillus* hosts.

Example 11

Increasing Capacity of the Oxidative Branch of PPP

The capacity of the PPP of the hosts of the invention can be increased by over-expressing the homologous or heterologous genes encoding the key enzymes of the pathway: glucose 6-phosphate dehydrogenase and 6-phosphogluconate dehydrogenase (and, optionally, phosphoglucolactonase). In one embodiment of this invention glucose 6-phosphate dehydrogenase genes from organisms which metabolize glucose only via 6-phosphogluconate (such as heterofermentative lactic acid bacteria) are used. A suitable example of such a gene is the zwf gene of *Zymomonas mobilis* (Barnell, W. O., et al., *J. Bacteriol.* 172(12):7227–7240 (1990)).

Example 12

Genetic Constructions to the TKL1 and TKL1,2 Deficient Strains of *Saccharomyces Cerevisiae*; Transformation of the Xylitol Dehydrogenase (XDH) Encoding Genes and Deletion of the Xylulokinase (XK) Encoding Gene The *Saccharomyces cerevisiae* strain W303-1B (Thomas, B. J. and Rothstein, R., *Cell* 56:619–630 (1989)) with both the TKL1 and TKL2 encoding genes disrupted (Schaaff-Gerstenschläger, I., et al., *Eur. J. Biochem.* 217:487–492 (1993)) was obtained from Dr. I. Schaaff-Gerstenschläger. The strain was renamed as H1055.

The following general methods were used throughout in constructing different yeast strains:

The DNA fragments of interest were cut out of an agarose gel and put into an eppendorf tube (about 200–300 μl). The agarose was crushed with a thick, sterile glass rod. 200 μl of 10 mM TrisHCl pH 7.5, 1 mM EDTA-buffer (TE) was added. Optionally, the crushed agarose/TE was let to stand at 4° C. over night to improve the yield. 300 μl phenol was added, vortexed for one minute and immediately frozen in liquid nitrogen. The frozen tube was centrifuged for 15 min at room temperature. The water phase was moved to a clean tube, extracted with 300 l chloroform-isoamylalcohol (24: 1), vortexed for 0.5 min and centrifuged for 3 min. The water phase was moved to a clean tube. The DNA was precipitated with 1/10 volume of 3 M sodium acetate and 2.5×volume of 94% cold ethanol at −20° C. over night (or −70° C., 30 min). The precipitate was centrifuged 15–20 min at 4° C. The pellet was washed with 70% ethanol and dried. The DNA was dissolved in TE or water. Alternatively, the QIAquick method was used following the instructions of the QIAquick Spin Handbook for QIAquick Gel Extraction kit, Qiagen GmbH, Germany.

*Escherichia coli* was transformed by electroporation following the instructions of the Bio-Rad Gene Pulser apparatus. All yeast transformations were performed by the lithium acetate method (Hill, J., et al., *Nucl. Acids Res.* 19:5791 (1991); Gietz, D., et al, *Nucl. Acids Res.* 20:1425 (1992)). All yeast strains and plasmids constructed are listed in the Appendices 1 and 2.

All yeast cultivations were routinely carried out in either 1% yeast extract, 2% peptone (YP) or in modified yeast synthetic complete medium with essential amino acids and bases [SC; Sherman et al., Methods in yeast genetics. A laboratory manual. Cold Spring Harbor Laboratory. Cold Spring Harbor, N.Y., USA (1983)] containing the indicated carbon source (D for glucose, F for fructose) in aerobic shake flasks at 30° C. and in a 250 rpm shaker. A yeast minimal medium contains 6.7 g/l of yeast nitrogen base (Merck, Germany), the carbon source as indicated and only the amino acids and bases needed due to the auxotrophy of the strain. The TKL1,2 deficient strain cannot grow without the aromatic amino acids.

A yeast strain with only the TKL1 encoding gene disrupted was constructed. Strain CEN.PK2-1D [renamed as H1346, Boles, E., et al., *Mol. Microbiol.* 20:65–76 (1996)] was used as the host strain. The plasmid containing the disruption fragment for TKL1 encoding gene was obtained from Jörg Hauf(Darmstadt, Germany) and renamed as B1087. It is a pUC19 vector carrying the TKL1 encoding gene disrupted by the URA3 encoding gene [Schaaff-Gerstenschläger, I. and Zimmermann, F. K., *Curr. Genet.* 24:373–376 (1993)]. The plasmid B1087 was digested with SacI and BamHI to release the disruption fragment, which was isolated from an agarose gel. The H1346 strain was transformed with the fragment and transformants were selected on plates lacking uracil to obtain URA3 positive clones. The deletion was confirmed by Southern blot analysis. The resulting strain was named as H1764.

Figure 11:
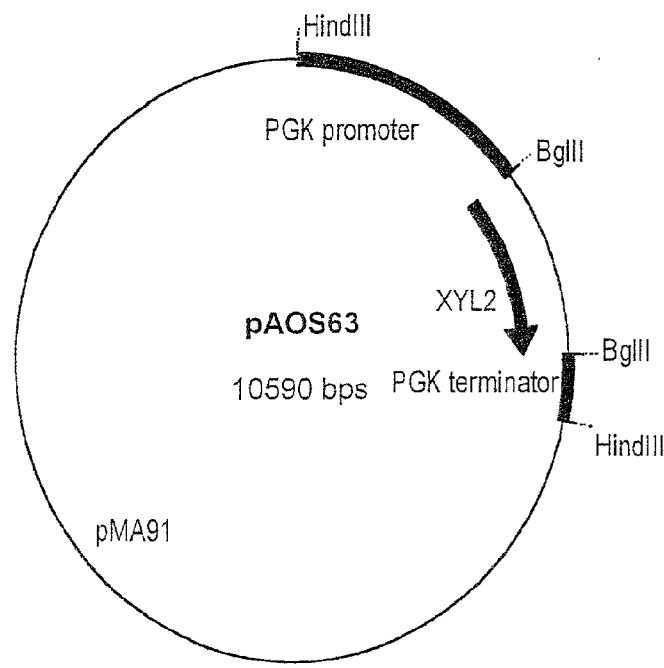
FIG. 11. The genetic map of pAOS 63 with the relevant expression cassette and restriction sites indicated.
Figure 12:
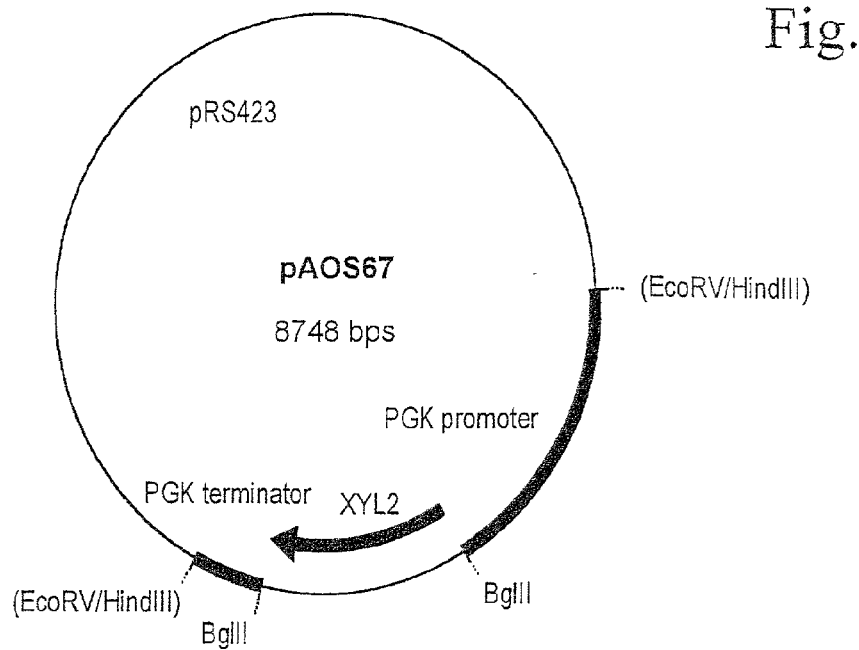
FIG. 12. The genetic map of pAOS 67 with the relevant expression cassette and restriction sites indicated.
Figure 13:
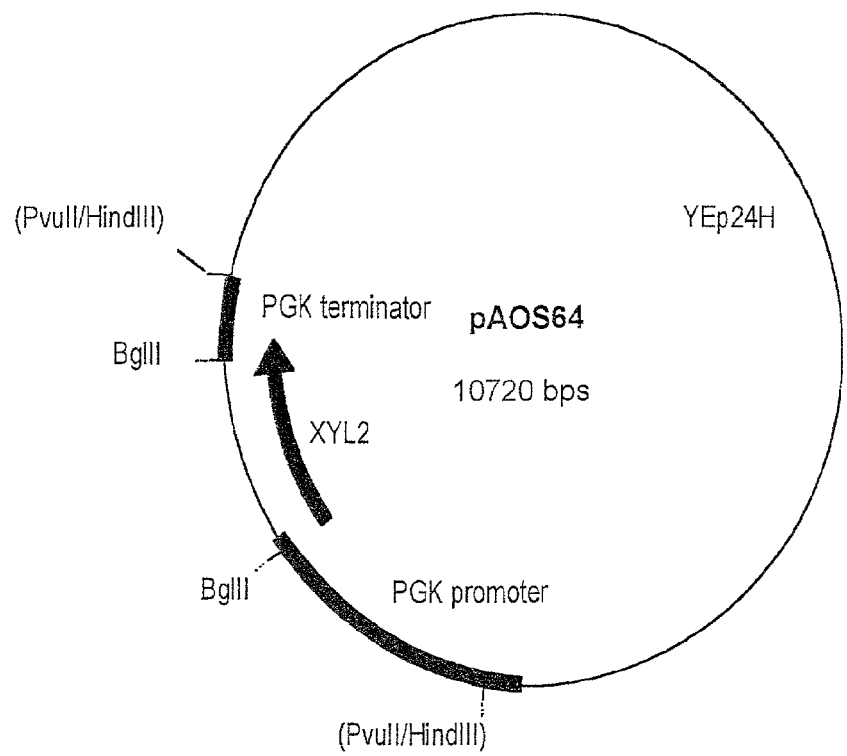
FIG. 13. The genetic map of pAOS 64 with the relevant expression cassette and restriction sites indicated.

The XYL2 gene encoding xylitol dehydrogenase (XDH) from *Pichia stipitis* [Kötter, P., et al., *Curr. Genet.* 18:493–500 (1990)] was cloned into the BglII site of pMA91 expression vector (Mellor, J., et al., *Gene* 24:1–14 (1983)) resulting in plasmid pAOS63 (FIG. 11). The expression cassette, i.e. the XYL2 gene between the PGK promoter and terminator was released from the pMA91 vector as a HindIII fragment, treated with Klenow enzyme and cloned into the EcoRV site of yeast multi-copy vector pRS423 (Christianson, T. W., et al., *Gene* 110:119–122 (1992)) resulting in plasmid pAOS67 (FIG. 12), or into the PvuII site of YEp24H (Aalto, M., et al., *EMBO Journal* 12:4095–4104 (1993)) resulting in plasmid pAOS64 (FIG. 13).

Figure 14:
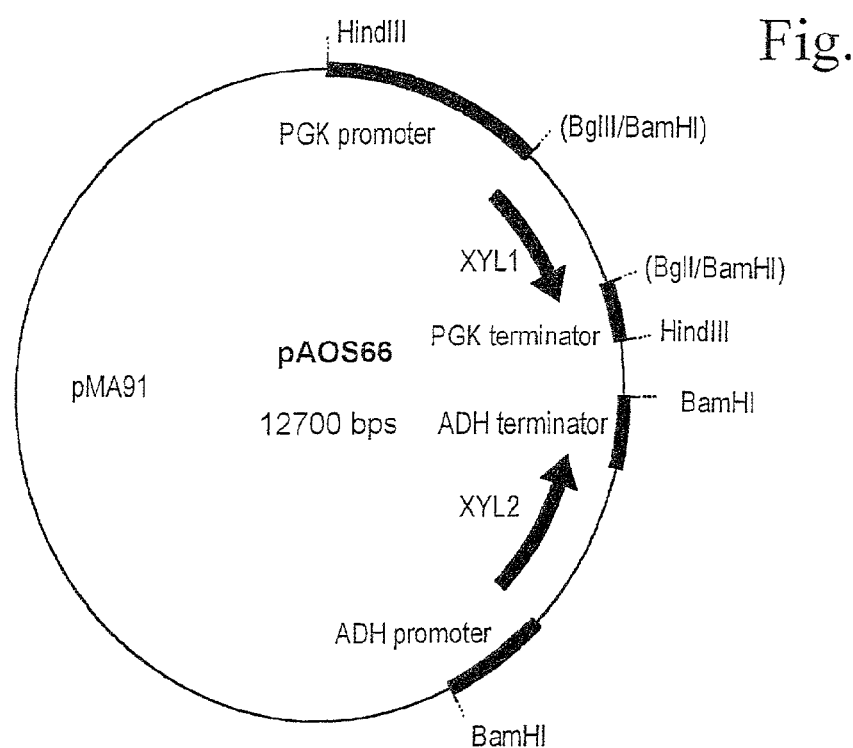
FIG. 14. The genetic map of pAOS 66 with the relevant expression cassette and restriction sites indicated.
Figure 15:
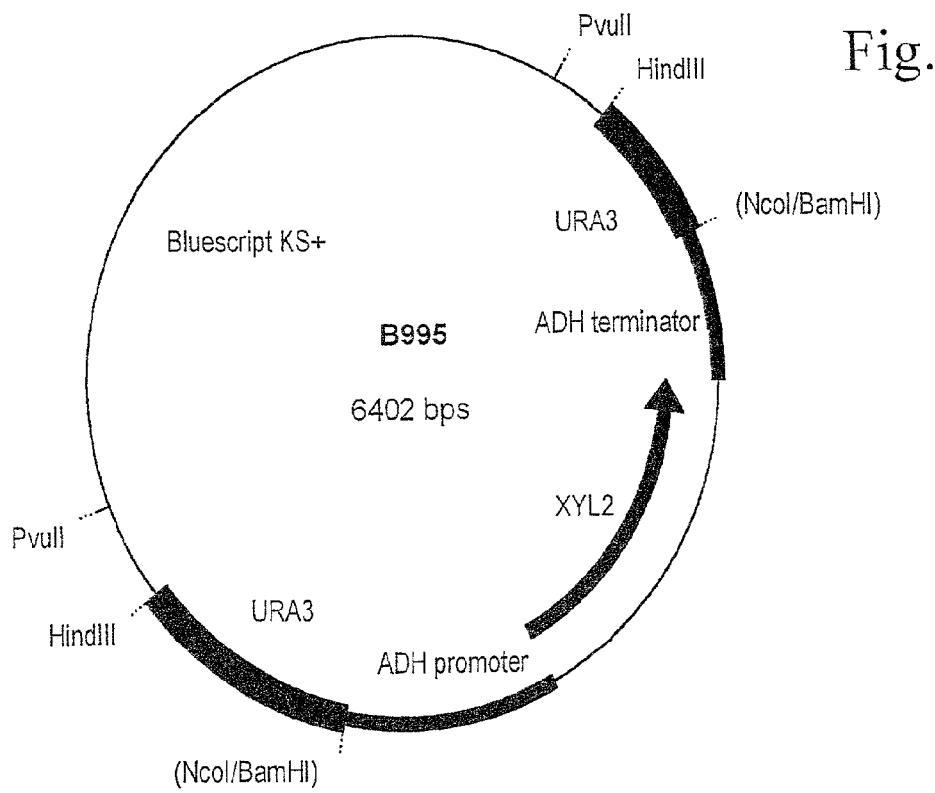
FIG. 15. The genetic map of B995 with the relevant expression cassette and restriction sites indicated.

The vector pAOS66 (FIG. 14) containing from *P. stipitis* both the XYL1 gene encoding xylose reductase (XR) under PGK1 promoter and the XYL2 gene encoding xylitol dehydrogenase (XDH) under modified ADH1 promoter (Ruohonen, L., et al., *J. Biotechnol.* 39:193–203 (1995)) was digested with BamHI and the 2.2 kbp fragment containing the expression cassette for XYL2 gene was isolated from an agarose gel and blunted with Klenow enzyme. Plasmid B713 (URA3 gene as a 1.2 kbp fragment in HindIII site of bacterial cloning vector Bluescript KS (+) multiple cloning site (Stratagene, Calif., USA; URA3 encodes orotidine-5'-P decarboxylase) was digested with NcoI, treated with Klenow enzyme and the XYL2 expression cassette was ligated into the vector. The resulting plasmid B995 (FIG. 15) with XYL2 gene between the modified ADH1 promoter and ADH1 terminator, flanked at both ends by URA3 sequence for targeting to the URA3 locus of the host strain, was digested with PvuII and HindIII enzymes. The HindIII-fragment was purified from an agarose gel with QIAquick method (Qiagen GmbH, Germany). The TKL1,2 deficient yeast strain H1055 was transformed with the fragment, transformants were grown over night on YPD plates and then replica plated onto FOA (5-fluoroorotic acid) plates, to select for ura negative transformants (Cold Spring Harbor Laboratory Press, Methods in yeast genetics, 1994, pp. 188–189). The integration in the transformants was confirmed by measuring XDH activity from the crude cell extracts (for preparation of cell extracts and measurement of XDH activity, see example 15) and by Southern blots. The resulting integrant strain was named H1506.

The XYL2 homologue of *Trichoderma reesei* was derived from the cDNA library constructed in the vector pAJ401 (Saloheimo, A., et al., *Mol. Microbiol.* 13:219–228 (1994)), where the cDNA is ligated between the PGK1 promoter and terminator. Poly(A)+ mRNA was isolated from *T. reesei* Rut-C30 cultivated on medium containing several plant polysaccharides (Stålbrand, H., et al., *Appl. Environ. Microbiol.* 61:1090–1097 (1995)). The cDNA was synthesized using the ZAP-cDNA synthesis kit (Stratagene, Calif., USA) and was ligated into the plasmid pAJ401 (Margolles-Clark, E., et al., *Appl. Environ. Microbiol.* 62:3840–3846 (1996)). *S. cerevisiae* strain H475 carrying the XYL1 gene from *Pichia stipitis* encoding xylose reductase (XR) on the multi-copy plasmid pMA91 [Hallborn, J., et al, *Biol/Technology* 9:1090–1095 (199 1)] was transformed with about 120 µg of the cDNA bank DNA. A yeast cDNA bank of 3.7×10$^5$ independent clones was obtained. The yeast bank was collected in SC-leu-ura media with 20 g/l glucose and plated on SC-leu-ura with 20 g/l xylose plates (5×10$^5$ cells/plate) to screen for the ability to grow on pure xylose plates if both XR and XDH encoding genes are present in the cell. The cDNA bank plasmid was isolated from nine colonies growing on xylose plates and H475 was retransformed with four clones and the ability to grow on pure xylose was reverified. Six clones were sequenced at their 5' ends and four of the clones showed homology to the XYL2 gene encoding xylitol dehydrogenase of *Pichia stipitis*.

Figure 16:
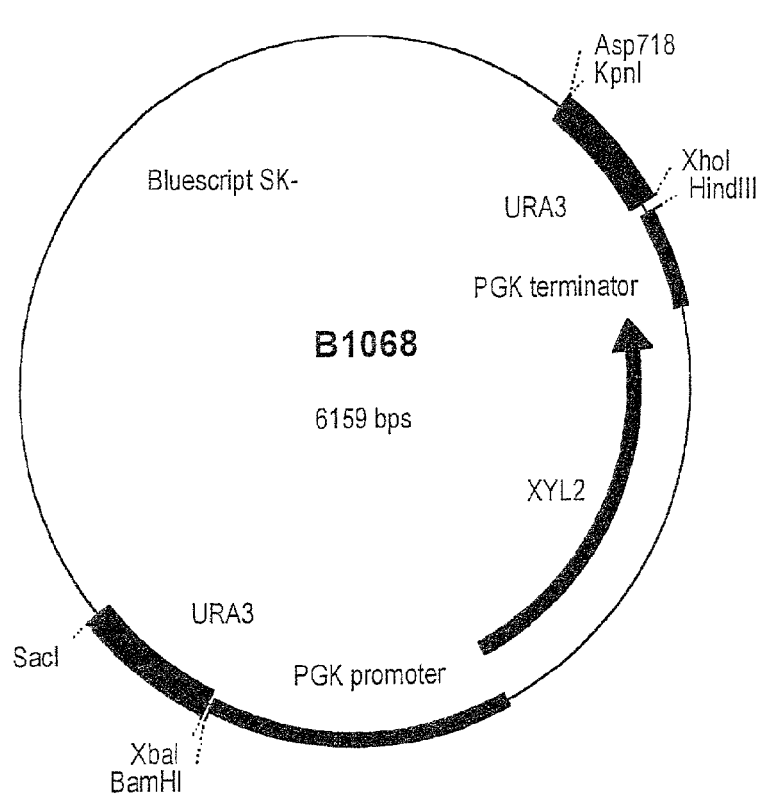
FIG. 16. The genetic map of B1068 with the relevant expression cassette and restriction sites indicated.

The expression cassette of the XYL2 homologue of *T. reesei* in pAJ401 (B1073) between the PGK promoter and terminator was released from the vector with BamHI and HindIII (about 2.5 kbp fragment), and the fragment was purified from an agarose gel using the QIAquick method. The fragment was ligated into the respective sites of YEplac 195, resulting in plasmid B1070, which was transformed into the host H1052, resulting in yeast strain H1748. For construction of an integration cassette the fragment was ligated into the plasmid B955 digested with the HindIII and BamHI. Plasmid B955 (Toikkanen, J. and Keränen, S., submitted for publication (1999)) is Bluescript SK (–) vector carrying two fragments of the URA3 gene; base pairs 71–450 and 781–1135 from the coding region of the gene at SacI-XbaI sites and XhoI-Asp718 sites, respectively, of the polylinker region. The remaining polylinker sites HindIII and BamHI in the cloning vector were used for introducing the XYL2 expression cassette between the two URA3 fragments by sticky-end ligations. The resulting plasmid B1068 (FIG. 16) was 6.2 kbp in size. The expression cassette (5' URA3 71–450 bp—XYL2 expression cassette 5'-3'-URA3 781–1135 3') was released from Bluescript SK (–) by SacI-Asp718 digestion and isolated from an agarose gel. One µg of the fragment was used to transform the TKL1,2 deficient strain H1055. The transformants were selected and verified as described above and named as H1741.

The open reading frame (ORF) YLR070c has high homology to the XYL2 gene of *P. stipitis* and has been shown to code for an enzyme having xylitol dehydrogenase activity [Richard, P., et al., *FEBS Letters* 457:135–138 (1999)). The ORF YLR070c was amplified by PCR from the genomic DNA of yeast W303-1B (renamed as H1104) with an oligonucleotide pair oSCXYL21 (SEQ ID NO: 20) and oSCXYL22 (SEQ ID NO: 21). The PCR product was digested with BamHI, purified from an agarose gel and ligated into the BglII site between the PGK promoter and terminator of pMA91 expression vector. The resulting clone B1163 was transformed into the yeast strain H1104, resulting in strain H1886.

Figure 17:
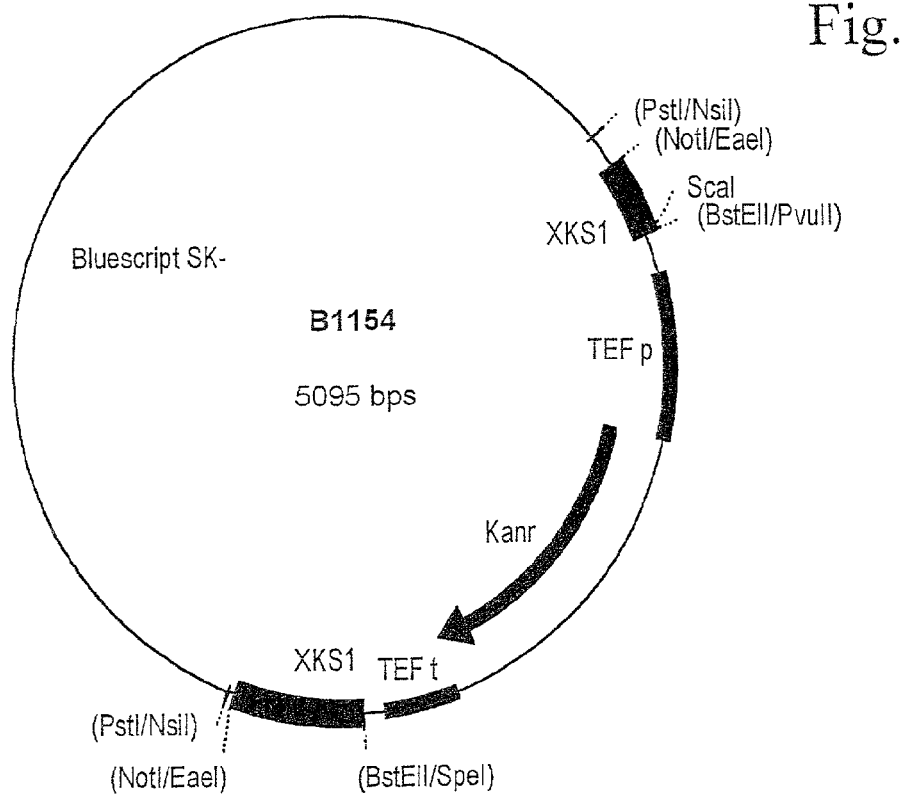
FIG. 17. The genetic map of B1154 with the relevant expression cassette and restriction sites indicated.

The xylulokinase (XK) encoding gene (XKS1, ORF YGR194c) was amplified from the total DNA of yeast strain H1104 by PCR, using an oligonucleotide pair oSCXKS11 (SEQ ID NO: 22) and oSCXKS12 (SEQ ID NO: 23). The PCR product was digested with EcoRV and purified from an agarose gel. The XK encoding fragment was ligated into the cloning vector pRSETC (Invitrogen, The Netherlands) at PvuII site, resulting in plasmid B1025. A deletion cassette was constructed by first moving a 1 kbp EaeI fragment of XKS1 from B1025 to the compatible NotI site in pZErO™-1 vector (Invitrogen) followed by a ScaI digestion to remove a 500 bp fragment from the middle of the XKS1 sequence. The XKS1 fragment with the ScaI deletion was moved from this vector as a NsiI fragment to the PstI site of Bluescript SK (–). The kanMX2 fragment from the pFA6-kanMX2 plasmid [Wach, A., et al., *Yeast* 10:1793–1808 (1994)] was released from the vector as a PvuII-SpeI fragment and cloned by blunt end ligation to the BstEII site in the XKS1 sequence, resulting in plasmid B1154 (FIG. 17). The disruption cassette of the B1154 was amplified by PCR with an oligonucleotide pair oSCXKS13 (SEQ ID NO: 24) and oSCXKS14 (SEQ ID NO: 25). The fragment was transformed into the TKL1,2 deficient strain harboring the XDH encoding gene from *P. stipitis* integrated into the genome (H1506). Xylulokinase deficient transformants were screened on YPD plates containing 200 mg/l of the antibiotic G418. The disruption was confirmed by PCR and Southern blots. The resulting strain was named as H1854.

Example 13

Accumulation of 5-carbon Sugar Phosphates in a Transketolase Deficient Strain of *Saccharomyces Cerevisiae*

The sugar phosphates were measured from the TKL1,2 deficient strain (H1055) and the host strain (H1104). The cells were grown on SCD medium to an optical density (OD) 600 of 1.4 (H1055) and 4.0 (H1104), collected, washed once with water and suspended to PBS buffer (phosphate buffered saline, 150 mM NaCl, pH6.7) into a density of 0.2 g of wet weight/ml. Glucose was added to a concentration of 20 g/l and after 20 minutes the cells were rapidly quenched in cold methanol and extracted with the methanol/chloroform procedure (de Koning, W., and van Dam, K., *Anal. Biochem.* 204:118–123 (1992)).

Enzymatic analyses were performed to quantify the 5-carbon sugar phosphates. Xylulose-5-phosphate, ribulose-5-phosphate and ribose-5-phosphate were measured basically as described by Bergmeyer [Methods in enzymatic analysis, Vol. 3 (1974) Verlag Chemie, Academic Press]. Xylulose-5-phosphate was determined in 0.1 M TEA (triethanol amine) buffer, pH 7.2, with 0.15 mM Ribose-5P, 0.22 mM NADH, 25 U of glyceraldehyde-3-phosphate isomerase (TPI), 0.85 U of glycerol-3P dehydrogenase (G3PDH). The reaction was started with transketolase (TKL) enzyme (Sigma, USA), final concentration of 1.2 U/ml. The decrease of absorbance at 340 nm was monitored. Enzymes, except for transketolase were purchased from Boehringer Mannheim (Germany). Ribulose-5P was measured as described for xylulose-5P, except that the reaction was started with xylulose-5P epimerase (Sigma USA), which converts ribulose-5-phosphate to xylulose-5-phosphate. Final concentration of xylulose-5P epimerase was 2 U/ml. Ribose-5P was measured as xylulose-5P, except that instead of using ribose-5P in excess, xylulose-5P (Sigma) was added. The intracellular concentrations of sugar phosphates were calculated according to Gancedo and Serrano [Gancedo, C. and Serrano, R., The Yeasts, vol 3, eds. Rose A. H. and Harrison J. S., pp 205–260, Academic Press Ltd., London, (1989)]. Results are shown in Table 4.

TABLE 4

Accumulation of 5-carbon sugar phosphates in the TKL1,2 deficient strain H1055 and the host strain H1104

| Strain | Xylulose-5-P (mM) | Ribulose-5-P (mM) | Ribose-5-P (mM) |
|---|---|---|---|
| TKL1,2 deficient strain (H1055) | 0.50 | 0.38 | 0.71 |
| host strain (H1104) | 0.02 | 0.14 | 0.34 |

In this particular experiment xylulose-5P (X5P) levels were 25 fold higher in the TKL deficient strain and ribulose-5P (Ru5P) and ribose-5P (Ri5P) concentrations were 2–3 fold higher as compared to the host strain. The experiment discloses that five carbon sugar phosphates accumulate in the TKL deficient strain to a higher level as compared with the host yeast strain.

Example 14

Production of Polyols and Pentoses by a Transketolase Deficient Strain of *Saccharomyces Cerevisiae*

The host strain H1104 and the TKL1,2 deficient strain H1055 were cultivated in yeast minimal medium. Pre-cultures were grown in SCD medium to an OD600 of 3–5, cells were collected by centrifugation and washed once with water and resuspended to an OD600 of 0.1 for the cultivation experiment on the yeast minimal medium. Samples were withdrawn during cultivation at time points indicated, OD600 measured, cells removed by centrifugation and the growth media samples analyzed for polyols by the D-sorbitol/xylitol colorimetric method of Boehringer Mannheim. Results are shown in Table 5. Sorbitol dehydrogenase (SDH) used in this analytical kit oxidizes D-sorbitol and xylitol, and with a lower velocity, e.g., not quantitatively, other polyols such as ribitol, iditol and allitol. OD600 1.0 corresponds to 0.3 g/l of cell dry weight.

TABLE 5

Polyols produced by the TKL 1,2 deficient strain H1055 and the host strain H1104.

| | Polyols g/g cell dry weight[1] | | | | | | | | |
|---|---|---|---|---|---|---|---|---|---|
| Strain | 8 h[2] | 23 h | 29 h | 47 h | 53 h | 71 h | 77 h | 95 h | 101 h |
| host strain H1104 | 0 | 0.005 | 0.008 | 0.008 | 0.008 | 0.008 | 0.006 | 0.009 | 0.009 |
| TKL1,2 deficient strain H1055 | 0.046 | 0.081 | 0.098 | 0.131 | 0.140 | 0.148 | 0.146 | 0.178 | 0.173 |

[1]Polyols measured with Boehringer Mannheim D-sorbitol/xylitol kit
[2]The time point in hours of the growth medium sample withdrawn A 15 to 20-fold increase in polyol production was observed with the TKL1,2 deficient strain H1055 as compared to the host strain HI 104.

The growth media samples of 29 h, 53 h and 101 h were also analyzed by HPLC. Prior to the analysis, the samples were concentrated 5-fold by lyophilization. DIONEX DX-500 device was used with CarboPac PA-10 column (30° C., flow rate 1 ml/min; eluents A=water, B=100 mM NaOH, C=300 mM Na-acetate/100 mM NaOH, D=300 mM NaOH; the gradient elution was as follows: 100% A at 21 h, 100% B at 40 h, 50% B+50% C at 60 h, 100% C at 60.10 h, 100% C at 64 h, 100% D at 64.10 h, 100% D at 67 h, 100% A at 67.10 h, 100% A at 82 h). Ribulose and xylulose co-eluted under the analysis conditions used. Results are shown in Table 6.

TABLE 6

Polyols (xylitol and ribitol) and 5-carbon sugars produced by
the TKL1,2 deficient strain H1055 and the host strain H1104.

| | 29 h[1] | | | 53 h | | | 101 h | | |
|---|---|---|---|---|---|---|---|---|---|
| Strain | Xol + Rol[2] | Ribo[3] | Ribu + Xylu[4] | Xol + Rol | Ribo | Ribu + Xylu | Xol + Rol | Ribo | Ribu + Xylu |
| TKL1,2 deficient H1055 | 0.095 | 0.067 | 0.413 | 0.144 | 0.094 | 0.497 | 0.157 | 0.122 | 0.532 |
| host H1104 | — | — | — | — | — | — | 0.004 | 0.001 | 0.013 |

[1] The time point in hours of the growth medium sample withdrawn;
[2] Xylitol + ribitol g/g cell dry weight;
[3] Ribose g/g cell dry weight;
[4] Ribulose + xylulose g/g cell dry weight The HPLC results show that polyol production was increased by a factor of 40 in the TKL1,2 deficient strain as compared to the host strain. In addition, the production of 5-carbon sugars was markedly increased, being 175- and 40-fold for ribose and ribulose+xylulose, respectively. Less than 1–2% of polyols were arabitol, mannitol or sorbitol (the latter determined in another experiment, data not shown), disclosing that polyols produced by the TKL1,2 deficient strain were ribitol and xylitol.

Example 15

Production of Polyols and Pentoses by Transketolase Deficient Strains of *Saceharomyces Cerevisiae* Harboring the Xylitol Dehydrogenase (XDH) Encoding Gene from *Pichia Stipitis* Either on a Multi-copy Plasmid or Integrated into the Genome, or from *Trichoderma Reesei* Integrated into the Genome a) Production of Polyols by a TKL1 Deficient Strain of *Saccharomyces Cerevisiae* Harboring the XDH Encoding Gene from *Pichia stipitis* on a Multi-copy Plasmid Yeast strains deficient in transketolase activity are auxotrophic for aromatic amino acids as the precursor for their synthesis, erythrose-4-phosphate is not synthesized in a TKL1,2 deficient strain. It may be beneficial if part of the glucose could also support the maintenance of the cells. This is possible in a strain where only the major isoform of the transketolases, TKL1 is disrupted.

A TKL1 deficient strain H1764 and the equivalent host strain H1346 (see Appendix I, Table 32) were transformed with a multi-copy vector harboring the XDH encoding gene from *P. stipitis* (pAOS67; FIG. 12) resulting in strains H1765 and H1766, respectively. The strains obtained were cultivated in SCD medium lacking histidine for plasmid selection. Samples were taken at time points indicated, cells were centrifuged and the growth medium analyzed for polyols by the Boehringer Mannheim D-sorbitol/xylitol kit. Results are shown in Table 7.

TABLE 7

Polyol (xylitol + ribitol) production by the TKL1 deficient strain
H1765 and the host strain H1766 carrying the multi-copy vector pAOS67
with the XDH encoding gene from *P. stipitis*

| | Polyols g/g cell dry weight | | | |
|---|---|---|---|---|
| Strain | 13 h[1] | 19 h | 37 h | 69 h |
| TKL1 deficient pAOS67 H1765 | 0.010 | 0.016 | 0.014 | 0.014 |
| host pAOS67 H1766 | 0.006 | 0.008 | 0.007 | 0.005 |

[1] The time point in hours of the growth medium sample withdrawn

A 2-fold increase in polyol production (g polyols/g cell dry weight) was observed in the TKL1 deficient strain as compared to the wild type throughout the cultivation period of 70 h. This experiment discloses that an increase in polyol production is obtained with a yeast strain deficient in only one of the transketolase isoforms, TKL1.

b) Production of Polyols and Pentoses by a TKL1,2 Deficient Strain of *Saccharomyces cerevisiae* Harboring the XDH Encoding Gene from *Pichia stipitis* on a Multi-copy Plasmid The host strain H1104 and the TKL1,2 deficient strain H1055 were transformed with a multi-copy vector harboring the XDH encoding gene from *P. stipitis* (pAOS67; FIG. 12) resulting in strains H1160 and H1057, respectively (Appendix I, Table 32). The strains obtained were cultivated on the yeast minimal medium. Pre-cultures were grown on SCD medium lacking histidine for plasmid selection to an OD600 of 3–5, cells were collected by centrifugation and washed once with water and resuspended to an OD600 of 0.1 for the cultivation experiment on the yeast minimal medium. Samples were withdrawn during cultivation at time points indicated, cells removed by centrifugation and the growth media samples analyzed for polyols by the D-sorbitol/xylitol kit of Boehringer Mannheim and by HPLC (see example 14). The results are shown in Table 8.

TABLE 8

Polyol (xylitol + ribitol) production by the TKL1,2 deficient strain H1055 and the host strain H1104, and equivalent strains H1057 and H1160, respectively carrying the multi-copy vector pAOS67 with the XDH encoding gene from *P. stipitis*

| Strain | 29 h[1] | | | 53 h | | | 101 h | | |
|---|---|---|---|---|---|---|---|---|---|
| | Polyols[2] | Xylitol[3] | Ribitol[3] | Polyols | Xylitol | Ribitol | Polyols | Xylitol | Ribitol |
| host H1104 | 0.008 | — | — | 0.008 | — | — | 0.009 | — | — |
| TKL1,2 deficient H1055 | 0.098 | — | — | 0.140 | — | — | 0.173 | — | — |
| host pAOS67 H1160 | 0.025 | — | — | 0.030 | — | — | 0.031 | — | — |
| TKL1,2 deficient pAOS67 H1057 | 0.346 | 0.043 | 0.331 | 0.463 | 0.051 | 0.441 | 0.738 | 0.077 | 0.611 |

[1]The time point in hours of the growth medium sample withdrawn
[2]Polyols ribitol + xylitol (g/g cell dry weight) measured with Boehringer Mannheim sorbitol/xylitol kit
[3]Xylitol and ribitol (g/g cell dry weight) determined by HPLC (DIONEX DX 500, CarboPack PA-10)

As discussed in example 14, a 15- to 40-fold increase in polyol production was observed with the TKL1,2 deficient strain H1055 as compared to the host strain H1104. A further increase of about 5-fold was obtained when the XDH encoding gene of *P. stipitis* was expressed on a multi-copy plasmid in the TKL1,2 deficient strain. The polyol fraction consisted of xylitol and ribitol, and mainly of ribitol, only about 10 to 15% of the polyols was xylitol in this experiment.

The growth media samples were also analyzed for 5-carbon sugars by HPLC (see example 14). Results are shown in Table 9.

The increase in ratios in the TKL1,2 deficient strain was 40-, 175-, and 40-fold for polyols (ribitol+xylitol), ribose and ribulose+xylulose, respectively (see example 14), whereas the respective increases were 220-, 130- and 75-fold in the presence of the XDH encoding gene, demonstrating a shift in the ratios towards polyols and xylulose+ribulose.

Over-expression of XDH encoding gene from *P. stipitis* on a multi-copy vector resulted in a significant change in the ratios of polyols and 5-carbon sugars as compared to the TKL1,2 deficient strain alone. The amount of 5-carbon sugars is decreased 1.4- to 2-fold, whereas the increase in polyols is 4 fold (see Table 10).

TABLE 9

Polyols (xylitol and ribitol) and 5-carbon sugars produced by the TKL1,2 deficient strain and the host strain carrying the multi-copy vector pAOS67 with the XDH encoding gene from *P. stipitis*, H1057 and H1160, respectively.

| Strain | 29 h[1] | | | 53 h | | | 101 h | | |
|---|---|---|---|---|---|---|---|---|---|
| | Xol + Rol[2] | Ribo[3] | Ribu + Xylu[4] | Xol + Rol | Ribo | Ribu + Xylu | Xol + Rol | Ribo | Ribu + Xylu |
| TKL1,2 deficient pAOS67 H1057 | 0.374 | 0.033 | 0.224 | 0.492 | 0.049 | 0.310 | 0.688 (220)[5] | 0.079 (130) | 0.385 (75) |
| host pAOS67 H1160 | — | — | — | — | — | — | 0.0031 | 0.0006 | 0.0050 |

[1]The time point in hours of the growth medium sample withdrawn
[2]Xylitol + ribitol g/g cell dry weight (results from Table 8)
[3]Ribose g/g cell dry weight
[4]Ribulose + xylulose g/g cell dry weight
[5]The increase in production (x-fold) by TKL1,2 deficient strain as compared to the host strain

TABLE 10

The ratios of polyols (xylitol and ribitol) and 5-carbon sugars in the TKL1,2 deficient strain H1055 and the strain carrying the multi-copy vector pAOS67 with the XDH encoding gene from *P. stipitis*, H1057

| Strain | 29 h[1] | | | 53 h | | | 101 h | | |
|---|---|---|---|---|---|---|---|---|---|
| | Xol + Rol (%)[2] | Ribo (%)[3] | Ribu + Xylu (%)[4] | Xol + Rol (%) | Ribo (%) | Ribu + Xylu (%) | Xol + Rol (%) | Ribo (%) | Ribu + Xylu (%) |
| TKL1,2 deficient pAOS67 H1057 | 59 | 5 | 35 | 58 | 6 | 36 | 60 | 7 | 33 |
| TKL1,2 deficient H1055 | 17 | 12 | 72 | 20 | 13 | 68 | 19 | 15 | 66 |

[1]The time point in hours of the growth medium sample withdrawn
[2]Xylitol and ribitol ratio in % of total polyols and 5-carbon sugars produced
[3]Ribose ratio in % of total polyols and 5-carbon sugars produced
[4]Ribulose and xylulose ratio in % of total polyols and 5-carbon sugars produced c) Alteration of Polyol Ratios Produced in a TKL1,2 Deficient Strain by Expressing Genes Encoding XDH Enzymes with Different Substrate Specificities The xylitol dehydrogenases of *P. stipitis*, *Trichoderma reesei* and *S. cerevisiae* were investigated regarding their specificities towards their sugar substrates. Each of the XDH encoding genes was expressed on multi-copy vectors pAOS67, B1070 and B1163, respectively (see Example 12). Yeast strain H1104 (pAOS67, B1163) and H1052 (B1070) harboring each of the multi-copy vectors, H1160, H1886 and H1748, respectively, were cultivated on SCD medium lacking the appropriate selection marker (histidine, leucine, uracil, respectively). Cells were collected by centrifugation and washed twice with 100 mM sodium phosphate buffer pH 7.0. Cells were resuspended at a concentration of 500 mg/ml wet weight, corresponding approximately to 75 mg/ml dry weight, in the same buffer. 1 ml of this suspension was vortexed with 1 g glass beads (0,5 mm Ø) for 15 min. at 4° C., centrifuged in an Eppendorf centrifuge (13,000 rpm) and the supernatant was assayed. XDH activity was assayed in a medium containing 50 mM Pipes KOH pH 7.0, 0.2 mM NADH. The reaction was started by addition of D-xylulose or D-ribulose at a final concentration of 1 mM. The activity was measured by following the adsorption of NADH at 340 nm. Results are shown in Table 11.

TABLE 11

The specific activities of three fungal XDH enzymes towards D-xylulose and D-ribulose at concentrations of 1 mM. Activities are normalized to D-xylulose activity being 100%.

| | Xylulose | Ribulose |
|---|---|---|
| *Pichia stipitis* XDH | 100 | 25 |
| *Trichoderma reesei* XDH | 100 | 5 |
| *Saccharomyces cerevisiae* XDH | 100 | 10 |

This example discloses that the XDH enzymes from *T. reesei* and *S. cerevisiae* have a higher specificity towards D-xylulose than the XDH enzyme from *P. stipitis*.

The XDH encoding gene homologues from *P. stipitis* and *T. reesei* were integrated into the genome of the TKL1,2 deficient strain H1055 as described in Example 12, resulting in strains H1506 and H1741, respectively. Cells were cultivated in SCD medium and samples taken at time points indicated. Cells were centrifuged and growth medium samples analyzed for polyols (xylitol and ribitol). Total polyols were analyzed with D-sorbitol/xylitol kit of Boehringer Mannheim, with the addition of 0.07 U/ml of purified ribitol dehydrogenase (RDH) from *Klebsiella pneumoniae* to quantitatively measure the amount of ribitol (Bergmeyer H. U., "Methods in Enzymatic Analysis," in *Verlag Chemie Vol* 3', Academic Press (1974), pp. 1356–1358). Ribitol was measured with the RDH alone, and the amount of xylitol was obtained by subtracting the amount of ribitol from the amount of total polyols. The assay conditions for ribitol were the following: To 200 μm reagent containing 450 mM TrisHCl pH 8.7, 5 mM NAD and 0.07 U/ml ribitol dehydrogenase, the sample was added and water to have a total volume of 250 μl. The solution was incubated for 20 minutes at 37° C. The absorbance differences before sample addition and after incubation were compared to a standard curve, including a zero control, which was measured under exact the same conditions. All analyses were performed on a Cobas Mira Plus automated analyzer (Roche). Results are shown in Table 12.

TABLE 12

Xylitol and ribitol (g/g cell dry weight) produced by TKL1,2 deficient strain H1055 harboring the XDH encoding gene of *P. stipitis* (H1506) or *T. reesei* (H1741) integrated into the genome.

| | 24 h[1] | | | 44 h | | | 68 h | | | 106 h | | |
|---|---|---|---|---|---|---|---|---|---|---|---|---|
| Strain | Xol[2] | Rol[2] | Xol/Rol[3] | Xol | Rol | Xol/Rol | Xol | Rol | Xol/Rol | Xol | Rol | Xol/Rol |
| H1506 P. s XDH | 0.097 | 0.093 | 1.0 | 0.141 | 0.194 | 0.7 | 0.161 | 0.335 | 0.5 | 0.075 | 0.375 | 0.2 |
| H1741 T. r XDH | 0.086 | 0.069 | 1.2 | 0.128 | 0.119 | 1.1 | 0.158 | 0.133 | 1.2 | 0.203 | 0.142 | 1.4 |

[1] The time point in hours of the growth medium sample withdrawn
[2] Xylitol (Xol) or ribitol (Rol) g/g cell dry weight
[3] Xylitol/ribitol ratio This experiment discloses how the polyol product spectrum can be controlled by choosing an appropriate polyol dehydrogenase, and how polyol dehydrogenases can be characterized by in vitro measurements. By over-expressing the gene for a suitable dehydrogenase the Xol/Rol ratio can be manipulated in the desired direction.

d) Polyol Production by a TKL1,2 Deficient Strain Inactivated in the XK Encoding Gene The xylulokinase (XK) encoding gene was disrupted from the TKL1,2 deficient strain containing the chromosomal integration of *P. stipitis* XDH encoding gene H1506, resulting in strain H1854 as described in example 12.

The cells were gown on SCD medium for 2 days. The pre-culture was diluted 1:50 into fresh cultivation medium and further grown for additional 20 h. The cells were collected by centrifugation and washed once with water and suspended into 1 ml of water. The cultivation on SCD medium was started by adding cells to an OD600 of 0.2. Samples were collected after cultivation time of 100 h, OD600 measured, cells removed by centrifugation and growth medium samples analyzed for xylitol and ribitol by D-sorbitol/xylitol Boehringer Mannheim kit with RDH and by the specific ribitol assay (see previous example). Results are shown in Table 13.

TABLE 13

Xylitol and ribitol production (g/g cell dry weight) by TKL1,2 deficient strain with the XDH encoding gene from *P. stipitis* integrated into the genome (H1506) and additionally inactivated in the XK encoding gene (H1854).

| Strain | Xylitol[1] | Ribitol[1] | Xylitol/Ribitol[2] |
|---|---|---|---|
| TKL1,2 deficient, P. stipitis XDH H1506 | 0.154 | 0.726 | 0.21 |
| TKL1,2 deficient XK deficient P. stipitis XDH H1854 | 0.375 | 0.542 | 0.69 |

[1] Xylitol or ribitol g/g cell dry weight
[2] Xylitol/ribitol ratio

The XK deficient strain H1854 produces more xylitol and less ribitol as compared to the H1506 strain. The proportion of xylitol has increased from 18% to 40%. The total amount of ribitol and xylitol did not change significantly in this experiment, but the ratio favors xylitol. This experiment discloses that disruption of XK encoding gene alters the polyol ratio.

Example 16

Cloning of DOG1 Encoding Gene from *Saccharomyces Cerevisiae* and of LTP1 Homologues from *S. cerevisiae* and *Zygosaccharomyces Rouxii*

The 2-deoxyglucose-6-phosphate phosphatase (DOG1) encoding gene DOG1 in the vector YEplac 181 (YEp11HP, [Sanz, P. et al, Yeast 10:195–1202 (1994)] renamed as B1016), was obtained from Dr. Sanz. The DOG1 gene from the B1016 plasmid was amplified by PCR with an oligonucleotide pair oDOG11 (SEQ ID NO: 26) and oDOG12 (SEQ ID NO: 27). The PCR fragment was digested with HindIII and purified from an agarose gel. The fragment was ligated into the HindIII site between the modified ADH1 promoter and ADH1 terminator in Bluescribe M13 (B609 Appendix I, Table 33). The resulting clone was digested with BamH1 and PvuII and the BamHI-fragment containing the ADH1 promoter-DOG1- ADH1 terminator was extracted from an agarose gel and cloned into BamHI site of YEplac 195 multi-copy vector (Gietz and Sugino, Gene 74:527–534 (1988)), resulting in plasmid B1020. Plasmid B1020 was transformed into the TKL1,2 deficient strain harboring the XDH encoding gene from *P. stipitis* integrated into the genome (H1506), resulting in strain H1520. A control strain containing the same vector (YEplac 195) without DOG1 was named as H1524. Plasmid B1020 was also transformed into the host strain H1104, resulting in strain H1514.

In order to construct a *Zygosaccharomyces rouxii* genomic library, the chromosomal DNA of *Z. rouxii* was isolated using the standard methods, partly digested with Sau3A, and DNA fragments larger than 2 kb were isolated from this digest by preparative agarose gel electrophoresis. *E. coli-S. cerevisiae* shuttle vector pL3 (Ianushka, A. P., Genetika. 24(5):773–80 (1988)), received from K. Sasnauskas (Institute of Biotechnology, Vilnius, Lithuania) was digested with BamHI, treated with calf intestinal phosphatase and ligated with the Sau3A fragments of the *Z.rouxii* chromosomal DNA. This ligation mixture was used to transform *E. coli* strain HB101 (Stratagene, La Jolla USA). About 20,000 transformants were obtained with estimated 60–70% of clones containing inserts of *Z. rouxii* DNA. The transformants were pooled and plasmid DNA was isolated from several such pools by the standard methods. The quality of the library was checked by its ability to complement several standard auxotrophic mutations (HIS3, URA3, ADE1) in laboratory strains of *S. cerevisiae*.

The genomic library of *Z. rouxii* was transformed into the TKL1 deficient strain of *Saccharomyces cerevisiae* (H1764, see example 12) and 10,000 independent clones were obtained. We have observed that the TKL1 deficient strain H1764 is unable to grow on 2% galactose plates containing 0.3% or higher concentrations of D-xylulose (probably due to toxic concentrations of 5-carbon sugar phosphates accumulating). The independent clones were plated with 0.5% D-xylulose (synthetic complete medium with 2% galactose, 0.5% xylulose and 3% xylose lacking leucine for selection of the library plasmid) and screened for complementation of growth on these plates.

The screening of *Z. rouxii* genomic library resulted in six positive clones, which were able to grow after 7 days on the plates described above. The library plasmids were rescued from the yeast colonies and analyzed by restriction enzyme digestions and sequencing. According to restriction enzyme patterns and sequence data, the six plasmids contain two different genomic fragments of *Z. rouxii*. Both genomic fragments contain an ORF having high homology to the TKL1 encoding gene of *S. cerevisiae*. The two ORFs were named as TKL1 and TKL2 of *Z. rouxii*.

Sequencing analysis of the genomic clones revealed (280 bp downstream from both TKL genes) another ORF which was 483 bp long encoding a polypeptide of 160 amino acid residues. Identity between these two ORFs (one from each genomic clone; named PPPase 1 which is downstream from TKL1 of *Z. rouxii* (SEQ ID NO:38) and PPPase 2 which is downstream from TKL2 of *Z. rouxii* (SEQ ID NO:40), respectively) was 94%. Blast search (Altschul, S. F. et al, See: www.ncbi.nlm.nih.gov/blast/(1997)) by using amino acid sequences encoded by PPPase 1 (SEQ ID NO:39) and PPPase 2 (SEQ ID NO:41) of *Z. rouxii* as templates resulted in several homologues from other species including yeasts (Table 14). Characteristic to all these homologous amino acid sequences is that 1) the protein encoded by the homologous gene belongs to the protein-tyrosine-phosphatase (EC 3.1.3.48) and/or to acid phosphatase (EC 3.1.3.2) protein families. 2) The size of the protein encoded by the gene is approximately 17–20 kDa and 3) the protein encoded by the gene shares a common active site motif CXXXXXR of low molecular weight protein-tyrosine phosphatases (C=cysteine, X=any amino acid and R=arginine) in the amino terminal part of the protein.

TABLE 14

The most homologous counterparts in other yeasts of the PPPase 1 and PPPase 2 of *Z. rouxii*.

| Yeast | ORF | Protein | Identity % | Accession number(s) |
|---|---|---|---|---|
| Candida albicans | | | 58[1] (59)[2] | AL033501 |
| Saccharomyces cerevisiae | LTP1 | low molecular weight protein-tyrosine phosphatase | 57 (58) | e.g. P40347, U11057, L48604, AAA80146, CAA89190, AAB68124 |
| Schizosaccharomyces pombe | stp1 | small tyrosine phosphatase | 50 (50) | P41893, A55446, AAA61930 |

[1]Identity to *Z. rouxii* PPPase 1.
[2]Identity to *Z. rouxii* PPPase 2.

Figure 18:
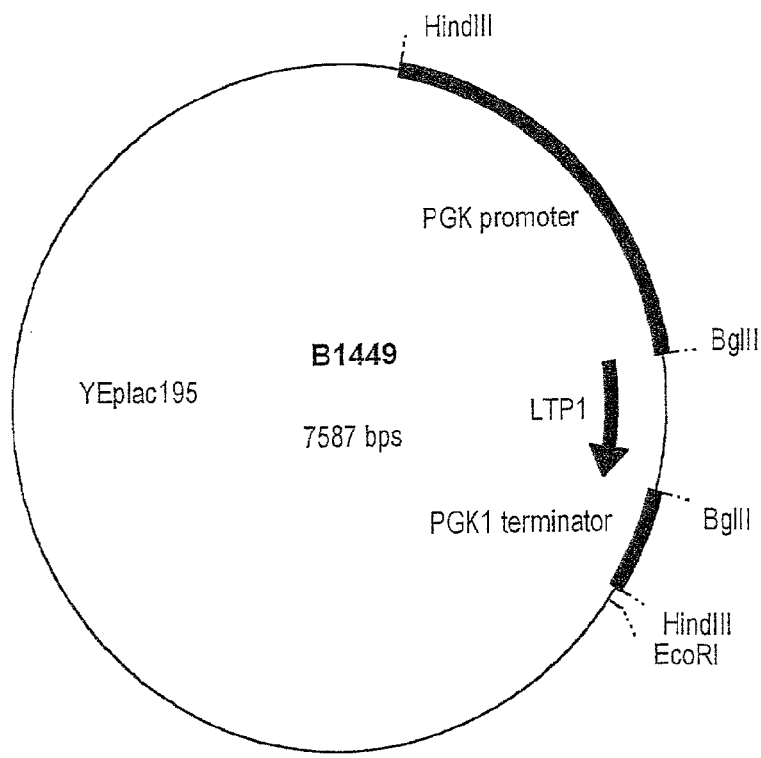
FIG. 18. The genetic map of B1449 with the relevant expression cassette and restriction sites indicated.

To construct an over-expression plasmid with the LTP (Low Molecular Weight Protein-Tyrosine Phosphatase) encoding gene from *S. cerevisiae*, the expression vector pMA91 was digested with HindIII and the 1.8 kb fragment containing the PGK1 promoter and terminator was isolated from an agarose gel. The promoter-terminator cassette was ligated into the YEplac195 vector which had been linearized at its multi-cloning site with HindIII, resulting in plasmid B1181. The orientation of the promoter-terminator fragment in the expression vector is HindIII-PGK1 promoter-PGK1 terminator EcoRI. The LTP 1 encoding gene from *S. cerevisiae* (YPR073C) was amplified by PCR from the genomic DNA of H475 (Appendix I, Table 32) using an oligonucleotide pair oScLTP5 (SEQ ID NO: 28) and oScLTP3 (SEQ ID NO: 29) as primers. The PCR reaction was 30 cycles, 45 sec at 95° C., 45 sec at 45° C. and 2 min at 72° C. with a final extension of 0 min at 72° C. The PCR product was purified with QIAquick PCR Purification Kit (Qiagen, Germany) and digested with BglII (sites introduced to the fragment during PCR synthesis), and ligated into the BglII site of B1181, resulting in plasmid B1449 (FIG. 18). The plasmid was transformed into the TKL1,2 deficient strain of *S. cerevisiae* harboring the XDH encoding gene from *T. reesei* integrated into the genome (H1741) (see example 12). The yeast transformant containing the B1449 plasmid was named as H2422. To obtain a control strain over-expression plasmid B11181 was transformed into H1741 and the resulting strain was named as H2421.

To construct an over-expression plasmid with the PPPase 2 encoding gene from *Z. rouxii*, the expression vector B1181 was used. A PCR fragment was made using the genomic fragment of *Z. rouxii* containing the PPPase 2 gene as a template and an oligonucleotide pair oZrPPPase5 (SEQ ID NO: 30) and oZrPPPase3 (SEQ ID NO: 31) as primers. After the PCR reaction (30 cycles, 45 sec at 95° C., 45 sec at 45° C. and 2 min at 72° C. with final extension at 72 for 10 min) the PCR product was purified with QIAquick PCR Purification Kit and digested with BamHI (sites introduced to the fragment during PCR synthesis) and ligated into the BglII site of B1181, resulting in plasmid B1450. The plasmid was transformed into the TKL1,2 deficient strain of *S. cerevisiae* harboring the XDH encoding gene from *T. reesei* integrated into the genome (H1741) (see example 12). The yeast transformant containing the B1450 plasmid was named as H2424.

Example 17

Increase in Production of Pentoses and Pentitols in Strains of *Saccharomyces Cerevisiae* Over-expressing the Genes Encoding the Phosphatases DOG1 and LTP1 a) Increased Production of Polyols and Pentoses in the TKL1,2 Deficient Strain Over-expressing the DOG1 Gene Encoding a Phosphatase The DOG1 gene of *S. cerevisiae* encoding the 2-deoxyglucose-6-phosphatase was over-expressed in the TKL1,2 deficient strain with the XDH encoding gene from *P. stipitis* integrated into the genome (H1506, Table 32). The multi-copy vector harboring the DOG1 encoding gene (B1020, see example 16) was transformed into the above mentioned strain, and the host strain H1104, resulting in the strains H1520 and H1514, respectively. In addition, the empty vector YEplac 195 was transformed into the strain resulting in the control strain H1524. B1020 was also transformed into H1741, the TKL1,2 deficient strain with the XDH encoding gene from *T. reesei* integrated into the genome, resulting in strain H2425.

The specificity of DOG1 towards xylulose-5-P, ribulose-5-P, ribose-5-P and 2-deoxyglucose-6-P was determined using 20 mM substrate concentrations. Yeast cell extracts were prepared as described in example 15, except that 50 mM imidazole-HCl, 10 mM $MgCl_2$ buffer, pH 6.0 was used. 10 µl of extract and 210 µl of substrate (20 mM) in the same buffer was incubated for 30 min, 30° C. The reaction was stopped with final 2% of TCA and the phosphate released was measured using ammonium molybdate (15 mM), zinc acetate (100 mM), pH 5.0 as the reagent. The formation of molybdenum blue was measured at 350 nm, and quantified by phosphate standards (Sanz, P. et al., *Yeast* 10:1195–1202 (1994); Bencini, D. A. et al., *Anal. Biochem.* 132:254–258 (1983)). The results are shown in Table 15.

TABLE 15

Specificity of the DOG1 in yeast cell extracts of the host strain harboring the DOG1 encoding gene on a multi-copy plasmid (H1514). Activities are shown as relative values of the activity towards 2-deoxyglucose-6-P as 100%.

| Sugar phosphate | Relative activity (20 mM)[1] | Activity reported in the literature[3] (40 mM) |
| --- | --- | --- |
| xylulose-5-P | 15 | n.d.[2] |
| ribulose-5-P | 6 | 7 |
| ribose-5-P | 52 | 42 |
| 2-deoxyglucose-6-P | 100 | 100 |

[1]The substrate concentration used in the assay
[2]Not determined
[3]Randez-Gil, F. et al., *Yeast* 11:1233–1240 (1995)

The pre-culture was grown in SCD medium lacking uracil for plasmid selection, cells were collected, washed once with water and suspended in the same growth medium to OD600 of approximately 0.2. The cells were incubated on a shaker at 250 rpm, 30° C. During the cultivation samples were collected at the indicated time points, the OD600 was determined, and the cells removed by centrifugation. The growth medium samples were analyzed for polyols and pentoses by HPLC. The HPLC analyses were carried out with Waters 510 HPLC pump, Waters 712 WISP and Water System Interfase Module liquid chromatography complex with refractive index detector (Waters 410 Differential refractometer). The Shodex-Pb column used (Shodex SP0810, Showa Denko K.K., Tokyo, Japan; 80° C., flow rate 0.6 ml/min, water as eluent) resulted in the coelution of ribose and xylitol, in addition ribitol was quantitated. Results are shown in Table 16.

TABLE 16

Production of polyols and pentoses (g/g cell dry weight) by the TKL1,2 deficient strain of *S. cerevisiae* harboring the XDH encoding gene of *P. stipitis* integrated and the DOG1 encoding gene on a multi-copy plasmid

| | 67 h[1] | | | 137 h | | |
| --- | --- | --- | --- | --- | --- | --- |
| Strain | Total[2] | ribitol[3] | ribose + xylitol[3] | Total | ribitol | ribose + xylitol |
| TKL1,2 deficient *P. stipitis* XDH YEplac195 H1524 | 0.546 | 0.412 | 0.134 | 0.715 | 0.544 | 0.171 |
| TKL1,2 deficient *P. stipitis* XDH DOG1 (B1020) H1520 | 0.830 | 0.608 | 0.222 | 1.063 | 0.772 | 0.291 |

[1]The time point in hours of the growth medium sample withdrawn
[2]Ribitol + ribose + xylitol g/g cell dry weight
[3]Ribitol or (ribose + xylitol) g/g cell dry weight The production of polyols and pentoses was related to glucose consumed during the cultivation. Results are shown in Table 17.

TABLE 17

Polyols and pentoses produced (ribitol, xylitol, ribose; g/l) per glucose consumed (g/l). Also, the glucose consumed per cell dry weight is shown.

| | 22 h[1] | | 67 h | |
| --- | --- | --- | --- | --- |
| Strain | polyols/[2] glu cons. in % | glu cons./[3] g c dw | polyols/ glu cons. in % | glu cons./ g c dw |
| TKL1,2 deficient *P. stipitis* XDH YEplac195 H1524 | 1.0 | 10.5 | 2.0 | 20.3 |
| TKL1,2 deficient *P. stipitis* XDH DOG1 (B1020) H1520 | 1.7 (70)[4] | 11.3 | 2.8 (40) | 19.8 |

[1]The time point in hours of the growth medium sample withdrawn
[2]Polyols and pentoses (ribitol, xylitol, ribose; g/l) produced per glucose (g/l) consumed in %.
[3]Glucose consumed (g/l) per cell dry weight (g/l)
[4]Increase in % as compared to the control strain H1524

The production of polyols and pentoses was also studied with the TKL1,2 deficient strain harboring the XDH encoding gene from *T. reesei* integrated into the genome and the multi-copy plasmid carrying the DOG1 encoding gene H2425 (for detailed description of the cultivation conditions and analytical methods; HPLC and enzymatic assays see the example in next paragraph with the LTP 1 encoding gene of *S. cerevisiae*) Results are shown in Table 18.

TABLE 18

Production of pentitols and pentoses by the TKL1,2 deficient strain harboring the XDH encoding gene from. *T. reesei* integrated and over-expressing the DOG1 encoding gene from a multi-copy plasmid

| Strain | Ribitol[1] | Xylulose[1] | Ribulose[1] | Total[1] | Ribitol + ribose + ribulose[2] |
|---|---|---|---|---|---|
| TKL1,2 deficient *T. reesei* XDH H1741 | 0.061 | 0.013 | 0.058 | 0.132 | 0.174 |
| TKL1,2 deficient *T. reesei* XDH B1181 H2421 | 0.085 | 0.013 | 0.047 | 0.145 | 0.170 |
| TKL1,2 deficient *T. reesei* XDH B1020 DOG1 H2425 | 0.199 | 0.032 | 0.090 | 0.321 | 0.643 |

[1]Ribitol, xylulose, ribulose or total of ribitol + xylulose + ribulose (g/g cell dry weight) determined by the enzymatic assays
[2]Total ribitol, ribose and ribulose (g/g cell dry weight) determined by HPLC This example discloses that the DOG1 phosphatase expressed from a multi-copy plasmid enhanced the polyol and pentose production 1.5–4 fold in the TKL1,2 deficient strain (see Table 16). Results in Table 18 disclose that also xylulose and ribulose production was increased 2–3 fold. The conversion of glucose into product was significantly enhanced (see Table 17), i.e. the yield of product from glucose was increased which demonstrates increased flux into PPP.

b) Increased Production of Polyols and Pentoses in the TKL1,2 Deficient Strain Over-expressing the LTP1 Gene Encoding a Phosphatase The TKL1,2 deficient strain harboring the XDH encoding gene from *T. reesei* integrated into the genome (H1741) was transformed with the multi-copy plasmid carrying the Low Molecular Weight Protein-Tyrosine Phosphatase (LTP1, see example 16), resulting in strain H2422, and with the control plasmid B1181 devoid of LTP1 encoding gene, resulting in strain H2421 (see example 16). The strains were cultured from a single colony in SCD medium lacking uracil. After cultivation of 42 hours in 30° C. the cells were removed by centrifugation and the culture medium supernatants were collected. Pentoses and pentitols were analyzed from the supernatant samples by HPLC (see below) or by enzymatic assays using COBAS Mira automated analyzer (Roche).

Ribitol and xylitol were measured as described in part "c" of Example 15. Ribulose was measured from the samples during 20 minutes incubation at 37° C. by analyzing the decrease of NADH with ribitol dehydrogenase (0.07 U/ml) in a reaction containing 100 mM $KH_2PO_4$, pH 7.0 and 0.2 mM NADH. Combined xylulose and ribulose amounts were measured like the ribulose amount, except sorbitol dehydrogenase (0.2 U/ml) was also used in the reaction. Xylulose amounts were obtained by subtracting the ribulose amounts from combined ribulose and xylulose amounts. Ribitol dehydrogenase used in the enzymatic assays was purified from *Klebsiella pneumoniae* (E-87293, VTT strain collection) according to the protocol described previously (Bergmeyer, 1974).

The HPLC analyses were carried out with Waters 510 HPLC pump, Waters 712 WISP and Water System Interface Module liquid chromatography complex with refractive index detector (Waters 410 Differential refractometer). The Aminex HPX-87H Ion Exclusion Column (300 mm×7.8 mm, Bio-Rad) used was equilibrated with 5 mM $H_2SO_4$ in water at 55° C. and samples were eluted with 5 mM $H_2SO_4$ in water at 0.3 ml/min flow. The standard solutions were prepared from dry crystalline sugars obtained from Sigma Chemical Company. Results are shown in Tables 19–21.

TABLE 19

Production of ribitol, xylitol, ribulose and xylulose (g/g cell dry weight) by the strain over-expressing the LTP1 encoding gene as measured with enzymatic assays.

| Strain | Ribitol | Xylitol | Xylulose | Ribulose | Total |
|---|---|---|---|---|---|
| TKL1,2 deficient *T. reesei* XDH (H1741) | 0.061 | n.d.[1] | 0.013 | 0.058 | 0.132 |
| TKL1,2 deficient *T. reesei* XDH B1181 (H2421) | 0.085 | n.d. | 0.013 | 0.047 | 0.145 |
| TKL1,2 deficient *T. reesei* XDH B1449 LTP1 (H2422) | 0.061 | 0.014 | 0.033 | 0.126 | 0.234 |

[1]n.d. - below reliable detection limit

TABLE 20

The ratios of different pentitols and pentoses (in %) by the strain that over-expresses the LTP1 encoding gene as measured with the enzymatic assays.

| Strain | Ribitol | Xylitol | Xylulose | Ribulose |
|---|---|---|---|---|
| TKL1,2 deficient *T. reesei* XDH (H1741) | 46 | n.d.[1] | 10 | 44 |
| TKL1,2 deficient *T. reesei* XDH B1181 (H2421) | 59 | n.d. | 9 | 32 |
| TKL1,2 deficient *T. reesei* XDH B1449 LTP1 (H2422) | 26 | 6 | 14 | 54 |

[1]n.d. - below reliable detection limit.

TABLE 21

Production of ribitol, ribulose, xylulose and ribose (g/g cell dry weight) by the strain that over-expresses the LTP1 encoding gene as measured with HPLC.

| Strains | Xylulose | Ribitol + ribose + ribulose |
|---|---|---|
| TKL1,2 deficient T. reesei XDH (H1741) | n.d.[1] | 0.174 |
| TKL1,2 deficient T. reesei XDH B1181 (H2421) | n.d.[1] | 0.170 |
| TKL1,2 deficient T. reesei XDH B1449 LTP1 (H2422) | 0.082 | 0.348 |

[1]n.d. - below reliable detection limit

The results in Tables 19–21 show that the strain that over-expressed the LTP1 encoding gene (H2422) produced more xylulose (2.5 fold and 2.5 fold, respectively) and ribulose (2.2 fold and 2.7 fold, respectively) than the strains without the LTP1 encoding gene over-expressed (H1741 and H2421). H2422 also produced xylitol (14 mg/g cell dry weight) unlike the strains H1741 and H2421 which in this particular experiment did not produce xylitol. The total amounts of pentoses and pentitols (ribitol, xylitol, xylulose and ribulose) in the strain H2422 showed an increase of 80–100% in production as compared to the H1741 and H2421 strains in this particular experiment.

Also the ratio of different pentoses and pentitols was changed in H2422-strain (Table 20): it produced more ribulose (54%) as compared to the H1741 (44%) and H2421 (32%) strains. The same is observed with "xylulose+xylitol": H2422 produced 20% "xylulose+xylitol" from the total amount of pentoses and pentitols, while H1741 and H2421 only produced 10% and 9% of the total amount of pentoses and pentitols, respectively. The ribitol amount as compared to other pentoses and pentitols is decreased (26%) in H2422 as compared to the H1741 (46%) and H2421 (59%) strains.

The glucose consumed during the cultivation period of 42 h was measured and demonstrated an increased flux of glucose into the PPP. The control strain H2421 converted 1.0% of the glucose consumed into pentitols and pentoses, but in the strain with the LTP1 encoding gene over-expressed (H2422) the conversion was 1.7% of the glucose consumed, demonstrating an increase of 70%.

This example discloses that over-expression of the LTP1 encoding gene in a TKL1,2 deficient strain of Saccharomyces cerevisiae harboring an integrated XDH encoding gene from T. reesei enhanced the production of pentitols and pentoses by a factor of 1.6–1.8. Moreover, the ratios of the pentitols and pentoses were altered to favor the production of xylulose, (xylitol) and ribulose. The glucose conversion into products was enhanced by 70% as a result of enhanced flux into the PPP.

Example 18

Strains and Strain Constructions of Saccharomyces Cerevisiae for Studies of Reduced Glycolytic Activity Two different strains of S. cerevisiae disrupted in phosphoglucoisomerase (PGI1) encoding gene were obtained from Dr. Eckard Boles (Düsseldorf, Germany) and renamed as H1053 [EBY22, Boles, E., et al., Eur. J. Biochem. 217: 469–477 (1993)] and H1054 [EBY44, Boles, E., et al., Mol Gen. Genet. 243: 363–368 (1994)].

For constructing strains of S. cerevisiae having lowered activity of phosphoglucose isomerase, plasmids for creating partial PGI1 promoter deletions were obtained from Dr. Eckard Boles [Rose, M., et al., Eur. J. Biochem. 199: 511–518 (1991)]. The PGI1 deficient strain H1054 was transformed with the partial promoter deletion plasmids pBR4 and pBR5 which were linearized with HpaI. Leucine prototrophs were selected. The resulting strains were named H1768 and H1770, respectively.

The strain deficient for genes coding for 6-phosphofructo-L-kinase (PFK26 and PFK27) was obtained from Dr. Susanne Müller (Darmstadt, Germany) and renamed as H1347. The strain was transformed with yeast multi-copy vector pAOS64 (see example 12) containing the XDH encoding gene from Pichia stipitis and the resulting strain was named as H1759.

The strains H1055 (TKL1,2 deficient strain) and H1053 (PGI1 deficient strain) were mixed as a batch on YPF plates for mating. The batch was checked for zygotes after two days. Single colony streaks were made from the batch on YPF and SCD-tyr-phe plates. Twenty-four large colonies from each type of plate were transferred as streaks on respective plates. All 48 colonies were verified to be diploids by the mating type test with control strains H5 and H6 (Appendix I, Table 32). Four colonies were further transferred as single colony streaks onto minimal medium plates [YNB (Yeast Nitrogen Base 6.7 g/l; Merck, Germany)+2% glucose]. A single colony from the four plates was streaked as a batch on presporulation plates (5% glucose) for two days. The batch was further transferred to sporulation plates (with reduced C- and N-sources) for starvation conditions to promote spore formation. After 9 days the plates were checked for tetrads. Two batches with 40–50% tetrads were chosen for random spore isolation. Snail enzyme gluculase was diluted 1 to 10 in water and yeast suspension from the sporulation plates amounting for half the size of a matchhead was mixed with 200 µl of the enzyme dilution. The mixture was incubated for 2 hours in a shaker. One ml of water was added and the mixture was vigorously vortexed. Dilutions −3, −4 and −5 were plated on YPF for three days. 440 colonies were picked to streak on SC+2% fructose+ 0.05% glucose plates for two days. The streaks were replicated on YPD (PGI1 deficient mutant does not grow) and SC+2% fructose+0.05% glucose-tyr-phe (TKL1,2 deficient mutant does not grow) plates. Four positive candidates (no growth on YPD and SC+2% fructose+0.1% glucose-tyr-phe) were obtained. The candidates were checked for retaining the PGI1 and TKL1,2 disruptions by Southern blotting. Chromosomal DNA was digested with BglII (TKL1), ClaI (TKL2) or BglI (PGI1), and the probes used were from the PGI1 gene (+100 to +1640 nucleotides), the TKL1 gene (+115 to +1060) and the TKL2 gene (+810 to +1870). All probes were made with PCR, labeled with digoxigenin-labeled dNTP mixture (Boehringer Mannheim, Germany) and purified with QIAquick columns. The blots showed unchanged patterns as compared with the parent strains. Of the four colonies, number I was selected for further experiments and named as H1451.

Figure 19:
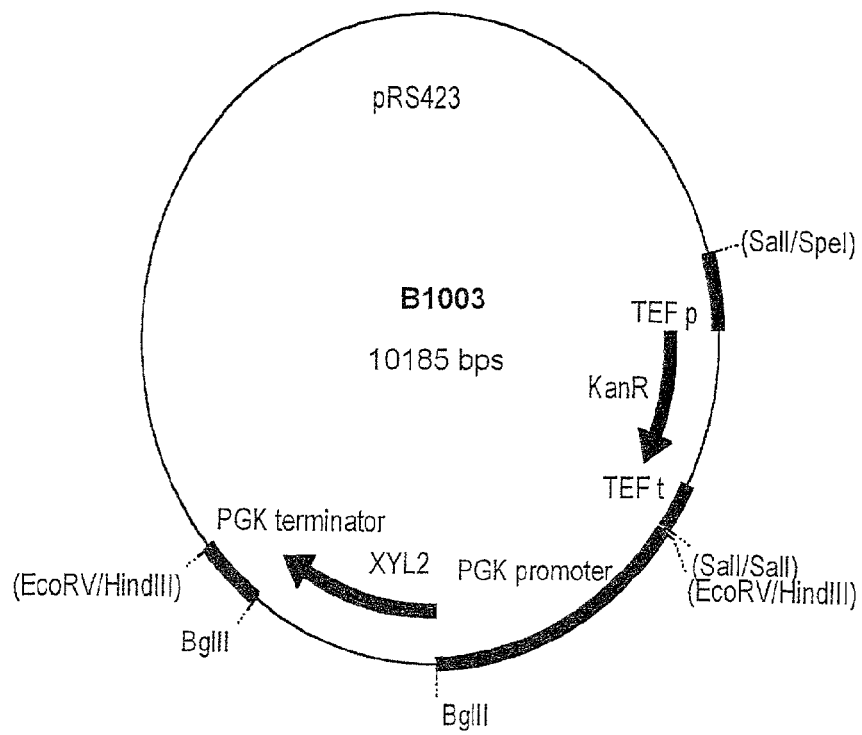
FIG. 19. The genetic map of B1003 with the relevant expression cassette and restriction sites indicated.

For introducing the XDH encoding gene from P. stipitis into the above mentioned strain H1451, the plasmid pAOS67 was digested with SalI enzyme, treated with Klenow enzyme and then with shrimp alkaline phosphatase. The kanMX2 fragment from the pFA6-kanMX2 plasmid [Wach, A., et al., Yeast 10: 1793–1808 (1994)] was released with SalI and SpeI, purified by gel electrophoresis and extracted from the gel by the phenol-liquid nitrogen method. The purified fragment was treated with Klenow enzyme for creating blunt ends. The kanMX2 fragment was cloned into the pAOS67 SalI site. The plasmid pAOS67 with genenticin resistance gene was named as B1003 (FIG. 19) and introduced into the TKL1,2; PGI1 deficient strain H1451 resulting in strain H1453.

Example 19

Enhanced Conversion of Glucose into Pentitols in the *Saccharomyces Cerevisiae* Strain Lacking PGI1 and/or TKL1,2 Activities Multi-copy plasmid B1003 containing the XDH encoding gene from *P. stipitis* and the kanamycin resistance marker gene (pAOS67 +kan$^r$, FIG. 19) was transformed into the TKL1,2;PGI1 deficient strain H1451 resulting in strain H1453 (Appendix I, Table 32). The resulting strain and various control strains were grown on synthetic complete medium containing 2% fructose and 0.15% glucose. Samples were withdrawn during the cultivation as indicated, OD600 measured to monitor the growth, cells were removed by centrifugation and the growth medium samples were assayed for polyols (xylitol and part of ribitol; see Example 14) by Boehringer Mannheim D-sorbitol/xylitol kit and for glucose by Boehringer Mannheim GOD-Perid kit. Results are shown in Table 22.

Example 20

Partial Block in Glycolysis Redirects Carbon (Glucose) Flow to the Pentose Phosphate Pathway in *Saccharomyces Cerevisiae* a) Reduced Activity of Phosphoglucoisomerase Leads to Increased Polyol Production A plasmid series containing the full length coding region of the phosphoglucoisomerase (PGI1) encoding gene and varying lengths of its promoter were obtained from Dr. Eckard Boles (Düisseldorf, Germany). Transformation of the PGI1 deficient yeast strain with these plasmids yields transformants with varying PGI1 activity [Rose, M., et al., *Eur. J Biochem.* 199:511–518 (1991)]. The PGI1-promoter deletions constructed by Rose et al. were used. Eight different plasmids with successive promoter deletions on a centromeric plasmid (pMR206 series) were digested with PstI and DraI. The fragments carrying the PGI1 gene with promoters of different size were subcloned into the integrating plasmid YIplac128 (Gietz and Sugino, *Gene* 74:527–534 (1988)). The resulting plasmids pRB1 to pRB8 were linearized with HpaI and transformed separately into the strain H1054 and the specific activity of phosphoglucose isomerase determined. (E. Boles, personal communication). With the postulation in mind that 10% of full PGI1 activity sustains growth on glucose, two plasmids giving a PGI1 activity of 8% (pRB4) and 5% (pRB5) were selected for the construction of yeast strains with reduced PGI1 activities. Plasmids pRB4 and pRB5 were introduced into the PGI1

TABLE 22

Polyol production by the TKL, PGI1 deficient strain harboring the XDH encoding gene from *P. stipitis* on a multi-copy plasmid.

| | Early growth phase (OD600~1.5) | | Late growth phase (OD600~4.0) | |
|---|---|---|---|---|
| Strain | polyols (mg/g dw)[1] | polyols (mg/g glucose)[2] | polyols (mg/g dw) | polyols (mg/g glucose) |
| PGI1 deficient H1054 | 0 | 0 | 33 | 26 (3) |
| TKL1,2 deficient H1055 | n.d.[3] | n.d. | 50 | 29 (3) |
| TKL1,2 deficient pAOS67 *P. stipitis* XDH H1057 | 32 | 15 (2)[4] | 110 | 72 (7) |
| TKL1,2 and PGI1 deficient H1451 | 86 | 56 (6) | 96 | 83 (8) |
| TKL1,2 and PGI1 deficient B1003 *P. stipitis* XDH H1453 | 203 | 128 (13) | 266 | 190 (19) |

[1]Polyols produced in mg/g cell dry weight
[2]Polyols produced in mg/g glucose consumed
[3]Not determined
[4]The fraction in % of glucose converted to polyols The above results show a yield of about 0.2 g of polyols per g of glucose with the TKL1,2; PGI1 deficient strain harboring the XDH encoding gene, which is about 3–6 times higher conversion of glucose to polyols as compared to the TKL1,2 deficient strain harboring the XDH encoding gene. This particular strain grows slowly and so its polyol production is also slow. This example discloses that block both in glycolysis (PGI1 deficient) and pentose phosphate pathway (TKL1,2 deficient) leads to enhanced conversion of glucose into polyols in *Saccharomyces cerevisiae*.

deficient strain H1054 resulting in strains H1768 and H1770, respectively (Appendix I, Table 32). The strains were transformed with the multi-copy plasmid pAOS67 (FIG. 12) harboring the XDH encoding gene from *P. stipitis* resulting in strains H1772 and H1774, respectively. These strains were grown on 2% fructose with 0.05% glucose, and for comparison a completely PGI1 deficient strain harboring the multi-copy plasmid pAOS67 was included in the cultivation (H1117). Samples were taken at the indicated time points and growth was monitored by measuring the OD 600. Cells were removed by centrifugation and the growth medium samples were analyzed for polyols (xylitol and part of ribitol; see Example 14) by the D-sorbitol/xylitol Boehringer Mannheim kit. Results are shown in Table 23.

TABLE 23

Production of polyols by S. cerevisiae strains with reduced PGI1 activity harboring the XDH encoding gene from P. stipitis on a multi-copy plasmid.

| Strain | Polyols[1] | | |
|---|---|---|---|
| | 47 h[2] | 72 h | 125 h |
| PGI1 reduced pAOS67 P. stipitis XDH H1772 | 16 | 15 | 18 |
| PGI1 reduced pAOS67 P. stipitis XDH H1772 | 15 | 17 | 25 |
| PGI1 reduced pAOS67 P. stipitis XDH H1774 | 17 | 17 | 21 |
| PGI1 reduced pAOS67 P. stipitis XDH H1774 | 18 | 21 | 21 |
| PGI1 deficient pAOS67 P. stipitis XDH H1117 | 8 | 9 | 10 |

[1]Xylitol + part of ribitol (mg/g cell dry weight) measured by the Boehringer Manneheim D-sorbitol/xylitol kit.
[2]The time point in hours when the growth medium sample was withdrawn This example discloses that yeast strains with reduced PGI1 activity enhance the polyol production about 2-fold as compared to the strain completely lacking the PGI1 activity.

b) Polyol Production in the S. cerevisiae Strain Lacking the 6-phosphofructo-2-kinase Activity Fructose-2,6-bisphosphate (F2,6P) has been shown to be a potent activator of 6-phosphofructo-1-kinase and a strong inhibitor of fructose-1,6-bisphosphate-1phosphohydrolase and thereby an important regulator of glycolysis. In S. cerevisiae F2,6P is synthesized by two 6-phosphofructo-2-kinase encoding genes PFK26 and PFK27. In particular, F2,6P is needed for the rapid consumption of sugars [Boles, E., et al., Mol. Microbiology 20:65–76 (1996)]. Our interest was to study if deletion of these two genes would increase polyol production as a consequence of reduction in glycolytic flux leading to increase of glucose directed to the PPP.

A PFK26, PFK27 deficient strain was transformed with a multi-copy vector harboring the XDH encoding gene from P. stipitis on a multi-copy vector (pAOS64). Cells were cultivated in synthetic complete medium with 20 g/l glucose and uracil was omitted for plasmid selection. Cell growth was monitored by measuring the OD600, and culture medium samples analyzed for polyols produced with the D-sorbitol/xylitol kit of Boehringer Mannheim. Results are shown in Table 24.

TABLE 24

Polyol (part of ribitol + xylitol) production (mg/g cell dry weight) by the PFK26,PFK27 deficient strain harboring the XDH encoding gene from P. stipitis on a multi-copy plasmid

| Strain | Polyols mg/g cell dry weight | | |
|---|---|---|---|
| | 23 h[1] | 32 h | 47 h |
| PFK26,27 deficient pAOS64 XDH H1759 | 4.90 | 4.89 | 6.71 |

TABLE 24-continued

Polyol (part of ribitol + xylitol) production (mg/g cell dry weight) by the PFK26,PFK27 deficient strain harboring the XDH encoding gene from P. stipitis on a multi-copy plasmid

| Strain | Polyols mg/g cell dry weight | | |
|---|---|---|---|
| | 23 h[1] | 32 h | 47 h |
| PFK26,27 deficient H1347 | 2.62 | 2.38 | 2.72 |

[1]The time point in hours of the growth medium sample withdrawn.

This example discloses that polyols can be produced in the PFK26,27 deficient strain and that over-expression of the XDH encoding gene from P. stipitis enhances the polyol production 2-3 fold.

c) Reduced Activity of Glyceraldehyde-3-phosphate Dehydrogenase Leads to Increased Polyol Production and Flux to Pentose Phosphate Pathway Increasing amounts of iodoacetate (IA) are known to gradually inhibit glyceraldehyde-3-phosphate dehydrogenase thus leading to decreased flux of glucose into the lower part of glycolysis. TKL1,2 deficient strain H1055 carrying the pAOS67 multi-copy plasmid harboring the XDH encoding gene from P. stipitis (H1057) was cultivated in the presence of 25 µM IA (Fluka Chemie AG, Switzerland). The growth medium was SCD lacking histidine for plasmid selection and 7.65 g/l KNO3. Samples were withdrawn at the indicated time points, the OD600 measured, cells removed by centrifugation, and the growth medium samples were assayed for polyols by the Boehringer Mannheim D-sorbitol/xylitol kit and for glucose by the Boehringer Mannheim GOD-Perid kit. Results are shown in Table 25.

TABLE 25

Production of polyols by the TKL1,2 deficient strain harboring the XDH encoding gene from P. stipitis on a multi-copy plasmid in the presence of iodoacetate

| | Polyols from glucose consumed in % | | | | | | |
|---|---|---|---|---|---|---|---|
| | 28 h | 45 h | 52 h | 69 h | 77 h | 93 h | 100 h |
| TKL1,2 deficient pAOS67 P. stipitis XDH H1057 with iodacetate | 0.45 | 0.74 | 0.57 | 0.72 | 0.87 | 0.93 | 1.13 |
| TKL1,2 deficient pAOS67 P. stipitis XDH H1057 without iodacetate | 0.30 | 0.48 | 0.45 | 0.53 | 0.65 | 0.66 | 0.87 |

An increase of about 30% in polyol production was observed in the presence of iodoacetate resulting in 1.2% of the glucose consumed metabolised to polyols (xylitol+part of ribitol). This example discloses that reduction of the activity of glyceraldehyde-3-phosphate dehydrogenase by iodoacetate leads to enhanced production of pentitols and glucose flux into pentose phosphate pathway.

Example 21

Construction of S. cerevisiae Strains with Altered Redox Balance

The gene encoding the NAD-dependent glutamate dehydrogenase (GDH2) was cloned from the plasmid YEpMSP3-T [Boles, E., et al., *Eur. J. Biochem.* 217:469–477 (1993)] to the YEplac195 multi-copy plasmid [Gietz, R. D. and Sugino, A., *Gene* 74:527–534 (1988)] as a SstI—XbaI fragment, resulting in plasmid B1007. The B1007 plasmid was transformed into the TKL1,2 deficient strains harboring the XDH encoding gene from *P. stipitis* and *T. reesei* (H1506 and H1741, respectively), resulting in strains H1499 and H1743, respectively.

Figure 20:
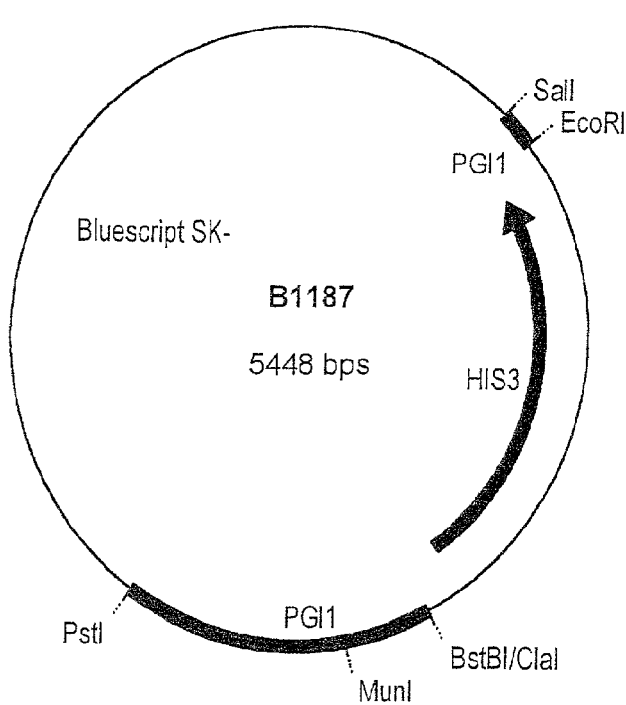
FIG. 20. The genetic map of B1187 with the relevant expression cassette and restriction sites indicated.

Another approach was taken (see example 18) to construct a PGI1; TKL1,2 deficient strain harboring the XDH encoding gene from *T. reesei* integrated into the genome in order to obtain usable selection markers for expression of additional genes on plasmids. The PGI1 encoding gene was disrupted by integrating the HIS3 gene of *S. cerevisiae* into the gene. The PGI1 gene was amplified by PCR with an oligonucleotide pair oPGI11 (SEQ ID NO: 32) and oPGI12 (SEQ ID NO: 33) and cloned into SalI—PstI sites of Bluescript SK (−) vector, resulting in plasmid B1186. The HIS3 gene was cloned from the vector pRS423 as a DrdI fragment into the EcoRV site of Bluescript SK (−), resulting in plasmid B1185. The PGI1 containing vector B1186 was digested with EcoRI and BstBI and the 700 bp fragment thus removed of the PGI1 open reading frame was replaced with the HIS3 gene as EcoRI-ClaI fragment from the HIS3-Bluescript SK (−) vector B1185, resulting in plasmid B1187 (FIG. 20). The PGI1-HIS3-PGI1 fragment was released from B1187 with SalI-MunI digestion, purified from an agarose gel and transformed into the TKL1,2 deficient strain harboring the XDH encoding gene from *T. reesei* integrated into the genome (H1741). The correct integration in the transformants was verified by PCR, Southern blots, ability to grow without histidine and inability to grow on glucose. The strain obtained was named as H1857. The above mentioned plasmid containing the GDH2 encoding gene (B1007) was transformed into the H1857 strain, resulting in strain H1915. To obtain a control strain the vector YEplac195 was transformed into the strain H1857, resulting in strain H1916.

The yeast expression vector pAOS66 (FIG. 14) containing the XR encoding gene from *P. stipitis* under the PGK1 promoter and the XDH encoding gene from *P. stipitis* under the modified ADH1 promoter was transformed into the PGI1 deficient strain H1053 resulting in strain H1115.

Figure 21:
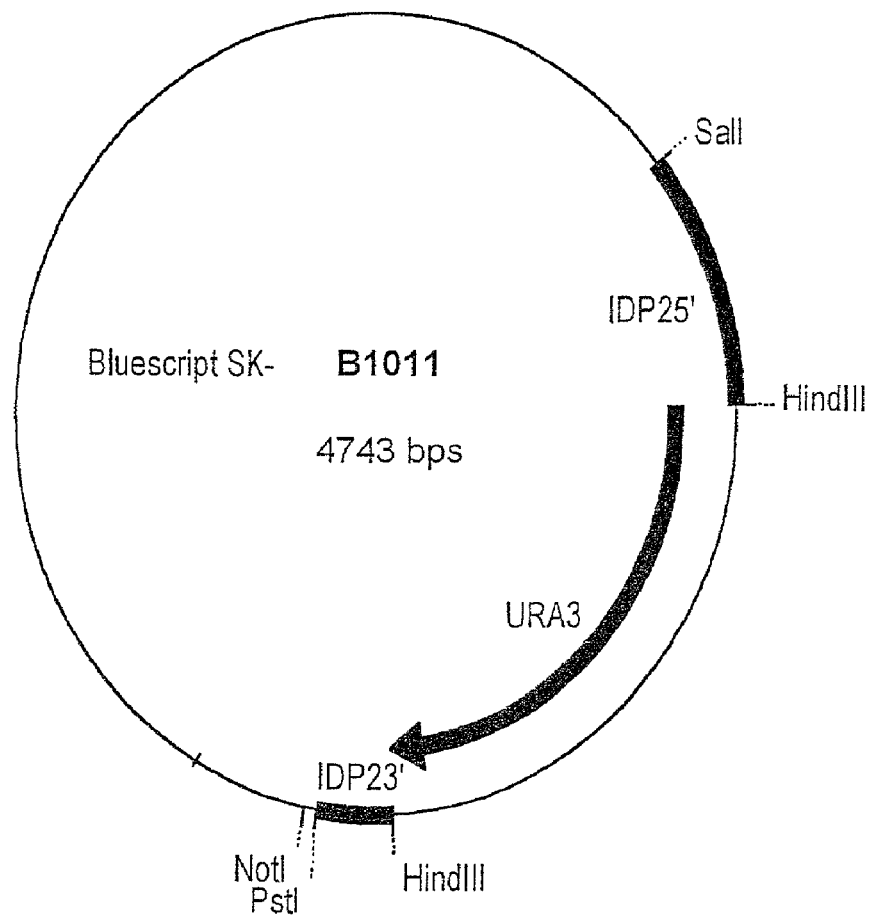
FIG. 21. The genetic map of B1011 with the relevant expression cassette and restriction sites indicated.

For disruption of the cytosolic NADP-dependent isocitrate dehydrogenase encoding gene (IDP2) [Loftus, T. M., et al., *Biochemistry* 33:9661–9667 (1994); Sazanov, L. A. and Jackson, J. B., *FEBS Letters* 344:109–116 (1994)] a disruption cassette was constructed by PCR; genomic DNA of strain H1346 was used as template DNA. For the 5' end an oligonucleotide pair oIDP21 (SEQ ID NO: 34) and oIDP22 (SEQ ID NO: 35) and for the 3' end an oligonucleotide pair oIDP23 (SEQ ID NO: 36) and oIDP24 (SEQ ID NO: 37) were used. The length of the amplified 5' end was 415 bp. The 5' end fragment was digested with SalI and HindIII, the 3' end fragment with HindIII and PstI (note, the 3' end fragment contained an unspecific HindIII star activity-site, resulting in a 3' fragment of only 158 bp) and the pBluescript SK (−) vector with SalI and PstI. These three components were ligated together in one step, resulting in a plasmid about 3.8 kbp in size (B1009). A URA3 gene as a 1170 bp fragment was released from the plasmid B713 [Toikkanen, J., et al., *Yeast* 12:425–438 (1996)] by HindIII digestion, purified from an agarose gel and ligated into the plasmid B1009 at the HindIII site, resulting in plasmid B1011 (FIG. 21). The fragment for IDP2 disruption was released from plasmid B1011 by SalI and NotI digestion. The fragment was transformed into the PGI1 deficient strain H1053 resulting in the strain H1576.

Example 22

Enhanced Production of Pentitols and Pentoses from Glucose in *Saccharomyces Cerevisiae* Strains with Altered Cellular Redox Balance a) Increased Polyol Production in the TKL1,2 Deficient Strain of *S. cerevisiae* that Over-expresses the NAD-dependent Glutamate Dehydrogenase Encoding Gene The NAD-dependent glutamate dehydrogenase encoding gene was over-expressed in the TKL1,2 deficient strain harboring the XDH encoding gene from *P. stipitis* or *T. reesei* integrated into the genome. The plasmid B1007 harboring the GDH2 encoding gene (see example 21) was transformed into the yeast strains H1506 and H1741, resulting in strains H1499 and H1743, respectively (Appendix I, Table 32). The strains were cultivated on synthetic complete medium (lacking uracil when appropriate for plasmid selection) containing 20 g/l glucose. Samples were taken at the indicated time points, the OD600 was measured, and cells were removed by centrifugation and polyols measured from the growth medium samples with the D-sorbitol/xylitol kit of Bochringer Mannheim with ribitol dehydrogenase added to the assay. Results are shown in Table 26.

TABLE 26

Polyol (ribitol + xylitol) production (g/g dry weight) by the TKL1,2 deficient strain with the XDH encoding gene from *P. stipitis* (P.s) or *T. reesei* (T.r) integrated and GDH2 encoding gene on a multi-copy plasmid.

| | Ribitol + Xylitol produced (g/g cell dry weight) | | | | |
| --- | --- | --- | --- | --- | --- |
| Strain | 24 h[1] | 44 h | 68 h | 81 h | 106 h |
| TKL1,2 deficient H1055 | 0.093 | 0.101 | 0.146 | n.d.[2] | 0.204 |
| TKL1,2 deficient *P. stipitis* XDH H1506 | 0.190 | 0.335 | 0.496 | 0.504 | 0.451 |
| TKL1,2 deficient *P. stipitis* XDH B1007 GDH2 H1499 | 0.316 | 0.396 | 0.612 | 0.633 | 0.830 |
| TKL1,2 deficient *T. reesei* XDH H1741 | 0.156 | 0.246 | 0.291 | 0.317 | 0.345 |
| TKL1,2 deficient *T. reesei* XDH B1007 GDH2 H743 | n.d. | 0.207 | 0.287 | 0.371 | 0.532 |

[1] The time point in hours of the growth medium sample withdrawn
[2] Not determined This example discloses that over-expression of the GDH2 encoding gene enhanced polyol (ribitol+xylitol) production by 50–80% in a TKL1,2 deficient strain of *S. cerevisiae* harboring an XDH encoding gene.

b) Increased Polyol Production in the PGI1;TKL1,2 Deficient Strain of *S. cerevisiae* that Over-expresses the NAD-dependent Glutamate Dehydrogenase Encoding Gene The NAD-dependent glutamate dehydrogenase (GDH2) encoding gene was over-expressed in H1857—the phosphoglucose isomerase (PGI1) and transketolase (TKL1,2) deficient strain that also harbors the XDH encoding gene from *T. reesei* integrated into the genome. H1857 was transformed with plasmid B1007 carrying the GDH2 encoding gene (see example 21) and with the empty plasmid YEplac195, resulting in strains H1915 and H1916, respectively.

Strains H1915 and H1916 were cultivated to logarithmic growth phase. The cells were collected and suspended into synthetic complete medium lacking histidine and uracil to an average density of OD600 20. Glucose was added to a final concentration of 20 g/l and a sample was taken immediately. The cells were incubated in a 30° C. shaker (250 rpm) for 2.5 h and the first sample was taken. Then $H_2O_2$ was added to a concentration of approximately 0.5 mM and incubation continued for an additional 1.5 h, when the second sample was taken. The OD600 was measured, cells were removed by centrifugation, and the growth medium samples were analyzed by HPLC (Waters device, Aminex HPX-87H Ion Exclusion Column, see example 17). Results are shown in Table 27.

TABLE 27

Production of polyols and pentoses in the PGI1;TKL1,2 deficient strain harboring the XDH encoding gene from *T. reesei* integrated, and the GDH2 encoding gene on a multi-copy plasmid

| | Glucose 2.5 h | Glucose + $H_2O_2$ 1.5 h | |
|---|---|---|---|
| Strain | (Xylulose, Ribulose, Ribose Ribitol) mg/g cell dw[1] | (Xylulose, Ribulose, Ribose Ribitol) mg/g cell dw | Xylulose mg/g cell dw |
| TKL1,2, PGI1 deficient *T. reesei* XDH YEplac195 H1916 | 8.5 | 21 | 0 |
| TKL1,2, PGI1 deficient *T. reesei* XDH B1007 GDH2 H1915 | 15 | 46 | 11 |

[1]Polyols + pentoses mg/g cell dry weight

A 2-fold increase in production of PPP derived compounds (xylulose/ribulose/ribose/ribitol) was seen with the strain H1915 that over-expresses the GDH2 encoding gene. Addition of hydrogen peroxide had a positive effect on total polyol and pentose production in both strains; an increase of 2-fold was seen both with and without the GDH2 encoding gene over-expressed in the TKL1,2;PGI1 deficient strain. Interestingly, $H_2O_2$ specifically resulted in the production of xylulose only in the strain that over-expressed the GDH2 encoding gene.

The glucose consumption by the strains during the experiment was measured and the ratios of polyols and pentoses produced from glucose consumed are shown in Table 28.

TABLE 28

Polyols and pentoses (ribitol, ribulose, xylulose; g/l) produced per glucose (g/l) consumed

| Strain | Glucose 2.5 h | Glucose + $H_2O_2$ 1.5 h |
|---|---|---|
| TKL1,2, PGI1 deficient *T. reesei* XDH YEplac195 H1916 | 0.11 | 0.24 |
| TKL1,2, PGI1 deficient *T. reesei* XDH B1007 GDH2 H1915 | 0.15 (36)[1] | 0.29 (21) |

[1]Increase in % of production as compared to the control strain H1916.

This example discloses that over-expression of a redox enzyme or alteration of the redox balance in *S. cerevisiae* leads to enhanced flux into the pentose phosphate pathway resulting in further increase in the production of pentitols and pentoses by the PGI1;TKL1,2 deficient strain. It further discloses that the yield of product from glucose is increased which demonstrates increased flux of glucose into PPP.

c) Increased Flux of Glucose into the Pentose Phosphate Pathway in the *S. cerevisiae* Strain Lacking the NADP-dependent Isocitrate Dehydrogenase Activity The cytosolic NADP-dependent isocitrate dehydrogenase (IDP2) catalyses the oxidative decarboxylation of isocitrate to α-ketoglutarate by the concomitant reduction of NADP. It thus competes for the same cofactor, NADP, that is utilized by the enzymes of the oxidative branch of pentose phosphate pathway, (which is also localized in the cytoplasm of the cells). Accordingly, disruption of the gene encoding IDP2 may increase the flux of glucose into PPP, as the demand for generation of NADPH in the cytosol can solely be fulfilled by the enzymes of this pathway in such a disruptant strain.

Figure 22:
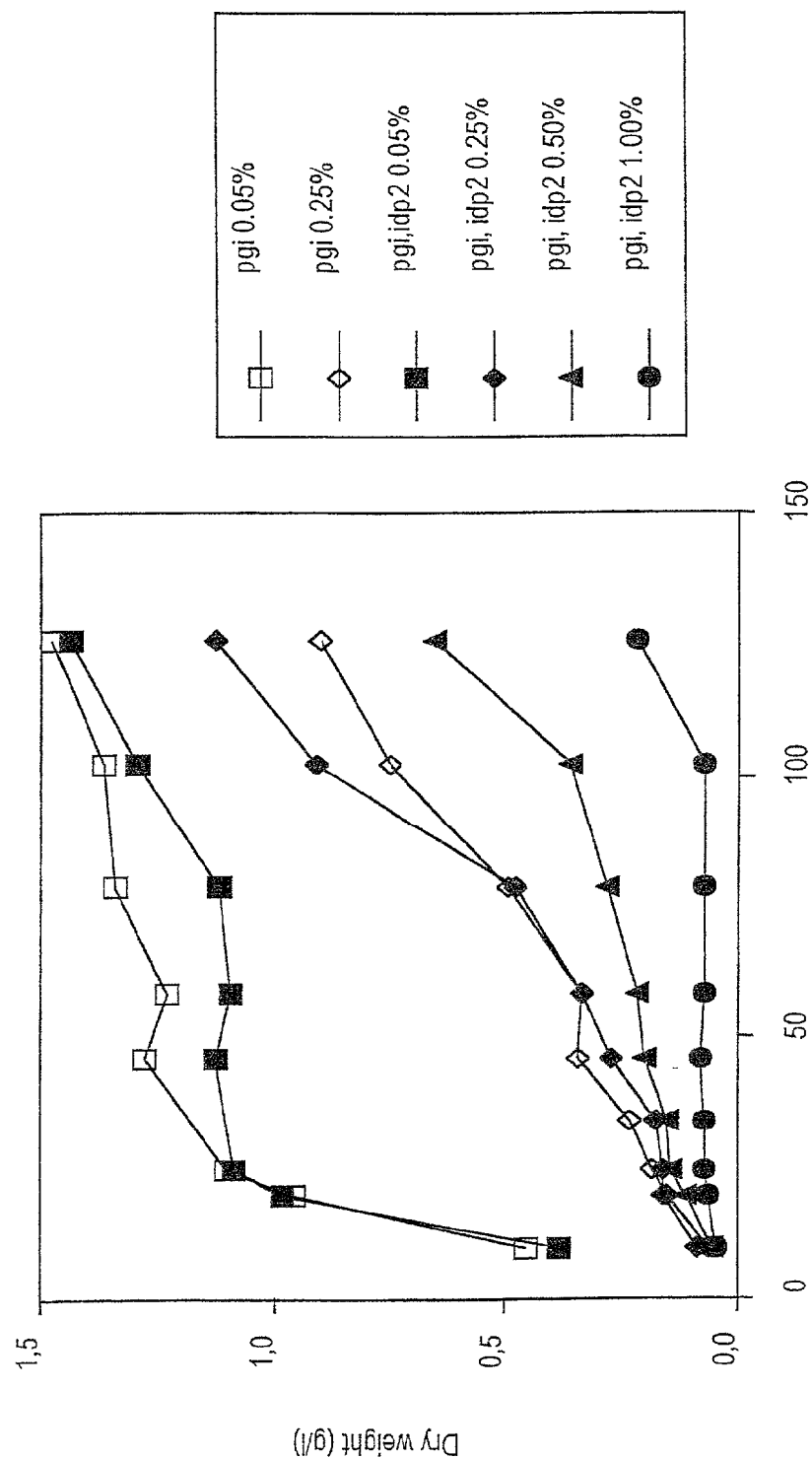
FIG. 22. Growth on different concentrations of glucose of PGI1 and PGI1, IDP2 deficient strains.

The growth of the PGI1 deficient strain is inhibited upon growth in higher than 0.2% glucose. Over-expression of the GDH2 encoding gene in the mutant restores its ability to grow in the presence of nearly as high levels of glucose as the host strain. To test our hypothesis, we disrupted the IDP2 encoding gene from the PGI1 deficient strain H1053 (see example 21 and Table 32) and studied its growth on different concentrations of glucose in the presence of 2% fructose. Results are shown in FIG. 22.

The PGI1, IDP2 deficient strain allows growth to higher cell densities in 0.25% glucose as compared to the PGI1 deficient strain. In addition, after-prolonged cultivation times, growth of the PGI 1, IDP2 deficient strain is observed at glucose concentrations of 0.5% and 1.0%, concentrations that are toxic to the PGI1 deficient strain. These results support the hypothesis that an increased flux of glucose into the PPP occurs, once the IDP2 encoding gene is deleted.

d) Increased Flux of Glucose into the Pentose Phosphate Pathway in the *S. cerevisiae* Strain Over-expressing a NAD (P)H-dependent Xylose Reductase The PGI1 deficient strain H1053 (see Appendix 1, Table 32) was transformed with a multi-copy plasmid pAOS66 (FIG. 14) containing the xylose reductase (XR) and XDH encoding genes from *Pichia stipitis*, resulting in the strain H1115.

Cells were cultivated in synthetic complete medium lacking leucine, supplemented with 20 g/l fructose and 0.5 g/l glucose. Cells were washed and resuspended in 100 mM phosphate buffer pH 5.0 to an OD600 of 130. D-glucose/ D-xylose mixtures with a total sugar concentration of 20 g/l were added and the ethanol production measured using a commercial enzymatic kit (Boehringer Mannheim). The results are shown in Tables 29–30.

TABLE 29

Ethanol concentration (mM) versus time after the sugar addition with two percent sugar comprising of D-xylose and D-glucose at various ratios. The glucose amount is given at the top of the columns.

| Time (min) | 0% glucose | 0.05% glucose | 0.10% glucose | 0.20% glucose | 2% glucose |
|---|---|---|---|---|---|
| 80 | 0.43 | 2.35 | 3.41 | 3.47 | 0.80 |
| 140 | 1.03 | 3.79 | 5.82 | 6.59 | 0.87 |
| 185 | 1.42 | 4.73 | 5.95 | 8.10 | 1.25 |
| 245 | 1.85 | 6.46 | 7.55 | 8.58 | 1.06 |
| 315 | 2.17 | 7.01 | 8.62 | 10.6 | 1.22 |
| 390 | 2.94 | 9.80 | 10.3 | 13.9 | 0.48 |

TABLE 30

Rate of ethanol production normalized to the maximal rate at a D-glucose D-xylose ratio of 0.2.

| D-glucose/D-xylose (g/g) | Normalized rate of ethanol production |
|---|---|
| 0 | 0.04 |
| 0.025 | 0.037 |
| 0.05 | 0.44 |
| 0.1 | 0.66 |
| 0.2 | 1 |
| 0.4 | 0.38 |
| 0.6 | 0.11 |
| 0.8 | 0 |
| 1 | 0 |

The rate of ethanol production was higher when a mixture of the two sugars was used as compared to using the pure sugars alone. When only glucose or only xylose was present ethanol production was low. This may be due to a depletion of cofactors. When D-glucose is metabolised through the pentose phosphate pathway, NADP is utilized; when D-xylose is converted to xylitol, NADPH is utilized. Depletion of either NADP or NADPH limits flux through the pentose phosphate pathway, i.e. limiting the ethanol production rate. Only when both sugars are metabolised simultaneously are the cofactors efficiently regenerated; each glucose converts two NADP to two NADPH that are then used for the formation of xylitol from D-xylose. The rate of ethanol production reflects the flux through the pentose phosphate pathway since this is the only possible route. The highest rate of ethanol production is observed when a mixture of glucose and xylose is fermented simultaneously, enabling an efficient regeneration of the cofactors. The rate of ethanol production is the highest when the glucose fraction is ⅓, i.e. when the xylose to glucose ratio is 2. This reflects the stoichiometry of the cofactor regeneration, i.e. 2 xylose-equivalents are needed to regenerate the cofactors for 1 glucose equivalent.

This example demonstrates that glucose fermentation through the pentose phosphate pathway is stimulated by the presence of a NADP regenerating system such as the NADPH requiring xylose reductase reaction.

According to the cofactor demand, a strain that overexpresses the XR encoding gene alone will result in a similar effect of enhanced glucose conversion into PPP derived products.

Similarly, an enhancement of glucose conversion into polyols and pentoses will occur in the TKL1,2 deficient or even in a non-deficient strain. The TKL1,2 deficient strain harboring the heterologous XR and XDH encoding genes as described above for the PGI1 deficient strain still cannot use xylose as a carbon source as xylulose-5-phosphate is not converted further in the pathway. In the host strain, xylose is reduced to xylitol by xylose reductase which at the same time oxidizes NAD(P)H. Xylitol is further oxidized to xylulose and xylulose phosphorylated to xylulose-5P, a pentose phosphate pathway intermediate. However, conversion of xylitol to xylulose is thermodynamically unfavorable and normally xylitol accumulates in xylose cultivations. The expression of the XR encoding gene leads to increased demand for NADPH, which is mainly produced in the pentose phosphate pathway. Our hypothesis is that as the strain is TKL1,2 deficient the only outlet for the carbon is as ketose or polyol; this leads to an increase of polyol and pentose production in the TKL1,2 deficient strain that overexpresses the XR encoding gene.

The examples described above will additionally result in xylitol production from both xylose and glucose simultaneously.

Example 23

Selecting *Saccharomyces Cerevisiae* Mutants that Produce Increased Amounts of Polyols and Pentoses The TKL1,2 deficient strains H1055 and H1741, the latter harboring the XDH encoding gene from *T. reesei* integrated into the genome (Appendix I, Table 32) were grown overnight on YPD medium (1% yeast extract, 2% peptone, 2% glucose). The cells were harvested (centrifugation 3000 rpm, 5 min) and suspended to 0.1 M sodium phosphate buffer (pH 7.0) in density of $2 \times 10^8$ cells/ml. The total amount of cells mutagenized was $4.7 \times 10^9$ in 20 ml. 500 µl of the cells were withdrawn for the control. 600 µl of the mutagen (ethylmethanesulfonite (EMS), Sigma) was added to the cell suspension. No mutagen was added for the control cells. The cells were incubated at 30° C. with agitation (250 rpm) for 60 min. The cells were then harvested and washed once with 20 ml of water and twice with 5% sodium thiosulphate (20 ml each) and resuspended in 1 ml of water. The mutagenized cells were plated on plates containing 2% galactose, 0.1% xylulose, 0.6% xylose, yeast extract and peptone (9 plates for each of the strains). Dilutions ($10^{-2}$, $10^{-3}$, $10^{-4}$, $10^{-5}$, $10^{-6}$, $10^{-7}$ and $10^{-8}$) of the control and the mutagenized cells were plated on YPD plates for the viability test. The viability after mutagenesis was about 60%. After 6 days incubation 20 and 13 colonies of strains H1055 and H1741, respectively grew on the plates. After 8 additional days of incubation, an additional 40 and 21 colonies, respectively, grew on the plates. The colonies were cultivated in 3 ml of SCD medium in test tubes at 30° C. and 250 rpm for 4 days. The OD600 of the cultivations was measured, cells were removed by configuration and the culture supernatants were analyzed by HPLC (HPX-87H column, Bio Rad, analysis conditions: 55° C., flow rate 0.3 ml/min, eluent 5 mM $H_2SO_4$) for the production of pentitols and pentoses. The results are shown in Table 31.

TABLE 31

Polyol and pentose production (g/g cell dry weight) of the strains H1055 and H1741 and the xylulose resistant mutants.

| Strain | Ribulose, ribitol, ribose (g/g dw) | Xylulose (g/g dw) | Total (g/g dw)[1] | Ribulose, ribitol, ribose (increase %)[2] | Total (increase %)[3] |
|---|---|---|---|---|---|
| H1055 | 0.66 | | 0.66 | | |
| 3 | 0.80 | 0.12 | 0.93 | 22 | 40 |
| 8 | 0.37 | 0.59 | 0.96 | −43 | 46 |
| 9 | 0.38 | 0.54 | 0.92 | −42 | 39 |

TABLE 31-continued

Polyol and pentose production (g/g cell dry weight) of the strains H1055 and H1741 and the xylulose resistant mutants.

| Strain | Ribulose, ribitol, ribose (g/g dw) | Xylulose (g/g dw) | Total (g/g dw)[1] | Ribulose, ribitol, ribose (increase %)[2] | Total (increase %)[3] |
|---|---|---|---|---|---|
| 11 | 0.50 | 0.50 | 0.99 | −25 | 50 |
| 15 | 0.90 | 0.11 | 1.01 | 37 | 53 |
| 58 | 0.45 | 0.52 | 0.98 | −31 | 48 |
| 61 | 0.84 | 0.13 | 0.97 | 28 | 47 |
| 62 | 0.83 | 0.13 | 0.96 | 26 | 45 |
| 63 | 0.78 | 0.30 | 1.09 | 19 | 64 |
| 72 | 0.82 | 0.16 | 0.99 | 25 | 49 |
| 73 | 1.10 | 0.27 | 1.37 | 66 | 107 |
| 74 | 1.04 | 0.20 | 1.24 | 57 | 87 |
| H1741 | 0.50 | 0.00 | 0.50 | | |
| 24 | 0.75 | 0.08 | 0.83 | −12 | 65 |
| 87 | 0.56 | 0.14 | 0.71 | −67 | 41 |

[1]Total; ribulose, ribitol, ribose and xylulose g/g cell dry weight.
[2]Increase in % of ribulose, ribitol, ribose production as compared to the parental strains H1055 and H1741.
[3]Increase in % of ribulose, ribitol, ribose and xylulose production as compared to the parental strains H1055 and H1741.

Some of the mutants obtained clearly produced more pentitols or pentose sugars. No detectable amounts of xylulose were produced by the parental strains in this particular experiment but several mutants produced xylulose in addition to increased amounts of ribulose, ribose or ribitol. In some mutants the ratio was shifted from ribulose, ribose and ribitol to xylulose. This example discloses the potential of classical mutagenesis in obtaining *S. cerevisiae* strains with increased production of pentitols and pentoses from glucose.

Example 24

Production of Xylitol or Ribitol by Recombinant Microbial Strains Expressing Xylitol-phosphate Dehydrogenase or Ribitol Phosphate Dehydrogenase Xylitol 5-phosphate dehydrogenase and ribitol-phosphate dehydrogenase have been purified from *Lactobacillus casei* (Hausman, S. Z. and London, J., *J. Bacteriol.* 169: 1651–1655 (1987)). It is known that similar enzymes are also present in some other bacteria, such as *Streptococcus avium* (London, J., *FEMS Microbiol. Reviews* 87:103–112 (1990)). The genes coding for such enzymes can be isolated by the methods known in the art. When such genes are expressed in a host of the invention that accumulates xylulose 5-phosphate and/or ribulose 5-phosphate (such as *B. subtilis* strain GX7 or *S. cerevisiae* H1055), the corresponding pentitol 5-phosphate is produced within such cell. Accumulating xylitol 5-phosphate or ribitol 5-phosphate is eventually dephosphorylated (for example, with xylitol-5-phosphatase) and excreted from the cell. A fast equilibrium between xylulose 5-phosphate and ribulose 5-phosphate is relatively easily achieved by over-expression of ribulose 5-phosphate epimerase. The equilibrium in the reaction catalyzed by pentitol 5-phosphate dehydrogenases depends on the redox potential (NADH/NAD$^+$ ratio) in the host cell. Under suitable conditions (high NADH/NAD$^+$ ratio), that are known to exist, for example, in yeast cells, the equilibrium is shifted very strongly in favor of pentitol phosphate. Thus, better overall control of the metabolic flux is possible, meaning that one product (xylitol or ribitol) is ultimately produced with a minimal formation of byproducts.

Example 25

Cloning of the Xylitol-phosphate Dehydrogenase (XPDH) Gene from *Lactobacillus rhamnosus*

XPDH was purified from *L. rhamnosus* ATCC 15820 essentially by the method of Hausman and London (*J. Bacteriol.* 169(4):1651–1655 (1987)).

The homogeneous protein was subjected to N-terminal sequencing yielding the following sequence: MKASMLEDLNKFSVKEIDIPSPKKD [SEQ ID NO:42]. Several peptides were also isolated from the tryptic digest of the XPDH and sequenced. The following sequences were identified: EWTNSIQLVR [SEQ ID NO:43], FGGFEQYVSVPAR [SEQ ID NO:44], GLDEGCTHVINSAK [SEQ ID NO:45].

Based on the partial amino acid sequences of the XPDH several degenerate oligonucleotides were synthesized and tested in PCR using the chromosomal DNA of *L. rhamnosus* as the template. The largest PCR product (with an apparent size of about 850 bp) was obtained using a combination of two primers: oLRXPD 53 (ATGAARGCITCIATGTTIGARGATTT [SEQ ID NO:46], sense primer) and oLRXPD 31(GCRTTIACIAR-YTGIATIGARTTNGTCCAYTC [SEQ ID NO:47,anti-sense primer). This PCR product was radioactively labeled with $^{32}$P and used as a probe to screen a *L. rhamnosus* chromosomal DNA library.

The library was constructed using a λ-phage-based vector (ZAP Express™, Stratagene). More specifically, a pre-digested (BamHI/CIAP-treated) ZAP Express™ vector kit was used to clone an approximately 2–5 kb DNA fragment fraction from a Sau3A partial digest of *L. rhamnosus* chromosomal DNA. The library size was more than 10$^5$ primary recombinants. Library construction, storage and screening were done according to the recommendations of the manufacturer (except that the library was stored frozen at −70° C. in the presence of 20% glycerol).

Several plaques strongly hybridizing to the PCR product described above were isolated, purified and converted to the phagemid form using the methods provided by Stratagene. The location of the coding region of XPDH gene within the isolated phagemids was determined using PCR with phagemid clones as templates, oLRXPD 53 (annealing at the 5' end of the coding region) as the sense primer and one of the two universal primers annealing in the vector part of the phagemid. One clone (pBK-CMV(LRXPD)-21) that contained the full coding sequence of XPDH gene (assuming that his enzyme belongs to the medium-chain dehydrogenase family and has a polypeptide chain of about 350 amino acid residues) was selected on the basis of these experiments. This clone was submitted to restriction mapping. A KpnI site was identified that is located about 200 bp downstream of the estimated XPDH coding region. Based on this information a smaller-size derivative of the plasmid pBK-CMV(LRXPD)-21 still containing the full-length XPDH gene was constructed. pBH-CMV(LRXPD)-21 was subjected to KpnI hydrolysis generating two DNA fragments (approximately 6 and 0.9 kb), the larger fragment was purified by agarose gel electrophoresis and ligated on itself. The resulting plasmid was named pBK(LRXPD) and subjected to DNA sequencing.

The sequence of the DNA insert in the plasmid pBK (LRXPD (SEQ ID NO:48) contains an open reading frame of 349 codons, beginning with the less usual start codon TTG. The deduced N-terminal amino acid sequence matched exactly the experimentally determined N-terminal amino acid sequence of XPDH. The deduced primary sequence of XPDH from *L. rhamnosus* (SEQ ID NO:49) is homologous to the sequences of a number of medium-chain dehydrogenases. Particularly high homology is observed with the sequences of several presumptive dehydrogenases identified in genomic sequencing projects of *B. halodurans* and *Clostridium difficule* (SEQ ID NO:50, SEQ ID NO:51, SEQ ID NO:52. SEQ ID NO:53). Although the sequences of these dehydrogenases are known, the substrate specificity of the enzymes having these sequences has been previously either erroneously assigned or unassigned. For example, the enzyme from *B. halodurans* (SEQ ID NO:50) has been annotated as sorbitol dehydrogenase (GenBank PID:PID:GI:10172799).

Example 26

Construction of the Expression Vectors pGTK74(LRXPD) and pGTK24(BHDH)

The expression vectors pGTK74(LRXPD) and pGTK74 (BHDH) were constructed from pGTK24 in two steps.

Figure 23:
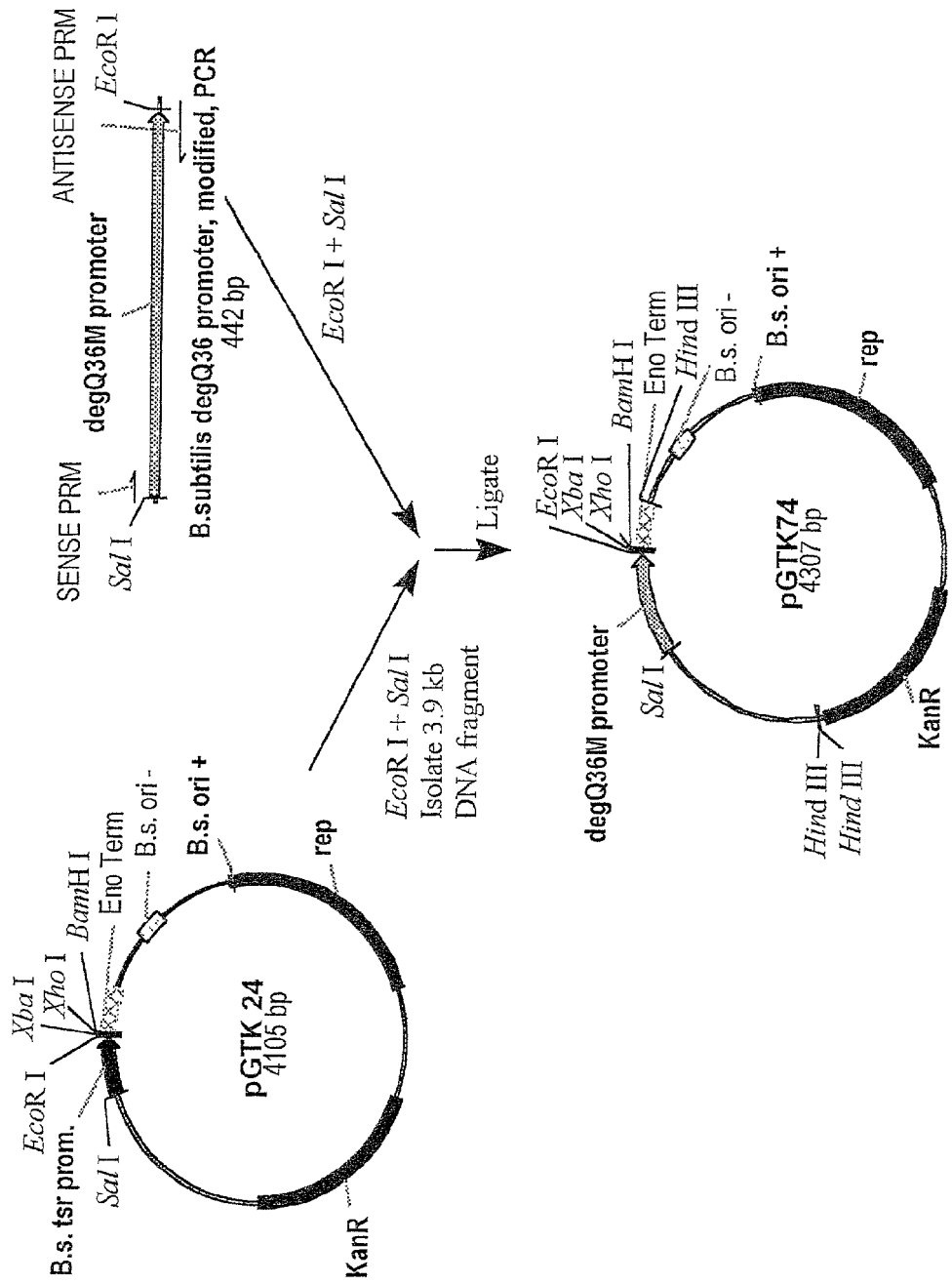
FIG. 23. Construction of plasmid pGTK74.

At the first step the *B.subtilis* aldolase promoter present in pGTK24 was replaced with the modified degQ promoter from the same organism. One of the modifications compared to the wild type degQ promoter was the introduction of the known degQ36 mutation [Msadek T, et al, *J. Bacteriol.* 173: 2366–2377 (1991)]. The modified degQ promoter was amplified by PCR using the chromosomal DNA of *B. subtilis* as the template and the two oligonucleotides oDEGQ 5 (SEQ ID NO:54, GGAGTCGAC-CATGGGAGCAC-CTCGCAAAAAGG) and DEGQ 3 (SEQ ID NO:55, GGAGAATTCACCTCCTTTCAGAGTC-CCGGGTATTTGATCTGTTACTA ATAGTG-TATCGTCTTTCGG) as primers. The product of this PCR was digested with the restriction endonucleases SalI and EcoRI and ligated with the large fragment of pGTK24 digested with the same enzymes. The resulting plasmid construction was named pGTK74 (FIG. 23).

Figure 24A:
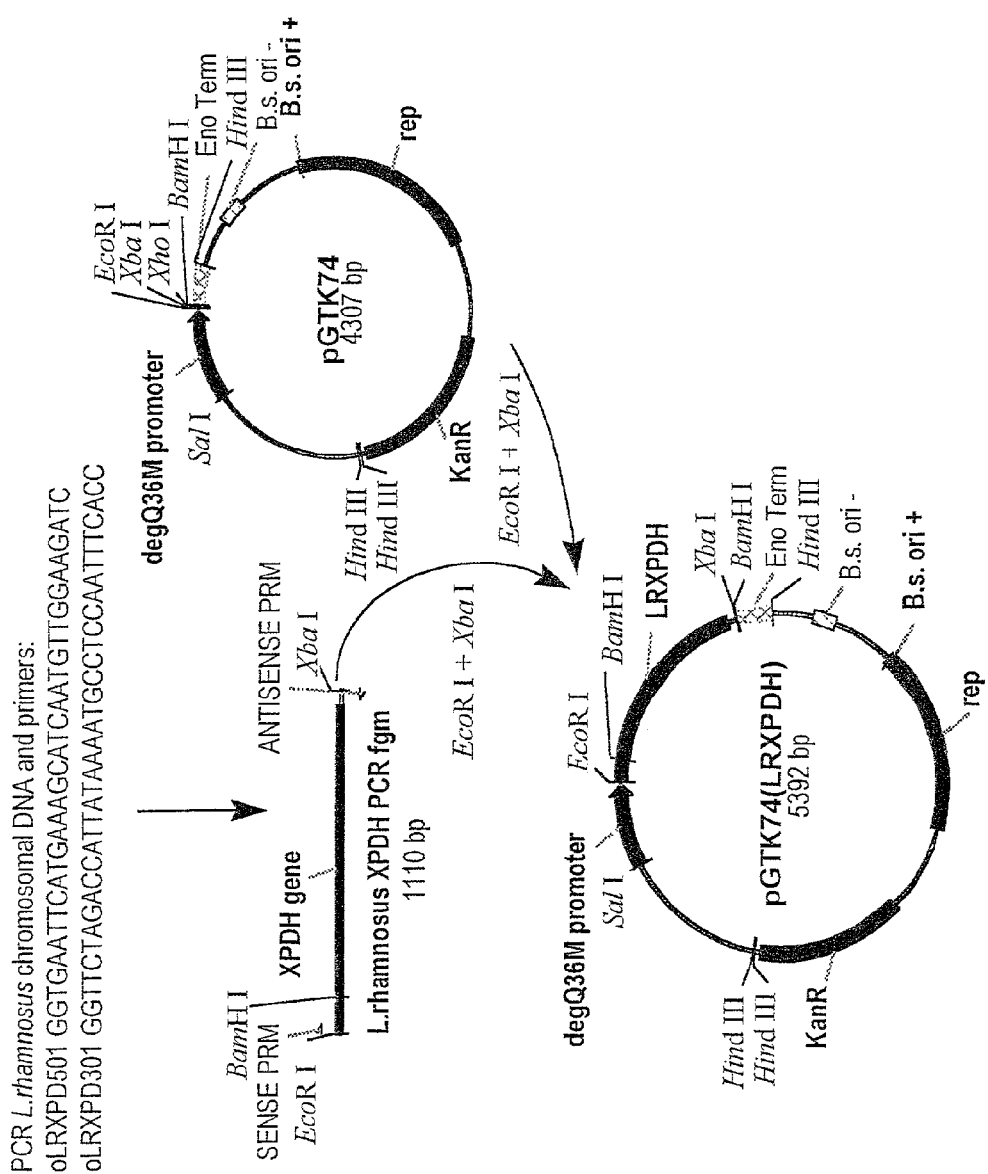
FIG. 24A: Construction of plasmid pGTK74(LRXPDH). Oligonucleotides oLRXPD501 and oLRXPD301 are SEQ ID Nos. 56 and 57, respectively.

At the second step, the coding area of the *L. rhamnosus* XPDH gene was amplified by PCR using the chromosomal DNA of *L. rhamnosus* as the template and the two oligonucleotide primers: oLRXPD 501 (SEQ ID NO:56, GGT-GAATTCATGAAAGCATCAATGTTGGAAGATC) and pLRXPD 301 (SEQ ID NO:57, GGTTCTAGACCAT-TATAAAATGCCTCCAATTTCACC). The DNA fragment generated by this reaction was digested with EcoRI and XbaI and ligated with EcoRI plus XbaI digested pGTK74. The construction scheme and the structure of the resulting *B. subtilis/E. coil* shuttle vector pGTK74(LRXPD) is illustrated by the FIG. 24A.

Figure 24B:
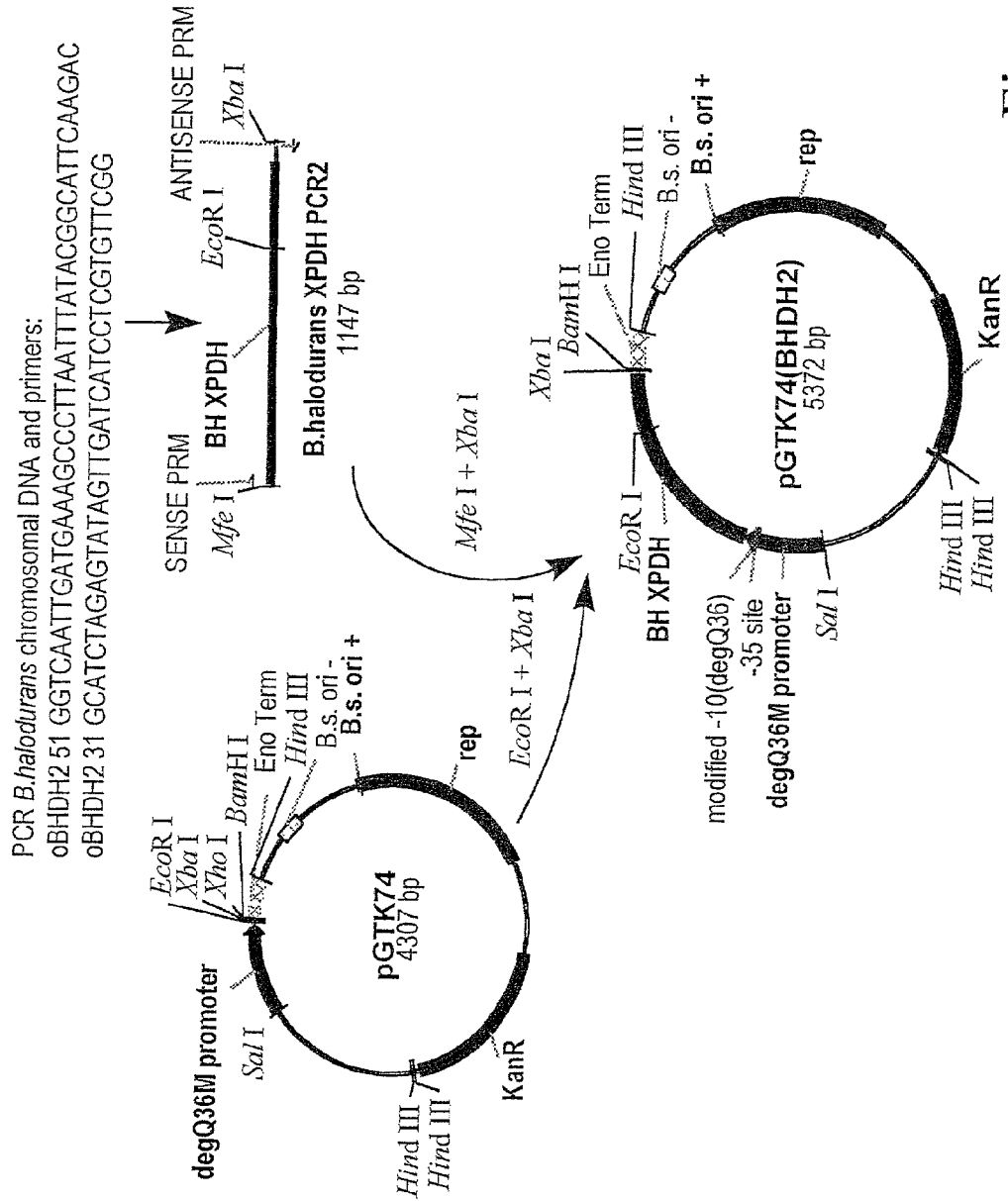
FIG. 24B: Construction of plasmid pGTK74(BHDH2). Oligonucleotides oBHDH2 51 and oBHDH2 31 are SEQ ID Nos. 58 and 59, respectively.

Similarly, the expression vector pGTK74(BHDH2) was constructed by amplifying the coding region of a *B. halodurans* gene homologous to the *L. rhamnosus* XPDH with the help of two oligonucleotide primers:oBHDH2 51 (SEQ ID NO:58, GGTCAATTGATGA-AAGCCCTTAATT-TATACGGCATTCAAGAC) and oBHDH2 31 (SEQ ID NO:59, GCATCTAGAGTATAGTTGATCATC-CTCGTGTTCGG). The resulting DNA fragment was digested with MfeI and XbaI and ligated with pGTK74 hydrolyzed with EcoRI and XbaI yielding expression vector pGTK74(BHDH2) (FIG. 24B).

Example 27

Expression of Xylitol-phosphate Dehydrogenase Genes from *L. rhamnosus* and *B. halodurans*

*B. subtilis* strain BD170 was transformed with pGTK74 (LRXPD) and pGTK74(BHDH2). The transformants were grown overnight in LB containing 25 mg/liter kanamycin, cell extract were prepared by sonication and the activity of XPDH activity was measured. The conditions for measuring the XPDH activity were similar to those used for measuring the xylitol dehydrogenase activity except that xylulose 5-phosphate was used as the substrate (usually at 5 mM concentration) instead of xylulose. The activities were approximately 0.3 U/mg protein for the XPDH from *L. rhamnosus* and about 0.5 U/mg protein for *B. halodurans* enzyme.

The stereospecificity of xylulose-phosphate reduction by the *B. halodurans* XPDH was verified by the following procedure. The reaction between D-xylulose 5-phosphate and NADH was conducted at 37° C. for several hours under the following conditions: 100 mM Tris-HC buffer, pH 7.0, 10 mM xylulose 5-phosphate, 10 mM NADH, 5 of the enzyme lysate. The reaction products were dephosphorylated with alkaline phosphatase and analyzed by HPLC. Only xylitol and xylulose (corresponding to the unreacted xylulose 5-phosphate) but no arabitol were found in the reaction mixture demonstrating that the "xylulose 5-phosphate reductase" (SEQ ID NO:50) from *B. halodurans* is indeed xylitol-phosphate dehydrogenase. It should be noted that among the highest-scoring four homologues of the *L. rhamnosus* XPDH, the enzyme from *B. holodurans* is the least homologous. This can be interpreted as an indication that the other three homologues (SEQ ID NO:51, 52 and 53) are most probably also xylitol-phosphate dehydrogenases.

Example 28

Production of Xylitol by the Recombinant *B. subtilis* Strains Expressing XPDH

*B. subtilis* strain GX7 was transformed with pGTK74 (LRXPD) and the transformants were cultivated in test tubes on LB medium containing 20% glucose under conditions of "medium aeration" (as defined in Example 8) for 10 days. At this time an aliquot of the culture broth was analyzed by HPLC and found to contain about 35 g/l xylitol. In the culture medium of a control strain (untransformed GX7) cultivated under the same conditions xylitol was not detectable.

Example 29

Over-expression of the *B. subtilis* glcUgdh Operon

Figure 25A:
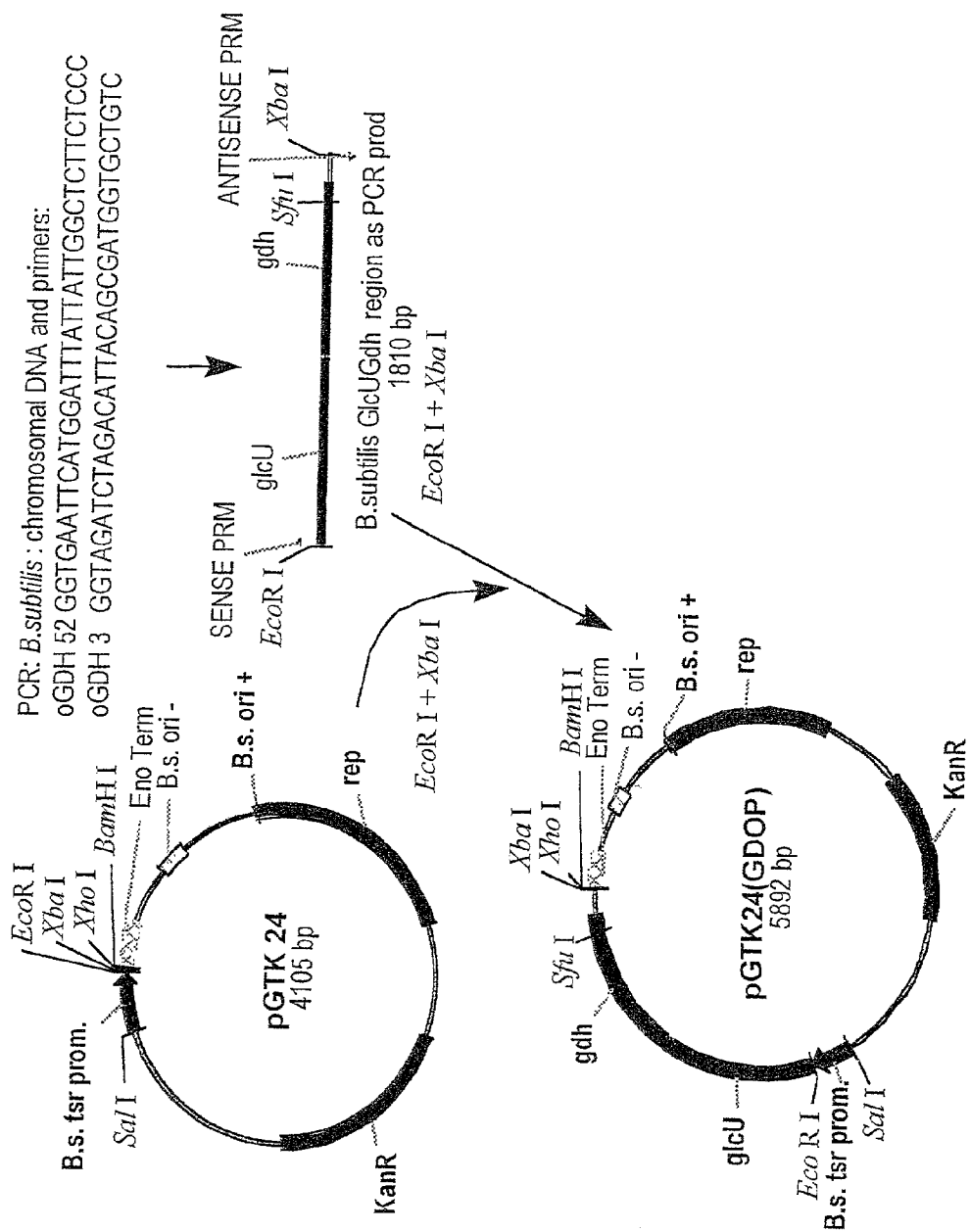
FIG. 25A: Construction of plasmid pGTK24(GDOP). Oligonucleotides oGDH 52 and oGDH 3 are SEQ ID Nos. 60 and 61, respectively.
Figure 25B:
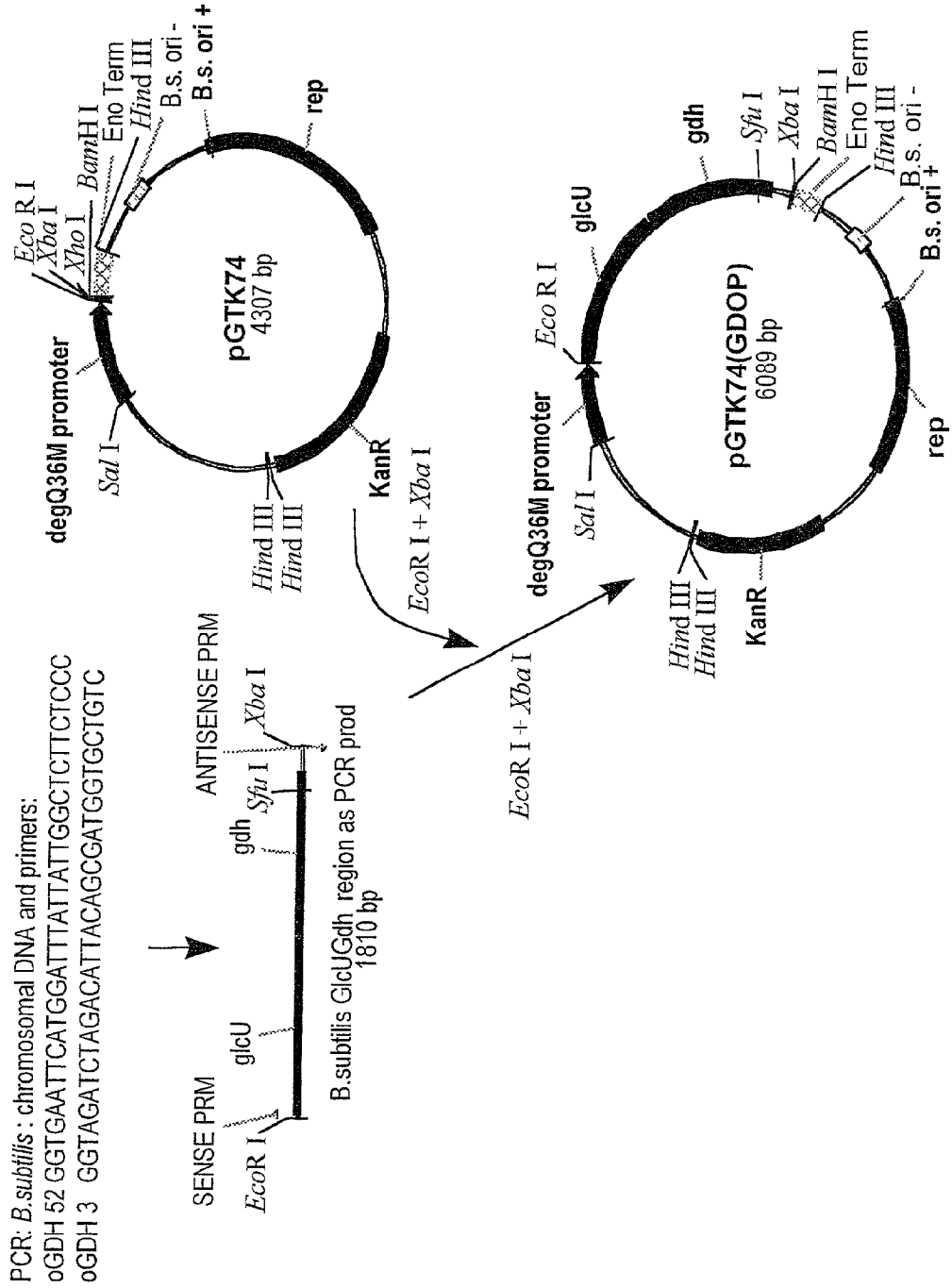
FIG. 25B: Construction of plasmid pGTK74(GDOP). Oligonucleotides oGDH 52 and oGDH 3 are SEQ ID Nos. 60 and 61, respectively.

The whole glcUgdh operon of *B. subtilis* was amplified by PCR using the two oligonucleotide primers oGDH52 (SEQ ID NO:60, GGTGAATTCATGGATTTATTATTG-GCTCTTCTCCC) and oGDH3 (SEQ ID NO:61, GGTA-GATCTAGACATTACAGCGATGGTGCTGTC). The DNA fragment obtained in the PCR was digested with EcoRI and XbaI and ligated with either pGTK24 digested with EcoRI plus XbaI or pGTK74 digested with the same pair of enzymes. Two expression vectors: pGTK24(GDOP) and pGTK74(GDOP) were obtained as the result of these experiments (illustrated by FIGS. 25A and 25B, respectively). Both plasmids were used to transform the *B. subtilis* strain BD170.

*B. subtilis* BD170 [pGTK24(GDOP)] and BD170 [pGTK74(GDOP)] strains were grown overnight in LB (25 mg/l kanamycin) at 37° C. The cultures were harvested and cellular extracts prepared as described above. Glucose dehydrogenase activity was measured by following the rate of NAD$^+$ reduction at 340 nm at 30° C. using glucose as a substrate. Reaction conditions were: 50 mM Tris-HCl (pH 7.5), 10 mM NAD$^+$, 2 mM MgCl$_2$, 10 mM glucose. Both types of transformants were found to contain similar levels of glucose dehydrogenase activity (about 1.5–2 U/mg protein). No activity could be measured in the untransformed BD170 (in wild-type *B. subtilis* glucose dehydrogenase is known to be expressed only during sporulation).

Figure 26:
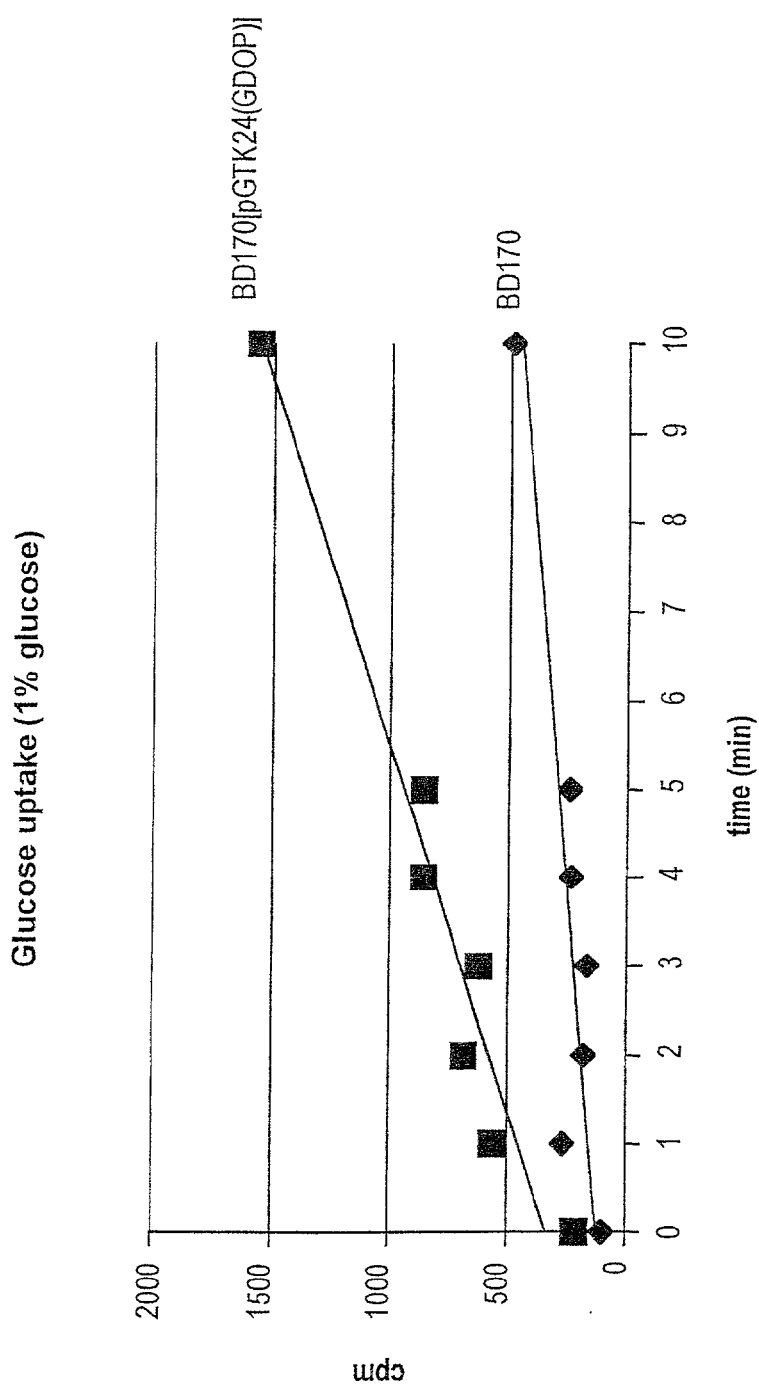
FIG. 26. Glucose update (1% glucose) rate (cpm vs. min) in a *B. subtilis* strain transformed with BD170[pGTK24 (GDOP)] and untransformed control strain (BD170).

*B. subtilis* BD 170 [pGTK24(GDOP)] was cultivated overnight in LB (25 mg/l kanamycin) at 37° C. under high aeration. 15 ml of the culture was harvested by centrifugation and the cells were washed with the ice-cold reaction buffer (50 mM Tris-HCl, pH 6,5; 150 mM NaCl). The cells were re-suspended in 800 μl of the reaction buffer. Sugar uptake was examined by using $^{14}$C-glucose (in the presence of different unlabelled glucose concentrations) at +37° C. $^{14}$C-glucose was added at t=0 and aliquots (100 l) were withdrawn every minute. The aliquots were deposited onto a nitrocellulose filter (0.2 m) and washed with 3 ml of ice-cold reaction buffer. The filters were dried and the radioactivity quantified using scintillation counter. Much higher glucose uptake rate in the *B. subtilis* strain transformed with pGTK24(GDOP) was found under all conditions tested. For example, in a solution containing 1% glucose the uptake rate of the transformed strain was approximately four times higher that in the untransformed wild-type strain (FIG. 26).

These results indicate that the glcUgdh operon is functional in *B. subtilis* also when expressed from a vegetative promoter and that it can indeed be used for enhancing the glucose flow into the pentose phosphate pathway.

Example 30

Purification and Partial Sequencing of Arabitol-phosphate Dehydrogenase from *Enterococcus avium*

*Enterococcus avium* ATCC 35655 was cultivated at 30° C. in 5 liters of a medium containing: peptone—10 g/l, yeast extract—5 g/l, beef extract 10 g/l, K$_2$HPO$_4$ 2 g/l, NaCl—5 g/l, MgSO$_4$—0.02 g/l, MnCl$_2$—0.05 g/l, ammonium citrate 2 g/l, Tween 20—1.1 ml/l, xylitol—20g/l, pH 6.5. The cultivation was terminated when the culture has reached early stationary phase (typically, after 48 hours of fermentation), the cells were separated by centrifugation (3000×g, 20 min), washed with water and re-suspended in 20 mM Tris hydrochloride, pH 7.2 containing 3 mM dithiothreitol (buffer A). The cells were incubated with 0.3% lysozyme (w/v) at 20° C. for 60 min, lysed by sonication (3×20 sec) and the extract was clarified by centrifugation (12,000×g, 20 min). The resulting supernatant was dialyzed against buffer A, applied to a Toyopearl DEAE 5PW column (21.5×159 mm) equilibrated with the same buffer, and eluted with a linear gradient (0 to 1 M) of NaCl. Fractions containing arabitol-phosphate dehydrogenase activity (assayed as described in Example 27) were pooled, concentrated on Amicon PM-30 membrane to 10 ml, and dialysed against buffer A. This preparation was further fractionated by chromatography on a Mono Q HR(5/5) column (Pharmacia LKB) with a linear gradient (0–1 M) of NaCl in the same buffer. Active fractions were pooled and applied to a Sepharose Blue CL6B (Pharmacia) column (10×50 mm) equilibrated with 50 mM Tris HCl buffer, pH 8.0, 100 mM NaCl, 3 mM DTT, and eluted with 3 mM NADH in the same buffer. Finally, the active fractions from Sepharose Blue chromatography were pooled and loaded onto a Phenyl Superose HR 5/5 (Pharmacia) column equilibrated with 30 mM Tris HCl, pH 7.4, 1.7 M (NH$_4$)$_2$SO$_4$, and eluted with 30 mM Tris HCl buffer, pH 7.4. Purified arabitol-phosphate dehydrogenase (approx. 0.2 mg, specific activity with 5 mM xylulose 5-phosphate as the substrate about 12 U/mg$_{protein}$) was dialyzed against water and lyophilized.

The stereospecificity of D-xylulose 5-phosphate reduction by the *E. avium* arabitol-phosphate dehydrogenase was verified by the following procedure. The reaction between D-xylulose 5-phosphate and NADH was conducted at 37° C. for several hours under the following conditions: 100 mM Tris-HCl buffer, pH 7.0, 10 mM xylulose 5-phosphate, 10 mM NADH, 1U of the enzyme. The reaction products were dephosphorylated with alkaline phosphatase and analyzed by HPLC. Only arabitol and xylulose (corresponding to the unreacted xylulose 5-phosphate) were found in the reaction mixture demonstrating that the "xylulose 5-phosphate reductase" from *E. avium* is an D-arabitol-phosphate dehydrogenase. There are no other arabitol-phosphate dehydrogenases described in the art.

The protein sequences were obtained through a commercial service provided by the Institute of Biotechnology, University of Helsinki. The following four peptide sequences were used in cloning the arabitol-phosphate dehydrogenase gene: (QYNLCPHR, SEQ ID NO: 62; EIEYIGSR, SEQ ID NO:63; KQGQFIQVGLFANK, SEQ ID NO:64; GAIMDEMITK, SEQ ID NO:65). A number of degenerate oligonucleotides were designed based on these sequences and tested as PCR primers with *E. avium* chromosomal DNA as the template. The best results were obtained with the pair of primers oXP-1F (sense primer, CARTATAATTTTGTCCICATMG, SEQ ID NO:66) and oXP-4R, (anti-sense primer, ATCATTTCRTCIATRTTI-ATIGCICC; SEQ ID NO:67) that generated a PCR product of about 0.65 kb. This PCR product was used as the hybridization probe to screen a gene library of *E. avium* constructed in the same way as the gene library of *L. rhamnosus* described in Example 25. Several strongly hybridizing phage clones were isolated, purified and converted to the phagemid form according to the methods recommended by Stratagene. One clone showing a restriction pattern overlapping the restriction pattern of the original 0.65 kb PCR product was used to sequence the arabitol-phosphate dehydrogenase gene. The sequence (SEQ ID NO:68) contains an open reading frame of 352 codons preceded by a typical ribosome binding site. The deduced amino acid sequence of arabitol-phosphate dehydrogenase from *E. avium* (SEQ ID NO:69) is homologous to a number of medium-chain dehydrogenases. Particularly high homology is observed with the deduced sequence of a protein from *B. halodurans* that is annotated in GenBank as "sorbitol dehydrogenase" (SEQ ID NO:70).

Example 31

Expression of the Arabitol-phosphate Dehydrogenases from *E. avium* and *B. halodurans* in *B. subtilis*

Figure 27A:
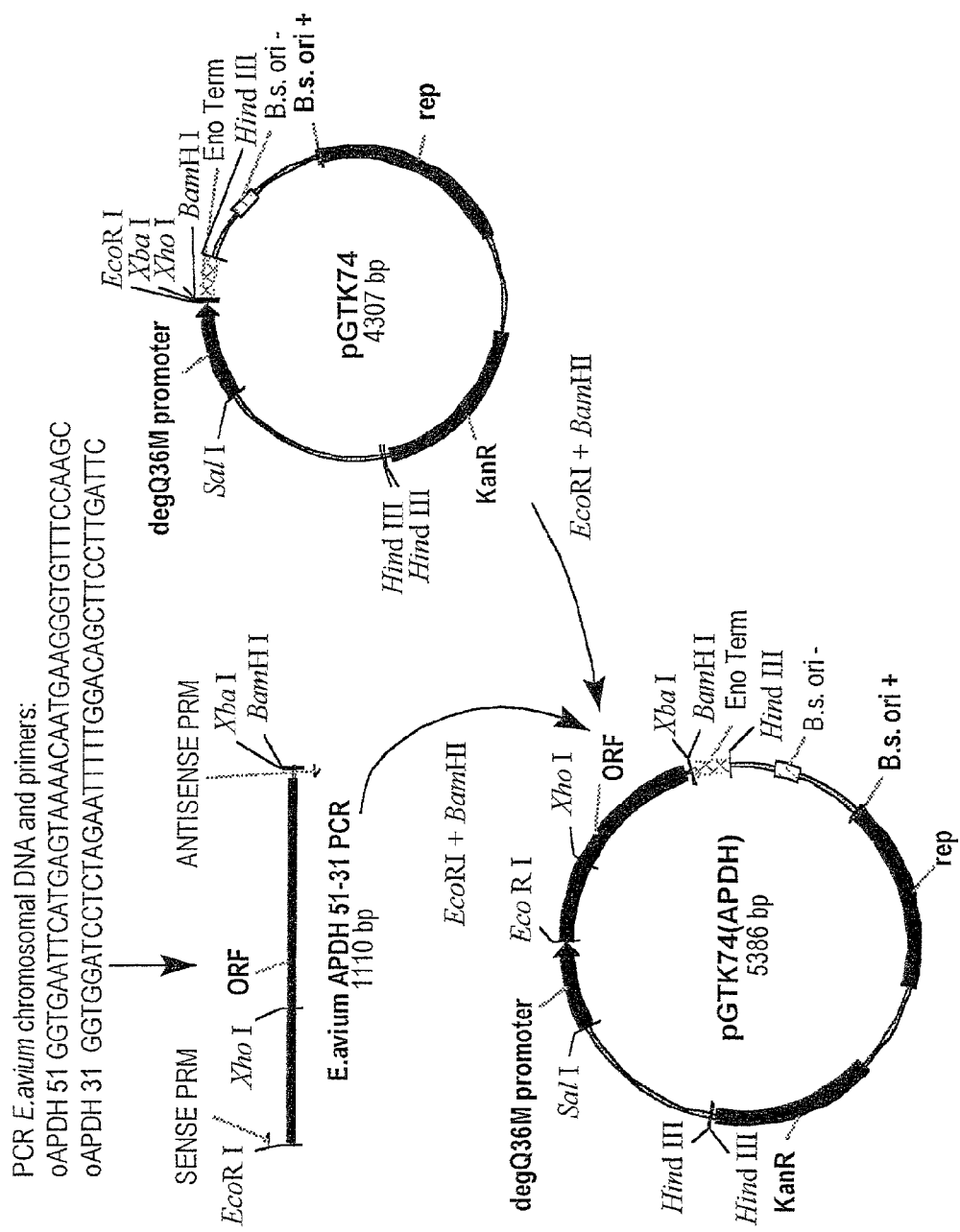
FIG. 27A: Construction of expression vector pGTK74(APDH). Oligonucleotides oAPDH51 and oAPDH31 are SEQ ID Nos. 71 and 72 respectively.
Figure 27B:
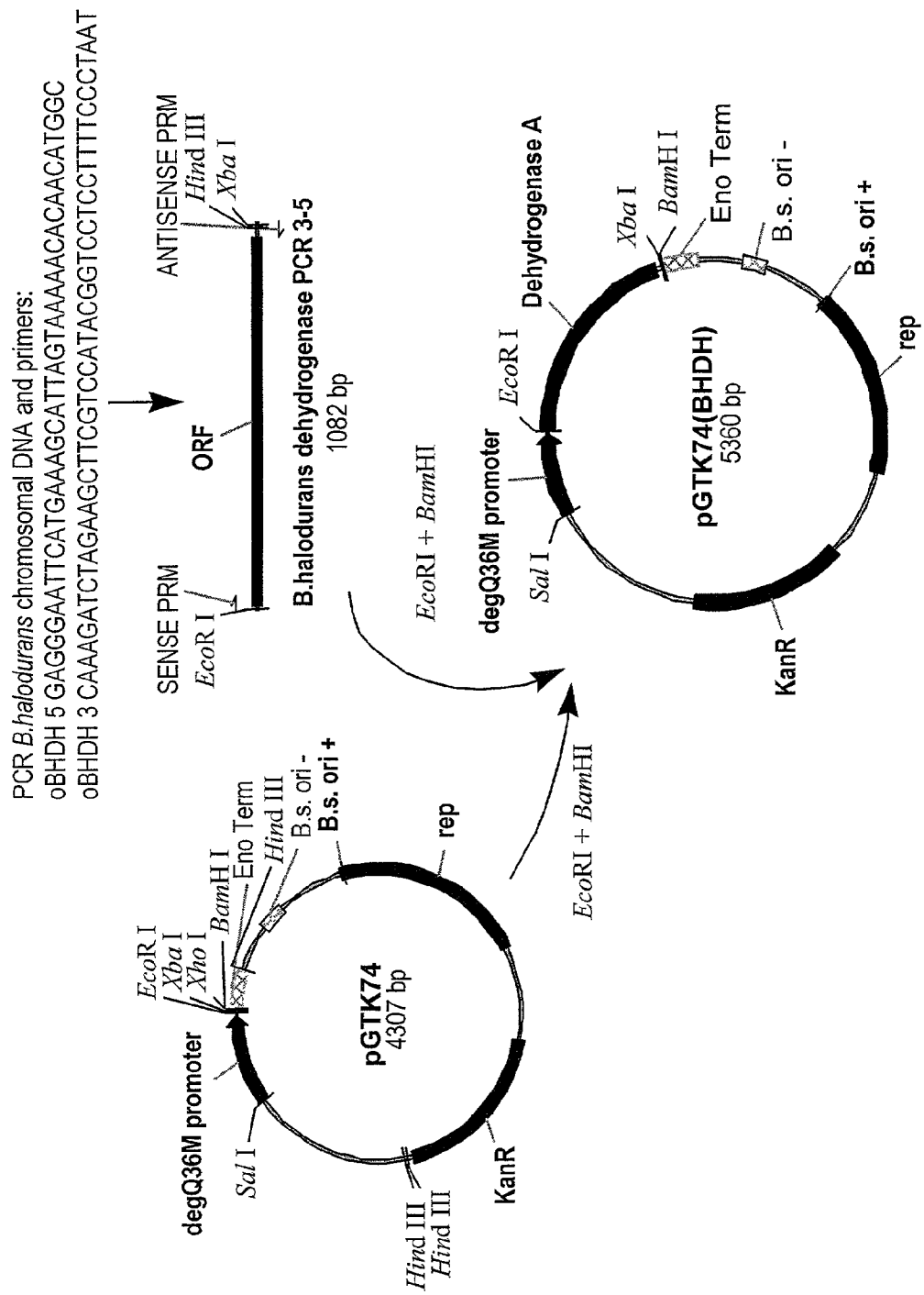
FIG. 27B: Construction of expression vector pGTK74(BHDH). Oligonucleotides oBHDH 5 and oBHDH 3 are SEQ ID Nos. 73 and 74 respectively.

Both arabitol-phosphate dehydrogenase genes were expressed using the same tools and methods as those used for the expression of xylitol-phosphate dehydrogenases (Example 26). Briefly, the coding regions of the two arabitol-phosphate dehydrogenase genes were amplified using the chromosomal DNA of the microorganism from which the enzyme was isolated and the appropriate PCR primers. In the case of *E. avium* the primers were oAPDH 51 GGTGAATTCATGAGTAAAACAATGAAGGGT-GTTTCCAAGC SEQ ID NO: 71) and the anti-sense primer oAPDH 31 GGTGGATCCTCTAGAATTTTTGGA-CAGCTTCCTTGATTC) SEQ ID NO: 72. For *B. halodurans,* the sense primer was oBHDH 5 (GAGGGAATTCAT-GAAAGCATTAGTAAAAACACAACATGGC, SEQ ID NO: 73) and the anti-sense primer was oBHDH 3 (CAAA-GATCTAGAAGCTTCGTCCATACGGTC-CTCCTTTTCCCTAAT, SEQ ID NO: 74). The resulting PCR products were digested with a mixture of restriction endonucleases BamHI and EcoRI and ligated with pGTK74 hydrolyzed with the same mixture of enzymes (FIGS. 27A and 27B). The resulting expression vectors pGTK74 (APDH)(FIG. 27A) and pGTK74(BHDH)(FIG. 27B) were used to transform *B. subtilis* strain BD170 and both were found to express "D-xylulose 5-phosphate reductase" activity at high levels. The stereospecificity of D-xylulose 5-phosphate reduction by the previously unknown enzyme from *B. halodurans* was determined as described in Example 30. It was found that this enzyme is indeed a D-arabitol-phosphate dehydrogenase.

Example 32

Production of Arabitol by the Recombinant Strains of *B.subtilis*

Plasmid pGTK74(APDH) was used to transform the pentulose-producing *B. subtilis* strain GX7. The strain was cultivated under the conditions of "medium aeration" (as defined in Example 8) in LB broth containing 10% glucose. Accumulation of arabitol in the culture medium reaching about 35–40 g/l was observed.

Appendix I—Table 32 and Table 33

TABLE 32

| Yeast Strains Used in the Current Work | | |
|---|---|---|
| H158 | | GPY55-15B_ (MAT_, leu2-3, leu2-112, ura3-52, trp1-289, his4-519, prb1, cir⁺) from Gregory Payne (Department of Biological Chemistry, University of California Los Angeles, Los Angeles, California 90095-3717, USA). |
| H475 | H158 + XR | Host, *P. stipitis* XYL1$_{mc}$ |
| H1104 | W303-1B | MATα ade2-1, his3-11/15, leu2-3/112, trp1-1, ura3-1, can1-100 - [Thomas B. J. and Rothstein R., Cell 56, 619–630 (1989)] |
| H1055 | H1104 tkl1, tkl2 | TKL1,2 deficient |
| H1057 | H1055 + pAOS67 | TKL1,2 deficient, *P. stipitis* XYL2$_{mc}$ |
| H1160 | H1104 + pAOS67 | Host, *P. stipitis* XYL2$_{mc}$ |
| H1499 | H1506 + GDH2 | TKL1,2 deficient, *P. stipitis* XYL2$_{int}$, *S. cerevisiae* GDH2$_{mc}$ |
| H1506 | H1055 + *P. s* XDH$_{int}$ | TKL1,2 deficient, *P. stipitis* XYL2$_{int}$ |
| H1520 | H1506 + DOG1 | TKL1,2 deficient, *P. stipitis* XYL2$_{int}$, *S. cerevisiae* DOG1$_{mc}$ |
| H1514 | H1104 + DOG1 | Host, DOG1$_{mc}$ |
| H1524 | H1506 + YEplac195 | TKL1,2 deficient, *P. stipitis* XYL2$_{int}$, YEplac195 |
| H1748 | H1052 + *T. r* XDH$_{mc}$ | host, *T. reesei* XYL2$_{mc}$ |
| H1741 | H1055 + *T. r* XDH$_{int}$ | TKL1,2 deficient, *T. reesei* XYL2$_{int}$ |
| H1743 | H1741 + GDH2 | TKL1,2 deficient, *T. reesei* XYL2$_{int}$, *S. cerevisiae* GDH2$_{mc}$ |
| H1854 | H1506 xk | TKL1,2,XKS1 deficient, *P. stipitis* XDH$_{int}$ |
| H1857 | H1741 pgi1 | TKL1,2, PGI1 deficient, *T. reesei* XYL2$_{int}$ |
| H1886 | H1104 + B1163 | Host, *S. cerevisiae* XYL2 homologue$_{mc}$ (YLR070C) |
| H1915 | H1857 + GDH2 | TKL1,2, PGI1 deficient, *T. reesei* XYL2$_{int}$, *S. cerevisiae* GDH2$_{mc}$ |

TABLE 32-continued

Yeast Strains Used in the Current Work

| | | |
|---|---|---|
| H1916 | H1857 + Yeplac195 | TKL1,2, PGI1 deficient, T. reesei XYL2$_{int}$, Yeplac195 |
| H2421 | H1741 + B1181 | TKL1,2 deficient, T. reesei XYL2$_{int}$, YEplac195 + PGK1 promoter and terminator |
| H2422 | H1741 + LTP1 | TKL1,2 deficient, T. reesei XYL2$_{int}$, S. cerevisiae LTP1$_{mc}$ |
| H2424 | H1741 + PPPase 2 | TKL1,2 deficient, T. reesei XYL2$_{int}$, Z. rouxii PPPase 2$_{mc}$ |
| H2425 | H1741 + DOG1 | TKL1,2 deficient, T. reesei XYL2$_{int}$, S. cerevisiae DOG1$_{mc}$ |
| H1346 | CEN.PK2 | Mat a leu2-3/112 ura3-52 trp1-289 his3d1 MAL2-8c SUC2 [Boles E., et al., Mol. Microbiol. 20, 65–76 (1996)] |
| H1347 | H1346 pfk26 pfk27 | PFK26, PFK27 deficient |
| H1759 | H1347 + pAOS64 | PFK26, PFK27 deficient, P. stipitis XYL2$_{mc}$ |
| H1764 | H1346 tkl1 | TKL1 deficient |
| H1765 | H1764 + pAOS67 | TKL1 deficient, P. stipitis XYL2$_{mc}$ |
| H1766 | H1346 + paOS67 | Host, P. stipitis XYL2$_{mc}$ |
| H1052 | ENY.WA-1A | MATα ura3-52 leu2-3/112 trp1-289 his3d1 MAL2-8c MAL3 SUC3 [Boles E. and Zimmermann F. K., Curr. Genet. 23, 187–191 (1993)] |
| H1054 | H1052 pgi1 | PGI1 deficient |
| H1117 | H1054 + pAOS67 | PGI1 deficient, P. stipitis XYL2$_{mc}$ |
| H1768 | H4/pRB4 | Reduced PGI1 activity |
| H1770 | H5/pRB5 | Reduced PGI1 activity |
| H1772 | H1768 + pAOS67 | Reduced PGI1 activity, P. stipitis XYL2$_{mc}$ |
| H1774 | H1770 + pAOS67 | Reduced PGI1 activity, P. stipitis XYL2$_{mc}$ |
| H1053 | H1052 pgi1 | PGI1 deficient |
| H1115 | H1053 + pAOS66 | PGI1 deficient, P. stipitis XYL2$_{mc}$ |
| H1451 | H1053xH1055 pgi1, tkl1, tkl2 | TKL1,2, PGI1 deficient |
| H1453 | H1451 + XDH | TKL1,2, PGI1 deficient, P. stipitis XYL2$_{mc}$ |
| H1576 | H1053 idp2 | PGI1, IDP2 deficient |

$_{mc}$ = multicopy plasmid
$_{int}$ = integrated into the genome

TABLE 33

Plasmid Vectors Used for Yeast Genetic Manipulation in the Current Work

| | |
|---|---|
| pUC19 | Pharmacia Biotech, Uppsala, Sweden |
| Bluescript SK (−) | Stratagene, USA |
| Bluescribe M13 | Stratagene, USA |
| pAJ401 (URA3)[1] | Saloheimo A., et al., Mol. Microbiol. 13, 219–228 (1994) |
| pFA6-kanMX2 | Wach A., et al. Yeast 10, 1791–1808 (1994) |
| pRS423 (HIS3) | Christianson T. W., et al., Gene 110, 119–122 (1992) |
| pRSETC | Invitrogen, The Netherlands |
| pMA91 (LEU2) | Mellor J, et al., Gene 24, 1–14 (1983) |
| pZErO™-1 | Invitrogen, The Netherlands |
| YEplac181 (LEU2) | Gietz R. D. and Sugino A., Gene 74, 527–534 (1988) |
| YEplac195 (URA3) | Gietz R. D. and Sugino A., Gene 74, 527–534 (1988) |
| YEp24H (URA3) | Aalto M., et al., Proc. Natl. Acad. Sci. USA 94, 7331–7336 (1997) |
| YEpMSP3-T | YEplac181 + S. cerevisiae GDH2, Boles E., et al., Eur. J. Biochem. 217, 469–477 (1993) |
| B609 | Middle ADH1 promoter and terminator in pBluescribe M13, Ruohonen L., et al., J. Biotechnol. 39, 193–203 (1995) |
| B713 | URA3 gene as a 1,1 kb HindIII fragment in Bluescript KS (+), Toikkanen J., et al., Yeast 12, 425–438 (1996) |
| pAOS63 (LEU2) | P. stipitis XYL2 in pMA91 |
| pAOS64 (URA3) | P. stipitis XYL2 with PGK1 promoter and terminator in YEp24H |
| pAOS66 (LEU2) | P. stipitis XYL1 with PGK1 promoter ans terminator, and P. stipitis XYL2 with middle ADH1 promoter and terminator in pMA91 |
| pAOS67 (HIS3) | P. stipitis XYL2 with PGK1 promoter and terminator in pRS423 |
| B955 | 71–450 bp and 781–1135 bp fragments of URA3 in Bluescript SK (−), Toikkanen J. and Keränen S., submitted for publication (1999) |
| B995 | P. stipitis XYL2 in NcoI site of URA3 |
| B1003 (KMX2) | pAOS67 + kan$^r$, kanamycin/G418 resistance |
| B1007 (URA3) | YEplac195 + GDH2, S. cerevisiae GDH2 from YEpMSP3-T in YEplac195 |
| B1009 | Bluescript SK (−) + IDP2, 5′ 491 bp and 3′ 158 bp fragments of S. cerevisiae IDP2 in Bluescript SK (−) |
| B1011 | Bluescript SK (−) + IDP2 disruption, 1,2 kbp URA3 gene from B713 ligated into B1009 HindIII site between the IDP2 fragments |
| B1016 (LEU2) | YEp11Hp + DOG1, DOG1 in YEplac181 [Santz P., et al., Yeast 10, 1195–1202 (1994)] in YEplac181 as HindIII-PstI fragment |
| B1020 (URA3) | YEplac195 + DOG1, S. cerevisiae DOG1 with middle ADH1 promoter and terminator in YEplac195 |
| B1025 | pRSETC + XKS1 |
| B1068 | B955 + XYL2, T. reesei XYL2 with PGK1 promoter and terminator in B955 between URA3 fragments |
| B1073 (URA3) | pAJ401 + XYL2, T. reesei XYL2 in pAJ401 |
| B1070 (URA3) | YEplac195 + XYL2, T. reesei XYL2 in YEplac195 |
| B1087 | TKL1 disruption cassette, pUC19 containing TKL1 gene disrupted with URA3, Schaaff-Gerstenschläger I. and Zimmermann F. K., Curr. Genet. 24, 373–376 (1993) |
| B1154 | Bluescript SK (−) + xks disruption cassette, S. cerevisiae XKS1 disrupted with kanMX2 fragment |
| B1163 (LEU2) | pMA91 + YLR070C, S. cerevisieae XYL2 homologue in pMA91 |

TABLE 33-continued

Plasmid Vectors Used for Yeast Genetic Manipulation in the Current Work

| | |
|---|---|
| B1181 (URA3) | YEplac195 + PGK1, YEplac195 + PGK1 promoter and terminator from pMA91 |
| B1185 | Bluescript + HIS3, DrdI fragment from pRS423 containing HIS3 in Bluescript SK (−) |
| B1186 | Bluescript + PGI1, S. cerevisiae PGI1 in Bluescript SK (−) |
| B1187 | B1186 + distrubted PGI1, HIS3 from B1185 ligated into EcoRI-BstBI site of PGI1 in B1186 |
| B1449 (URA3) | B1181 + LTP1, S. cerevisiae LTP1 with PGK1 promoter and terminator in YEplac195 |
| B1450 (URA3) | B1181 + PPPase2, Z. rouxii PPPase 2 with PGK1 promoter and terminator in YEplac195 |

[1] The selection gene of the multicopy expression vector

Having now fully described the invention, it will be understood by those with skill in the art that the invention may be performed within a wide and equivalent range of conditions, parameters and the like, without affecting the spirit or scope of the invention or any embodiment thereof. All references cited herein are fully incorporated herein by reference.

What is claimed is:

1. A method for the production of xylitol, said method comprising:
   (A) cultivating a genetically modified xylulose-5-phosphate producing, bacterial, yeast or fungal host, the genetic modification of which increases the expression of xylitol phosphate dehydrogenase in said host during said cultivating as compared to said activity in said host prior to being genetically modified, on a carbon source other than D-xylose, D-xylulose, mixtures of D-xylose and D-xylulose, and polymers and oligomers containing D-xylose or D-xylulose as major components, wherein said modification comprises introducing one or more genes encoding said xylitol phosphate dehydrogenase to said host wherein said xylitol phosphate dehydrogenase is *L. rhamnosus* xylitol 1-phosphate dehydrogenase or *B. halodurans* xylitol 1-phosphate dehydrogenase. or *C. difficile* xylitol 1-phosphate dehydrogenase;
   (B) producing xylitol during said cultivating of part (A) by using said host to convert one or more pentose phosphate metabolic pathway intermediates in said host into said xylitol; and
   (C) recovering said xylitol that is produced in part (B); wherein the amount or rate of said xylitol production in said genetically modified microbial host is enhanced as compared to said amount or rate of xylitol production in said host prior to being said genetically modified.

2. The method of claim 1, wherein said xylitol phosphate dehydrogenase is *L. rhamnosus* xylitol 1-phosphate dehydrogenase.

3. The method of claim 2, wherein said. *L. rhamnosus* xylitol phosphate dehydrogenase comprises the amino acid sequence of SEQ ID NO:49.

4. The method of claim 3, wherein said *L. rhamnosus* xylitol phosphate dehydrogenase is encoded by a gene that comprises the nucleic acid sequence of SEQ ID NO:48.

5. The method of claim 1, wherein said xylitol phosphate dehydrogenase is *B. halodurans* xylitol 1-phosphate dehydrogenase.

6. The method of claim 5, wherein said *B. halodurans* xylitol phosphate dehydrogenase comprises the amino acid sequence of SEQ ID NO:50.

7. The method of claim 1, wherein said xylitol phosphate dehydrogenase is a *C. difficile* xylitol 1-phosphate dehydrogenase.

8. The method of claim 7, wherein said *C. difficile* xylitol phosphate dehydrogenase comprises the amino acid sequence of a sequence selected from the group consisting of SEQ ID NOs:51, 52 and 53.

* * * * *

SEQUENCE LISTING

```
<160> NUMBER OF SEQ ID NOS: 70

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
caatagcgac ggagagttag g                                         21

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
cgacgaattc cggcgtcagc ctgaatgg                                  28

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
cgacaagctt atcgaatcgg ctgatttgg                                 29

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
ccaacgtcga cgaaatcaga gacgccg                                   27

<210> SEQ ID NO 5
```

```
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
cccgaattct gtcctcctta tgtagcctg                                    29

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
ccgagaattc atgaaacagt atttgattgc cccc                              34

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
cctctagagg atccaaaagc gacgccgcga atatcttcaa ac                     42

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
cccggatcca agtaataaaa agaccgccg                                    29

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
cccaagcttt ccctctatca aaaaatgcgg                                   30

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
gttgaattcg cgtcgacgcg ttgctggcgt ttttcc                            36

<210> SEQ ID NO 11
<211> LENGTH: 53
```

```
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
caagtgatca taaaatttat gaacgtatag caaccactga gcgtcagacc ccg      53

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
aattaagctt tccggatcct cgagtctaga ccgaattccc g                   41

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
tcgacgggaa ttcggtctag actcgaggat ccggaaagct t                   41

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
cgatagtact tgcttgaaac ccaggacaat                                30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
cgatggatcc gggaccccta tctagcgaac                                30

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16
gaggaattca tgaaggcatt agtattagag aaagc                          35

<210> SEQ ID NO 17
<211> LENGTH: 39
<212> TYPE: DNA
```

```
<213> ORGANISM: Artificial Sequence
<220> FEATURE:
<223> OTHER INFORMATION: Description of Artificial Sequence:
      Oligonucleotide

<400> SEQUENCE: 17
gaggaagctt ggatccagca caattttcac atcagtcgc                              39

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18
ccacggatcc gtcaagagta cttgaaagg                                         29

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19
caccgtcgac gttccatctt ttcatcccc                                         29

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
gaacaggatc cagcatgact gacttaacta                                        30

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
gtattggatc ccttggatgc caaaagtta                                         29

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
ccagtgatat cgaggatgag attagtac                                          28

<210> SEQ ID NO 23
<211> LENGTH: 28
<212> TYPE: DNA
<213> ORGANISM: Artificial Sequence
```

```
<220> FEATURE:
<223> OTHER INFORMATION: Description of Artificial Sequence:
      Oligonucleotide

<400> SEQUENCE: 23
ccagtgatat ctgtacttgt cagggcat                                          28

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 24
tcagggtcct gccagca                                                      17

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 25
cgctaggaac gatctcc                                                      17

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 26
tgagtaagct tatggcagaa ttttcagct                                         29

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 27
ttgtcaagct tttgtttact caggcccTT                                         29

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 28
ggaagatcta taatgacaat tgaaaaacca aaaatatcg                              39

<210> SEQ ID NO 29
<211> LENGTH: 38
<212> TYPE: DNA
<213> ORGANISM: Artificial Sequence
<220> FEATURE:
```

<223> OTHER INFORMATION: Description of Artificial Sequence:
      Oligonucleotide

<400> SEQUENCE: 29
ggaagatctt tataactctt tttttaaaaa ctgtttgg                                    38

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 30
agaagaggat ccataatgac tcagggtgaa aagatctc                                    38

<210> SEQ ID NO 31
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 31
agaagaggat ccttacaatt cactatctaa gaatgattca c                                41

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 32
ggcacgctgc agagagcgat ttgttcacat                                             30

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 33
cgaccggtcg actaccagcc taaaaatgtc                                             30

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 34
gacagcctgc aattgtatgt                                                        20

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence:

Oligonucleotide

<400> SEQUENCE: 35
gggcccaagc tttgtactga tcgcc                                    25

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 36
gggcccaagc ttgacgcggt ggaatctag                                29

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 37
cactagtgtc agtggaagc                                           19

<210> SEQ ID NO 38
<211> LENGTH: 483
<212> TYPE: DNA
<213> ORGANISM: Lactobacillus rhamnosus
<220> FEATURE:
<221> NAME/KEY: CDS
<222> LOCATION: (1)..(480)

<400> SEQUENCE: 38

```
atg act cag ggc gaa aag atc tca gta gca ttc gta tgc ctt ggt aac    48
Met Thr Gln Gly Glu Lys Ile Ser Val Ala Phe Val Cys Leu Gly Asn
 1               5                  10                  15 atc tgt cgt tcg cct atg gct gaa gcg gtt ttc cgc cac act gta aag    96
Ile Cys Arg Ser Pro Met Ala Glu Ala Val Phe Arg His Thr Val Lys
             20                  25                  30 agc aaa ggt ctg gag gat agg ttc agt aag atc gat tca ttc ggt acc   144
Ser Lys Gly Leu Glu Asp Arg Phe Ser Lys Ile Asp Ser Phe Gly Thr
         35                  40                  45 ggt agt tgg cac acc ggg gag acg cca gac cgc aga tca gtc tct acc   192
Gly Ser Trp His Thr Gly Glu Thr Pro Asp Arg Arg Ser Val Ser Thr
     50                  55                  60 tgt cgc tcc cac ggt gtt cca atc gat cat agg gca aag cag ata agg   240
Cys Arg Ser His Gly Val Pro Ile Asp His Arg Ala Lys Gln Ile Arg
 65                  70                  75                  80 cca tcg cat ttc agt gaa ttc gat tac gtc ctc tgc atg gat gac atg   288
Pro Ser His Phe Ser Glu Phe Asp Tyr Val Leu Cys Met Asp Asp Met
                 85                  90                  95 aat tta cgt aat ctg cgt cgc atg caa cca aag gag acg aaa gct agg   336
Asn Leu Arg Asn Leu Arg Arg Met Gln Pro Lys Glu Thr Lys Ala Arg
            100                 105                 110 gtg gaa tta ttt ggc aat tgg aac aac agt aac ggt aaa ttt gac acg   384
Val Glu Leu Phe Gly Asn Trp Asn Asn Ser Asn Gly Lys Phe Asp Thr
        115                 120                 125 att gtg gac gac cct tat tac ggc ggc gtt gat ggt ttt gaa cac aac   432
Ile Val Asp Asp Pro Tyr Tyr Gly Gly Val Asp Gly Phe Glu His Asn
    130                 135                 140
```

```
ttt cgt caa atc aca cat ttc agc gag tca ttc cta gac agt gaa ttg       480
Phe Arg Gln Ile Thr His Phe Ser Glu Ser Phe Leu Asp Ser Glu Leu
145                 150                 155                 160 taa                                                                    483

<210> SEQ ID NO 39
<211> LENGTH: 160
<212> TYPE: PRT
<213> ORGANISM: Lactobacillus rhamnosus

<400> SEQUENCE: 39

Met Thr Gln Gly Glu Lys Ile Ser Val Ala Phe Val Cys Leu Gly Asn
1               5                   10                  15

Ile Cys Arg Ser Pro Met Ala Glu Ala Val Phe Arg His Thr Val Lys
                20                  25                  30

Ser Lys Gly Leu Glu Asp Arg Phe Ser Lys Ile Asp Ser Phe Gly Thr
            35                  40                  45

Gly Ser Trp His Thr Gly Glu Thr Pro Asp Arg Arg Ser Val Ser Thr
        50                  55                  60

Cys Arg Ser His Gly Val Pro Ile Asp His Arg Ala Lys Gln Ile Arg
65                  70                  75                  80

Pro Ser His Phe Ser Glu Phe Asp Tyr Val Leu Cys Met Asp Asp Met
                85                  90                  95

Asn Leu Arg Asn Leu Arg Arg Met Gln Pro Lys Glu Thr Lys Ala Arg
                100                 105                 110

Val Glu Leu Phe Gly Asn Trp Asn Asn Ser Asn Gly Lys Phe Asp Thr
            115                 120                 125

Ile Val Asp Asp Pro Tyr Tyr Gly Gly Val Asp Gly Phe Glu His Asn
        130                 135                 140

Phe Arg Gln Ile Thr His Phe Ser Glu Ser Phe Leu Asp Ser Glu Leu
145                 150                 155                 160

<210> SEQ ID NO 40
<211> LENGTH: 483
<212> TYPE: DNA
<213> ORGANISM: Unknown Organism
<220> FEATURE:
<221> NAME/KEY: CDS
<222> LOCATION: (1)..(480)
<223> OTHER INFORMATION: Description of Unknown Organism: PPPase2

<400> SEQUENCE: 40 atg act cag ggt gaa aag atc tca gtg gca ttc gta tgc ctt ggt aac        48
Met Thr Gln Gly Glu Lys Ile Ser Val Ala Phe Val Cys Leu Gly Asn
1               5                   10                  15 att tgt cgc tca cca atg gct gaa gca gtt ttc cgc cat act gtg aag        96
Ile Cys Arg Ser Pro Met Ala Glu Ala Val Phe Arg His Thr Val Lys
                20                  25                  30 agt aaa ggt ttg gag gat aga ttt agt aag atc gat tca ttt ggt act       144
Ser Lys Gly Leu Glu Asp Arg Phe Ser Lys Ile Asp Ser Phe Gly Thr
            35                  40                  45 ggt ggt tgg cac act ggg gag aca cca gat cgc aga tcc gtc tct acc       192
Gly Gly Trp His Thr Gly Glu Thr Pro Asp Arg Arg Ser Val Ser Thr
        50                  55                  60 tgt cgt tct cat gga gtc cca gtt gat cat agg gca aag caa ata aaa       240
Cys Arg Ser His Gly Val Pro Val Asp His Arg Ala Lys Gln Ile Lys
65                  70                  75                  80 cca gca cat ttc aat gaa ttt gat tat atc ctc tgt atg gat gac atg       288
Pro Ala His Phe Asn Glu Phe Asp Tyr Ile Leu Cys Met Asp Asp Met
                85                  90                  95
```

```
aat tta cgc aat cta cgt cgt atg cag cca aag gaa tca aaa gct aga    336
Asn Leu Arg Asn Leu Arg Arg Met Gln Pro Lys Glu Ser Lys Ala Arg
        100                 105                 110 gta gaa ttg ttt ggt aat tgg aat aaa agt aat ggt aaa ttt gaa act    384
Val Glu Leu Phe Gly Asn Trp Asn Lys Ser Asn Gly Lys Phe Glu Thr
    115                 120                 125 att gtt gat gat cct tat tac ggt ggt gtt gat gga ttt gaa cat aat    432
Ile Val Asp Asp Pro Tyr Tyr Gly Gly Val Asp Gly Phe Glu His Asn
130                 135                 140 ttc cgt caa atc aca cat ttt tgt gaa tca ttc tta gat agt gaa ttg    480
Phe Arg Gln Ile Thr His Phe Cys Glu Ser Phe Leu Asp Ser Glu Leu
145                 150                 155                 160 taa                                                                483

<210> SEQ ID NO 41
<211> LENGTH: 160
<212> TYPE: PRT
<213> ORGANISM: Unknown Organism
<220> FEATURE:
<223> OTHER INFORMATION: Description of Unknown Organism: PPPase2

<400> SEQUENCE: 41

Met Thr Gln Gly Glu Lys Ile Ser Val Ala Phe Val Cys Leu Gly Asn
 1               5                  10                  15

Ile Cys Arg Ser Pro Met Ala Glu Ala Val Phe Arg His Thr Val Lys
            20                  25                  30

Ser Lys Gly Leu Glu Asp Arg Phe Ser Lys Ile Asp Ser Phe Gly Thr
        35                  40                  45

Gly Gly Trp His Thr Gly Glu Thr Pro Asp Arg Arg Ser Val Ser Thr
    50                  55                  60

Cys Arg Ser His Gly Val Pro Val Asp His Arg Ala Lys Gln Ile Lys
65                  70                  75                  80

Pro Ala His Phe Asn Glu Phe Asp Tyr Ile Leu Cys Met Asp Asp Met
                85                  90                  95

Asn Leu Arg Asn Leu Arg Arg Met Gln Pro Lys Glu Ser Lys Ala Arg
            100                 105                 110

Val Glu Leu Phe Gly Asn Trp Asn Lys Ser Asn Gly Lys Phe Glu Thr
        115                 120                 125

Ile Val Asp Asp Pro Tyr Tyr Gly Gly Val Asp Gly Phe Glu His Asn
    130                 135                 140

Phe Arg Gln Ile Thr His Phe Cys Glu Ser Phe Leu Asp Ser Glu Leu
145                 150                 155                 160

<210> SEQ ID NO 42
<211> LENGTH: 25
<212> TYPE: PRT
<213> ORGANISM: Lactobacillus rhamnosus

<400> SEQUENCE: 42

Met Lys Ala Ser Met Leu Glu Asp Leu Asn Lys Phe Ser Val Lys Glu
 1               5                  10                  15

Ile Asp Ile Pro Ser Pro Lys Lys Asp
            20                  25

<210> SEQ ID NO 43
<211> LENGTH: 10
<212> TYPE: PRT
<213> ORGANISM: Lactobacillus rhamnosus
```

```
<400> SEQUENCE: 43

Glu Trp Thr Asn Ser Ile Gln Leu Val Arg
1               5                   10

<210> SEQ ID NO 44
<211> LENGTH: 13
<212> TYPE: PRT
<213> ORGANISM: Lactobacillus rhamnosus

<400> SEQUENCE: 44

Phe Gly Gly Phe Glu Gln Tyr Val Ser Val Pro Ala Arg
1               5                   10

<210> SEQ ID NO 45
<211> LENGTH: 14
<212> TYPE: PRT
<213> ORGANISM: Lactobacillus rhamnosus

<400> SEQUENCE: 45

Gly Leu Asp Glu Gly Cys Thr His Val Ile Asn Ser Ala Lys
1               5                   10

<210> SEQ ID NO 46
<211> LENGTH: 26
<212> TYPE: DNA
<213> ORGANISM: Artificial Sequence
<220> FEATURE:
<223> OTHER INFORMATION: oLRXPD 53 primer
<221> NAME/KEY: misc_feature
<222> LOCATION: (9)..(9)
<223> OTHER INFORMATION: n represents an inosine residue
<221> NAME/KEY: misc_feature
<222> LOCATION: (12)..(12)
<223> OTHER INFORMATION: n represents an inosine residue
<221> NAME/KEY: misc_feature
<222> LOCATION: (18)..(18)
<223> OTHER INFORMATION: n represents an inosine residue

<400> SEQUENCE: 46
atgaargcnt cnatgttnga rgattt                                          26

<210> SEQ ID NO 47
<211> LENGTH: 32
<212> TYPE: DNA
<213> ORGANISM: Artificial Sequence
<220> FEATURE:
<223> OTHER INFORMATION: oLRXPD 31 primer
<221> NAME/KEY: misc_feature
<222> LOCATION: (6)..(6)
<223> OTHER INFORMATION: n is an inosine residue
<221> NAME/KEY: misc_feature
<222> LOCATION: (9)..(9)
<223> OTHER INFORMATION: n is an inosine residue
<221> NAME/KEY: misc_feature
<222> LOCATION: (15)..(15)
<223> OTHER INFORMATION: n is an inosine residue
<221> NAME/KEY: misc_feature
<222> LOCATION: (18)..(18)
<223> OTHER INFORMATION: n is an inosine residue
<221> NAME/KEY: misc_feature
<222> LOCATION: (24)..(24)
<223> OTHER INFORMATION: n is any nucleotide of a, g, t or c

<400> SEQUENCE: 47
gcrttnacna rytgnatnga rttngtccay tc                                   32

<210> SEQ ID NO 48
<211> LENGTH: 2123
<212> TYPE: DNA
```

<213> ORGANISM: Lactobacillus rhamnosus

<400> SEQUENCE: 48

| | | | | | |
|---|---|---|---|---|---|
| gatctgttgc | ctttattgtt | acgcagagtt | ggtggttcag | catcttatca | gcgattatct | 60 |
| atatgatctt | ctgcttagtc | atcgctgact | ggacagcaaa | ggatgtacaa | gaattttacg | 120 |
| gattagaagg | aattagtttt | ccaacaggtt | caagtgacgc | gtttggcctt | ttgggaattc | 180 |
| caatttcagc | agctattgca | aggattcctg | gaattaagaa | cctgcatgct | gattctgaaa | 240 |
| caattcaaaa | gcgttttggt | atctttggtg | aaccaatggt | aatggggatt | attattggcg | 300 |
| ccgctattgg | tgcgcttggc | ggatacgata | ttgctggtat | tttaaaactt | ggtatcaaca | 360 |
| tgggagctgt | tatgatgctg | atgcccgaga | atggtcaagt | tgctgatgga | aggcttaatg | 420 |
| ccaatttctg | agtctgcacg | aggggttctt | caaaagcgtt | atggtaagga | tcgtgagatt | 480 |
| tatcttggta | tggatgcggc | cttatcaaca | ggagcaccag | ccacattagc | gacaggcttg | 540 |
| ttgttggttc | ctattacttt | gtttatagca | gtgattctgc | ctggaaatag | ggtgctgcct | 600 |
| tttggagatt | tagcaacaat | tccatttat | gtatcccttta | tcgttgctag | gaggcgtggc | 660 |
| aatattatcc | attcagtctt | agcaggagcc | gttgtcatca | cattggcatt | gtttatggct | 720 |
| actgacttta | gtcctgtgca | tacgagatg | ctacgcggag | ttgtgaaatt | ccctgctggt | 780 |
| tcagcacaag | tttcttccct | cgatatgggc | ggtaatttct | taaactggat | tctccttaaa | 840 |
| ttctcagagc | tggtaaaagg | attcatttaa | tgaaagaggg | aaatttcatt | gaaagcatca | 900 |
| atgttggaag | atctaaataa | attctcggta | aagaaattg | atatccctag | tccaaaaaag | 960 |
| gacgaagttg | ttgttaaagt | catggctgct | ggtacatgtg | gatccgatag | ccataagatg | 1020 |
| attagcggat | ggaagtatgg | ctatccggcc | gttatgggcc | acgagtctc | aggtattgtt | 1080 |
| acgcaattag | gggagaatgt | ttcaaatgtt | tcagtaggtc | aacatgtagc | tgtagcgcct | 1140 |
| tttataccat | gtttcaagtg | tcactattgt | cagattggcc | ttttccagat | gtgtgaaaat | 1200 |
| tactcaatgc | tggggcaaca | aaagttcggt | ggttttgaac | aatatgttag | tgttcctgcc | 1260 |
| agaaacgttc | ttgatatcgg | aaagatgagt | tttgaagagg | gagcgttaat | tgaaccaatg | 1320 |
| gctgtagcgg | ctcacgccgt | aatgggaatt | aagccagaat | tgggcgatac | cgttgctgtc | 1380 |
| tttggattgg | gtacggttgg | cgatttagtg | gtccgcttat | taatttcttc | aggggcaact | 1440 |
| aatgtgattg | gaattgatat | cgatgatcaa | aagttagaaa | agggcctaga | tgaaggttgc | 1500 |
| acccacgtca | ttaattctgc | aaaagaatct | ttagaagaaa | agattatgga | atatactgac | 1560 |
| ggtcttggcg | ttgatatatc | aatggagtgc | gctgggtcaa | agattacgga | agagcaaaca | 1620 |
| ttgcttgtta | caaaaagacg | cggcaaggtt | gggtttgttg | gaattgccta | ctcagatgtt | 1680 |
| ttgttacatc | aaaaggcttt | tgaaaacatc | ttccgacatg | aattaactgt | aacaggtttt | 1740 |
| tggaactcgt | attctgctcc | gttccctggt | agggaatgga | ctaattcaat | tcaattggtg | 1800 |
| aatagaggtc | gaataaaaat | caaagatctc | ataactcacc | gatttgagtt | agaagatatg | 1860 |
| caaaaggctt | ttaacatgat | tacgactcgt | tcggaatcct | ttaataaagt | gatgtttttt | 1920 |
| ccgaatggca | taaattgatt | ttgtttatat | tttggtgaaa | ttggaggcat | tttataatgg | 1980 |
| atgcagtgaa | aactaagaca | atgaaagcag | tcgtcaaatc | agaacctgga | tacgatcaca | 2040 |
| tgagtttgaa | gaatgtaccg | attccggaag | ttacgggcaa | tcatgttta | atgaaagtcg | 2100 |
| catatacagg | aatttgtggt | acc | | | 2123 |

<210> SEQ ID NO 49
<211> LENGTH: 349

<212> TYPE: PRT
<213> ORGANISM: Lactobacillus rhamnosus

<400> SEQUENCE: 49

```
Met Lys Ala Ser Met Leu Glu Asp Leu Asn Lys Phe Ser Val Lys Glu
1               5                   10                  15

Ile Asp Ile Pro Ser Pro Lys Lys Asp Glu Val Val Lys Val Met
            20                  25                  30

Ala Ala Gly Thr Cys Gly Ser Asp Ser His Lys Met Ile Ser Gly Trp
            35                  40                  45

Lys Tyr Gly Tyr Pro Ala Val Met Gly His Glu Phe Ser Gly Ile Val
50                  55                  60

Thr Gln Leu Gly Glu Asn Val Ser Asn Val Ser Val Gly Gln His Val
65                  70                  75                  80

Ala Val Ala Pro Phe Ile Pro Cys Phe Lys Cys His Tyr Cys Gln Ile
                85                  90                  95

Gly Leu Phe Gln Met Cys Glu Asn Tyr Ser Met Leu Gly Gln Gln Lys
                100                 105                 110

Phe Gly Gly Phe Glu Gln Tyr Val Ser Val Pro Ala Arg Asn Val Leu
            115                 120                 125

Asp Ile Gly Lys Met Ser Phe Glu Glu Gly Ala Leu Ile Glu Pro Met
            130                 135                 140

Ala Val Ala Ala His Ala Val Met Gly Ile Lys Pro Glu Leu Gly Asp
145                 150                 155                 160

Thr Val Ala Val Phe Gly Leu Gly Thr Val Gly Asp Leu Val Val Arg
                165                 170                 175

Leu Leu Ile Ser Ser Gly Ala Thr Asn Val Ile Gly Ile Asp Ile Asp
                180                 185                 190

Asp Gln Lys Leu Glu Lys Gly Leu Asp Glu Gly Cys Thr His Val Ile
            195                 200                 205

Asn Ser Ala Lys Glu Ser Leu Glu Glu Lys Ile Met Glu Tyr Thr Asp
210                 215                 220

Gly Leu Gly Val Asp Ile Ser Met Glu Cys Ala Gly Ser Lys Ile Thr
225                 230                 235                 240

Glu Glu Gln Thr Leu Leu Val Thr Lys Arg Arg Gly Lys Val Gly Phe
                245                 250                 255

Val Gly Ile Ala Tyr Ser Asp Val Leu Leu His Gln Lys Ala Phe Glu
            260                 265                 270

Asn Ile Phe Arg His Glu Leu Thr Val Thr Gly Phe Trp Asn Ser Tyr
            275                 280                 285

Ser Ala Pro Phe Pro Gly Arg Glu Trp Thr Asn Ser Ile Gln Leu Val
            290                 295                 300

Asn Arg Gly Arg Ile Lys Ile Lys Asp Leu Ile Thr His Arg Phe Glu
305                 310                 315                 320

Leu Glu Asp Met Gln Lys Ala Phe Asn Met Ile Thr Thr Arg Ser Glu
                325                 330                 335

Ser Phe Asn Lys Val Met Phe Phe Pro Asn Gly Ile Asn
                340                 345
```

<210> SEQ ID NO 50
<211> LENGTH: 354
<212> TYPE: PRT
<213> ORGANISM: Bacillus halodurans

<400> SEQUENCE: 50

```
Met Lys Ala Leu Asn Leu Tyr Gly Ile Gln Asp Leu Arg Phe Glu Glu
1               5                   10                  15

Thr Pro Ala Pro Ser Ile Glu His Asp Asp Ile Ile Lys Val
            20                  25                  30

Lys Ala Val Gly Ile Cys Gly Ser Asp Leu Ser Arg Tyr Lys Lys Leu
            35                  40                  45

Gly Pro Tyr Val Pro Gly Met Thr Phe Gly His Glu Phe Ala Gly Glu
        50                  55                  60

Val Val Lys Ile Gly Arg Ser Val Thr Gly Phe Ser Ile Gly Asp Arg
65                  70                  75                  80

Val Ala Ala Cys Pro Thr Tyr Thr Cys Gly Gln Cys Arg Tyr Cys Gln
                85                  90                  95

Leu Gly Glu Pro Thr Arg Cys Glu Arg Leu Ser Val Ile Gly Ala Arg
                100                 105                 110

His Pro Gly Ala Tyr Ala Glu Tyr Val Lys Leu Pro Ala Lys His Val
            115                 120                 125

Ile Pro Leu Pro Asn Val Val Asn Tyr Asp Glu Ala Ala Leu Ile Glu
        130                 135                 140

Pro Ala Ser Val Val Ala His Gly Phe Tyr Arg Thr Asn Ile Lys Pro
145                 150                 155                 160

Gly Ala Ser Val Ala Ile Met Gly Val Gly Ser Ile Gly Leu Leu Ala
                165                 170                 175

Val Gln Trp Ala Lys Ile Phe Gly Ala Thr Thr Val Phe Ala Ile Asp
            180                 185                 190

Ile Asp Glu Gln Lys Leu Asn Val Ala Asn Gln Leu Gly Ala Asp Val
        195                 200                 205

Leu Ile Ser Ser Leu Gln Arg Pro Ala His Lys Gln Ile Leu Glu Tyr
    210                 215                 220

Thr Asn Gly Ile Gly Val Asp Val Ala Val Glu Ser Ala Gly Thr Pro
225                 230                 235                 240

Ser Thr Ser Ala Gln Val Phe Ala Leu Pro Lys Lys Gly Gly Glu Val
                245                 250                 255

Val Phe Leu Gly Ile Pro Tyr Ala Asp Val Gln Ile Glu Arg Phe Tyr
            260                 265                 270

Phe Glu Lys Ile Val Arg Asn Glu Leu His Val Tyr Gly Ser Trp Asn
        275                 280                 285

Ala Leu Ser Ser Pro Phe Pro Gly Lys Glu Trp Ala Thr Thr Ile His
    290                 295                 300

Tyr Met Ser Ser Gly Gln Leu Asn Val Ala Pro Met Ile Ser Tyr Arg
305                 310                 315                 320

Leu Pro Leu Ala Lys Gly Pro Glu Thr Phe Gln Gln Ile Ala Lys Gly
                325                 330                 335

Glu Leu Lys Pro Thr Lys Val Leu Phe Tyr Pro Glu Lys Leu Ser Glu
            340                 345                 350

Arg Lys

<210> SEQ ID NO 51
<211> LENGTH: 350
<212> TYPE: PRT
<213> ORGANISM: Clostridium difficile

<400> SEQUENCE: 51

Met Lys Ala Ala Val Leu His Gly Thr Asn Asp Met Arg Phe Glu Asp
1               5                   10                  15
```

```
Ile Glu Ile Lys Pro Cys Glu Ser Asp Glu Val Lys Ile Lys Val Met
            20                  25                  30

Ala Ala Gly Ile Cys Gly Ser Asp Pro Pro Arg Val Leu Lys His Trp
        35                  40                  45

Lys Tyr Pro Val Pro Ala Ile Pro Gly His Glu Phe Ser Gly Val Ile
    50                  55                  60

Ala Glu Val Gly Lys Asp Val Lys Asn Val Lys Val Gly Asp Arg Val
65                  70                  75                  80

Val Ala Ile Pro Phe Ile Pro Cys Asn Glu Cys Glu Tyr Cys Lys Arg
                85                  90                  95

Gly Leu Phe Ser Leu Cys Asp Asp His Gly Met Leu Gly Ala Lys Ser
            100                 105                 110

Phe Gly Ala Phe Ala Glu Tyr Val Asn Ile Lys Ala Thr Asn Val Leu
        115                 120                 125

Pro Ile Gly Asp Met Asp Phe Glu Asp Ala Ala Met Ile Glu Pro Leu
    130                 135                 140

Ala Val Ala Met His Gly Val Leu Asn Ile Gly Val Gln Val Gly Asp
145                 150                 155                 160

Thr Val Ala Val Met Gly Ser Gly Thr Met Gly Gln Leu Val Ile Gln
                165                 170                 175

Gly Leu Lys Ile Ala Gly Ala Gly Thr Ile Ile Ala Val Asp Ile Ser
            180                 185                 190

Asp Asn Lys Leu Arg Glu Ser Lys Glu Leu Gly Ala Asp Ile Ile Ile
        195                 200                 205

Asn Ala Lys Asp Ile Asn Pro Val Glu Lys Ile Lys Glu Leu Thr Gly
    210                 215                 220

Gly Lys Gly Val Asp Ile Ala Leu Glu Cys Ala Gly Ser Lys Ile Thr
225                 230                 235                 240

Gln Glu Gln Cys Leu Leu Ile Thr Lys Lys Ser Lys Ile Gly Phe
                245                 250                 255

Leu Gly Ile Ala Tyr Ser Asp Ile Thr Leu Ser Glu Glu Ala Phe Glu
            260                 265                 270

Asn Ile Phe Arg Lys Glu Leu Glu Leu Lys Gly Phe Trp Asn Ser Tyr
        275                 280                 285

Ser Ala Pro Phe Pro Gly Gln Glu Trp Thr Lys Gly Ile Asn Leu Val
    290                 295                 300

Asn Glu Gly Lys Ile Lys Leu Lys Glu Met Val Ser His Arg Phe Ser
305                 310                 315                 320

Leu Glu Asp Thr Tyr Lys Ala Phe Glu Met Ile Arg Asp Arg Lys Glu
                325                 330                 335

Glu Phe Asn Lys Ile Leu Ile Leu Pro Gln Gly Val Glu Lys
            340                 345                 350

<210> SEQ ID NO 52
<211> LENGTH: 352
<212> TYPE: PRT
<213> ORGANISM: Clostridium difficile

<400> SEQUENCE: 52

Met Gly Asn Lys Met Arg Ala Ser Val Leu Tyr Asn Val Gly Asp Val
1               5                   10                  15

Arg Tyr Glu Met Val Asp Ile Pro Glu Ile Thr Asp Thr Gln Val Leu
            20                  25                  30

Val Asn Val Lys Tyr Val Gly Ile Cys Gly Ser Asp Leu Pro Arg Ser
        35                  40                  45
```

```
Met Val Ser Gly Leu Ser Gly Asn Thr Lys Tyr Pro Leu Ile Leu Gly
         50                  55                  60

His Glu Phe Ser Gly Glu Val Val Lys Ile Gly Lys Val Lys His
 65                  70                  75                  80

Ile Asn Val Gly Asp Arg Val Ala Val Ala Pro Leu Val Pro Cys Gly
                 85                  90                  95

Lys Cys Asp Tyr Cys Asn Glu Gly Asn Phe Gly Leu Cys Asp Asp Tyr
                100                 105                 110

Asn Ile Ile Gly Thr Arg Val Asn Gly Ala Phe Ala Glu Tyr Val Arg
            115                 120                 125

Val Pro Glu Glu His Ile Leu Lys Leu Pro Asp Thr Leu Asp Tyr Glu
        130                 135                 140

Thr Ala Ala Gly Ile Glu Pro Ala Thr Ile Ala Tyr His Gly Ile Ser
145                 150                 155                 160

Lys Ser Asn Ile Arg Val Gly Asp Ser Val Val Leu Gly Cys Gly
                165                 170                 175

Pro Ile Gly Gln Phe Val Ile Gln Trp Ala Lys Val Phe Gly Ala Ser
            180                 185                 190

Lys Ile Ile Ala Val Asp Ile Phe Asp Glu Lys Leu Glu Leu Ser Lys
        195                 200                 205

Leu Leu Gly Ala Asn Tyr Ile Leu Asn Ser Lys Glu Val Asn Val Ile
    210                 215                 220

Lys Glu Ile Lys Lys Ile Thr Asn Gly Gly Ala Asp Val Val Ile Glu
225                 230                 235                 240

Thr Ala Gly Ser Arg Phe Thr Gln Glu Gln Ser Leu Phe Val Ala Lys
                245                 250                 255

Lys Arg Gly Asn Ile Val Phe Val Gly Ile Ser His Thr Glu Leu Pro
            260                 265                 270

Leu Ser Ala Asp Ala Thr Glu Cys Ile Leu Arg Gly Glu Leu Thr Leu
        275                 280                 285

Lys Gly Ser Trp Asn Ser Tyr Thr Ser Pro Tyr Pro Gly Arg Ala Trp
    290                 295                 300

Thr Ala Thr Leu Asp Phe Met Glu Lys Gly Asp Ile Ile Phe Lys Pro
305                 310                 315                 320

Met Ile Ser Asp Lys Ile Gly Leu Asn Glu Val Gly Asp Phe Leu Ser
                325                 330                 335

Lys Met Ser Lys Arg Glu Ile Asn Phe Asn Lys Ile Leu Val Glu Ile
            340                 345                 350

<210> SEQ ID NO 53
<211> LENGTH: 350
<212> TYPE: PRT
<213> ORGANISM: Clostridium difficile

<400> SEQUENCE: 53

Met Lys Ser Val Arg Phe Tyr Gly Ile Arg Asp Thr Arg Val Glu Asp
1                5                  10                  15

Val Asp Val Pro Lys Ile Leu Glu Lys Asp Val Ile Ile Lys Val
            20                  25                  30

Lys Val Ala Gly Ile Cys Gly Ser Asp Ile Ser Lys Tyr Ser Lys Thr
        35                  40                  45

Gly Pro His Met Val Gly Glu Ile Leu Gly His Glu Phe Ser Gly Glu
    50                  55                  60

Val Ala Gln Val Gly Lys Glu Val Arg Ser Phe Lys Ile Gly Asp Arg
```

```
                65                  70                  75                  80
        Val Ala Val Cys Pro Ala Met Pro Cys Phe Glu Cys Asp Glu Cys Lys
                            85                  90                  95

Lys Gly Leu Tyr Ser Arg Cys Asn Asn Val Ala Ile Ile Gly Asn Lys
                           100                 105                 110

Glu Leu Gly Gly Cys Phe Ala Glu Tyr Thr Lys Val Lys Glu Arg Asn
                           115                 120                 125

Leu Ile Lys Ile Pro Asp Glu Ile Ser Tyr Glu Thr Ala Ala Ala Leu
                           130                 135                 140

Glu Pro Val Cys Ile Ala Gly His Gly Leu Phe Arg Ser Glu Ala Lys
        145                 150                 155                 160

Val Gly Asp Thr Val Val Leu Gly Thr Gly Pro Ile Gly Leu Phe
                           165                 170                 175

Ser Ile Gln Trp Ala Lys Ile Phe Gly Ser Thr Lys Ile Ile Ala Val
                           180                 185                 190

Asp Val Phe Asp Glu Lys Leu Asp Leu Ala Lys Glu Leu Gly Ala Asp
                           195                 200                 205

Ile Cys Ile Asn Ala Lys Glu Lys Asn Ile Val Glu Glu Ile Lys Arg
                           210                 215                 220

Leu Thr Asp Gly Asp Gly Ala Asp Ile Val Ile Glu Ser Ala Gly Thr
        225                 230                 235                 240

Pro Leu Thr Cys Gly Gln Val Leu Leu Ala Lys Lys Gly Gly Thr
                           245                 250                 255

Val Leu Tyr Ala Gly Val Pro Tyr Gly Asp Val Ala Leu Thr Arg Glu
                           260                 265                 270

Gln Phe Glu Lys Ile Val Arg Ser Glu Leu Thr Val Lys Gly Thr Trp
                           275                 280                 285

Phe Gly Asn Ser Phe Pro Phe Pro Gly Lys Glu Trp Ser Ala Gly Leu
                           290                 295                 300

Tyr His Met Gln Lys Gly Asp Met Asn Val Glu Lys Leu Val Thr His
        305                 310                 315                 320

Arg Ile Asn Leu Glu Glu Ala Pro Ala Tyr Phe Glu Lys Val Tyr Lys
                           325                 330                 335

Arg Asp Ile Phe Phe Gly Lys Ile Met Ile Asn Ile Asp Asn
                           340                 345                 350

<210> SEQ ID NO 54
<211> LENGTH: 33
<212> TYPE: DNA
<213> ORGANISM: Artificial Sequence
<220> FEATURE:
<223> OTHER INFORMATION: oDEGQ 5 primer

<400> SEQUENCE: 54
ggagtcgacc atgggagcac ctcgcaaaaa agg                              33

<210> SEQ ID NO 55
<211> LENGTH: 66
<212> TYPE: DNA
<213> ORGANISM: Artificial Sequence
<220> FEATURE:
<223> OTHER INFORMATION: DEGQ 3 primer

<400> SEQUENCE: 55
ggagaattca cctcctttca gagtcccggg tatttgatct gttactaata gtgtatctgc  60
tttcgg                                                            66
```

<210> SEQ ID NO 56
<211> LENGTH: 31
<212> TYPE: DNA
<213> ORGANISM: Artificial Sequence
<220> FEATURE:
<223> OTHER INFORMATION: oLRYPD 501 primer

<400> SEQUENCE: 56
ggtgaattca tgaaagcatc aatgttggaa a                            31

<210> SEQ ID NO 57
<211> LENGTH: 36
<212> TYPE: DNA
<213> ORGANISM: Artificial Sequence
<220> FEATURE:
<223> OTHER INFORMATION: oLRXPD 301 primer

<400> SEQUENCE: 57
ggttctagac cattataaaa tgcctccaat ttcacc                       36

<210> SEQ ID NO 58
<211> LENGTH: 42
<212> TYPE: DNA
<213> ORGANISM: Artificial Sequence
<220> FEATURE:
<223> OTHER INFORMATION: oBHDH2 51 primer

<400> SEQUENCE: 58
ggtcaattga tgaaagccct taatttatac ggcattcaag ac                42

<210> SEQ ID NO 59
<211> LENGTH: 35
<212> TYPE: DNA
<213> ORGANISM: Artificial Sequence
<220> FEATURE:
<223> OTHER INFORMATION: oBHDH2 31 primer

<400> SEQUENCE: 59
gcatctagag tatagttgat catcctcgtg ttcgg                        35

<210> SEQ ID NO 60
<211> LENGTH: 35
<212> TYPE: DNA
<213> ORGANISM: Artificial Sequence
<220> FEATURE:
<223> OTHER INFORMATION: oGDH52 primer

<400> SEQUENCE: 60
ggtgaattca tggatttatt attggctctt ctccc                        35

<210> SEQ ID NO 61
<211> LENGTH: 33
<212> TYPE: DNA
<213> ORGANISM: Artificial Sequence
<220> FEATURE:
<223> OTHER INFORMATION: oGDH3 primer

<400> SEQUENCE: 61
ggtagatcta gacattacag cgatggtgct gtc                          33

<210> SEQ ID NO 62
<211> LENGTH: 8
<212> TYPE: PRT
<213> ORGANISM: Enterococcus avium

<400> SEQUENCE: 62

```
<210> SEQ ID NO 63
<211> LENGTH: 8
<212> TYPE: PRT
<213> ORGANISM: Enterococcus avium

<400> SEQUENCE: 63

Gln Tyr Asn Leu Cys Pro His Arg
1               5

<210> SEQ ID NO 63
<211> LENGTH: 8
<212> TYPE: PRT
<213> ORGANISM: Enterococcus avium

<400> SEQUENCE: 63

Glu Ile Glu Tyr Ile Gly Ser Arg
1               5

<210> SEQ ID NO 64
<211> LENGTH: 14
<212> TYPE: PRT
<213> ORGANISM: Enterococcus avium

<400> SEQUENCE: 64

Lys Gln Gly Gln Phe Ile Gln Val Gly Leu Phe Ala Asn Lys
1               5                   10

<210> SEQ ID NO 65
<211> LENGTH: 11
<212> TYPE: PRT
<213> ORGANISM: Enterococcus avium

<400> SEQUENCE: 65

Gly Ala Ile Asn Ile Asp Glu Met Ile Thr Lys
1               5                   10

<210> SEQ ID NO 66
<211> LENGTH: 23
<212> TYPE: DNA
<213> ORGANISM: Artificial Sequence
<220> FEATURE:
<223> OTHER INFORMATION: oXP-1F primer
<221> NAME/KEY: misc_feature
<222> LOCATION: (12)..(12)
<223> OTHER INFORMATION: n is an inosine residue
<221> NAME/KEY: misc_feature
<222> LOCATION: (18)..(18)
<223> OTHER INFORMATION: n is an inosine residue

<400> SEQUENCE: 66
cartataatt tntgtccnca tmg                                    23

<210> SEQ ID NO 67
<211> LENGTH: 26
<212> TYPE: DNA
<213> ORGANISM: Artificial Sequence
<220> FEATURE:
<223> OTHER INFORMATION: oXP-4R
<221> NAME/KEY: misc_feature
<222> LOCATION: (12)..(12)
<223> OTHER INFORMATION: n is an inosine residue
<221> NAME/KEY: misc_feature
<222> LOCATION: (18)..(18)
<223> OTHER INFORMATION: n is an inosine residue
<221> NAME/KEY: misc_feature
<222> LOCATION: (21)..(21)
<223> OTHER INFORMATION: n is an inosine residue
<221> NAME/KEY: misc_feature
<222> LOCATION: (24)..(24)
<223> OTHER INFORMATION: n is an inosine residue

<400> SEQUENCE: 67
atcatttcrt cnatrttnat ngcncc                                 26
```

<210> SEQ ID NO 68
<211> LENGTH: 1400
<212> TYPE: DNA
<213> ORGANISM: Enterococcus avium

<400> SEQUENCE: 68

```
cattgacagt cgtgatggct gttgccttgt taatggcgac caattttgcg ccagtgatta      60
ctgaaatggc gcaagggatc gtgaagttcc cagaaggcgc tgctgaaatt acgaacttgg     120
atacaggcgg aaatttctta aaatggatct tcttgaaatt ctcagaatta gttgccacag     180
tgatgtagga ggttttttgta aatgagtaaa caatgaagg gtgtttccaa gcaggcaccc     240
ggttatgacc aaatggcatt tatcgattta tctgttccag aagcaacaga tgacaaggtc     300
ttgattaaag tcgcttatac aggtatttgc ggatcagata tccatacgtt taaaggtgaa     360
tacaaaaatc ccactactcc cgtcgtccta ggacatgaat tttctgggca ggtagttgaa     420
gtcggagcca atgtaacaaa ggtcaaggtt ggtgatcggg taaccagtga gacgaccttt     480
tatgtctgcg gcgaatgcga ttattgcaag gaaaagcagt ataatttgtg tccccatcga     540
aaaggaatcg gcacgcagca aaatggctcc atggcgaact atgtgttggc tcgagaagaa     600
agcattcatt tactgccgga tcatttaagc tatgaaggtg cggcgatgag cgaaccatta     660
gcgtgctgtg tccacgcgat gtatcaaaag agtcacttgg aattaaaaga cacgatcatt     720
atcatgggcc ctggaccaat cggactgtat cttttgcaga ttgccaagga aattggagcc     780
ttcgtcatta tgacggggat cacaaaagat gctcatcgct tagcattagc aaaaaaacta     840
ggcgcggatg tgatcgttga tacgatgaag gaagatctag cgaaagtcgt caatgagatc     900
acggatggct acggtgtcga taaagtgtat gatgcctcag gagcagttcc tgctgttaat     960
gctagtctgc cattgattcg caagcagggg caatttattc aagtaggctt gttcgctaat    1020
aaaatggtgg atttagacac tgaatcgatc attcaacgag agatcgaata catcggcagt    1080
cgttcacaga accctttatga ctggccgatt gcgatccact tattagcgaa aggtgcgatc    1140
aatatcgatg agatgattac gaaaaaatac ccgttgactg aatggcggga agcctttgat    1200
aaagtgatga aggcaatga atcaaggta atgatcgaat ccaatccaga agaattttaa    1260
tttgaatcaa ggaagctgta ccagaatttt tggtgcagct ttttgtgagt ttgttttata    1320
ggaggatttt tttgatacta ttttcatgag aacagtgtaa taaataatca ttagcaagaa    1380
attgtaaaag aatattgtat                                               1400
```

<210> SEQ ID NO 69
<211> LENGTH: 352
<212> TYPE: PRT
<213> ORGANISM: Bacillus halodurans

<400> SEQUENCE: 69

```
Met Ser Lys Thr Met Lys Gly Val Ser Lys Gln Ala Pro Gly Tyr Asp
1               5                   10                  15

Gln Met Ala Phe Ile Asp Leu Ser Val Pro Glu Ala Thr Asp Asp Lys
            20                  25                  30

Val Leu Ile Lys Val Ala Tyr Thr Gly Ile Cys Gly Ser Asp Ile His
        35                  40                  45

Thr Phe Lys Gly Glu Tyr Lys Asn Pro Thr Thr Pro Val Val Leu Gly
    50                  55                  60

His Glu Phe Ser Gly Gln Val Val Glu Val Gly Ala Asn Val Thr Lys
65                  70                  75                  80
```

Val Lys Val Gly Asp Arg Val Thr Ser Glu Thr Thr Phe Tyr Val Cys
            85                  90                  95

Gly Glu Cys Asp Tyr Cys Lys Glu Lys Gln Tyr Asn Leu Cys Pro His
            100                 105                 110

Arg Lys Gly Ile Gly Thr Gln Gln Asn Gly Ser Met Ala Asn Tyr Val
            115                 120                 125

Leu Ala Arg Glu Glu Ser Ile His Leu Leu Pro Asp His Leu Ser Tyr
            130                 135                 140

Glu Gly Ala Ala Met Ser Glu Pro Leu Ala Cys Cys Val His Ala Met
145                 150                 155                 160

Tyr Gln Lys Ser His Leu Glu Leu Lys Asp Thr Ile Ile Met Gly
            165                 170                 175

Pro Gly Pro Ile Gly Leu Tyr Leu Leu Gln Ile Ala Lys Glu Ile Gly
            180                 185                 190

Ala Phe Val Ile Met Thr Gly Ile Thr Lys Asp Ala His Arg Leu Ala
            195                 200                 205

Leu Ala Lys Lys Leu Gly Ala Asp Val Ile Val Asp Thr Met Lys Glu
            210                 215                 220

Asp Leu Ala Lys Val Val Asn Glu Ile Thr Asp Gly Tyr Gly Val Asp
225                 230                 235                 240

Lys Val Tyr Asp Ala Ser Gly Ala Val Pro Ala Val Asn Ala Ser Leu
            245                 250                 255

Pro Leu Ile Arg Lys Gln Gly Gln Phe Ile Gln Val Gly Leu Phe Ala
            260                 265                 270

Asn Lys Met Val Asp Leu Asp Thr Glu Ser Ile Ile Gln Arg Glu Ile
            275                 280                 285

Glu Tyr Ile Gly Ser Arg Ser Gln Asn Pro Tyr Asp Trp Pro Ile Ala
            290                 295                 300

Ile His Leu Leu Ala Lys Gly Ala Ile Asn Ile Asp Glu Met Ile Thr
305                 310                 315                 320

Lys Lys Tyr Pro Leu Thr Glu Trp Arg Glu Ala Phe Asp Lys Val Met
            325                 330                 335

Glu Gly Asn Glu Ile Lys Val Met Ile Glu Ser Asn Pro Glu Glu Phe
            340                 345                 350

<210> SEQ ID NO 70
<211> LENGTH: 343
<212> TYPE: PRT
<213> ORGANISM: Bacillus halodurans (deduced sequence)

<400> SEQUENCE: 70

Met Lys Ala Leu Val Lys Thr Gln His Gly Thr Gly His Phe Ala Val
1               5                   10                  15

Gln Glu Lys Pro Glu Pro Thr Pro Gly Lys His Gln Val Lys Ile Lys
            20                  25                  30

Val Lys Tyr Thr Gly Val Cys Gly Ser Asp Ile His Thr Tyr Glu Gly
            35                  40                  45

His Tyr Pro Val Ala Ala Pro Val Thr Leu Gly His Glu Phe Ser Gly
            50                  55                  60

Glu Ile Val Glu Leu Gly Glu Gly Val Thr Gly Phe Asn Val Gly Asp
65                  70                  75                  80

Arg Val Thr Ser Glu Thr Thr Tyr Ser Ile Cys Gly Lys Cys Ser Tyr
            85                  90                  95

Cys Thr Ser Gly Asp Tyr Asn Leu Cys Ser His Arg Lys Gly Leu Gly
            100                 105                 110

```
Asn Gln Gln Asp Gly Ser Phe Ala Lys Tyr Val Ile Ala Arg Gln Glu
        115                 120                 125

Ser Leu His His Leu Pro Ala Gly Val Asp Asp Arg Ser Ala Ala Met
        130                 135                 140

Thr Glu Pro Leu Ala Cys Thr His His Ala Ile Ala Lys Thr Ser Ile
145                 150                 155                 160

Asn Lys Gly Asp Leu Val Val Thr Gly Pro Gly Pro Ile Gly Leu
                165                 170                 175

Leu Ala Ala Gln Val Ala Lys Ser His Gly Gly Thr Val Ile Ile Thr
                180                 185                 190

Gly Leu Ser Asn Asp Gln Val Arg Leu Lys Lys Ala Lys Glu Val Gly
        195                 200                 205

Ile Asp Tyr Ala Ile Asp Thr Gln Glu Val Asp Ile Lys Glu Leu Val
        210                 215                 220

Ser Glu Leu Thr Asp Gly Tyr Gly Ala Asp Val Val Leu Glu Cys Ser
225                 230                 235                 240

Gly Ala Val Pro Ala Ala Lys Gln Gly Ile Asp Leu Leu Arg Lys Lys
                245                 250                 255

Gly Gln Tyr Ala Gln Val Gly Leu Phe Ala Gln Pro Glu Ile Gln Phe
                260                 265                 270

Asn Phe Glu Lys Ile Ile Gln Lys Glu Ile Ser Val Val Gly Ser Arg
        275                 280                 285

Ser Gln Lys Pro Ala Asp Trp Glu Pro Ala Leu Ser Leu Leu Asn Glu
        290                 295                 300

Lys Lys Val Asn Ala Lys Thr Leu Val Thr His Glu Tyr Thr Ile Ser
305                 310                 315                 320

Glu Trp Asp Lys Ala Tyr His Ala Ile Lys Ser Gly Glu Ala Ile Lys
                325                 330                 335

Val Leu Leu Thr Pro Ile Asp
                340
```